US012636357B2

(12) United States Patent
Kim et al.

(10) Patent No.:  US 12,636,357 B2
(45) Date of Patent:  May 26, 2026

(54) VACCINE COMPOSITION FOR PREVENTING TUBERCULOSIS COMPRISING CHORISMATE MUTASE

(71) Applicant: SEOUL NATIONAL UNIVERSITY R&DB FOUNDATION, Seoul (KR)

(72) Inventors: Bum Joon Kim, Seoul (KR); Byoung Jun Kim, Gyeonggi-do (KR); Jaehun Oh, Seoul (KR); Hyejun Seo, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 563 days.

(21) Appl. No.: 18/021,258

(22) PCT Filed: Aug. 12, 2021

(86) PCT No.: PCT/KR2021/010711
§ 371 (c)(1),
(2) Date: Feb. 14, 2023

(87) PCT Pub. No.: WO2022/035248
PCT Pub. Date: Feb. 17, 2022

(65) Prior Publication Data
US 2024/0033338 A1      Feb. 1, 2024

(30) Foreign Application Priority Data
Aug. 14, 2020    (KR) ........................ 10-2020-0102657

(51) Int. Cl.
*A61K 39/04* (2006.01)
*A61K 39/00* (2006.01)
*A61K 39/39* (2006.01)
*A61P 31/06* (2006.01)

(52) U.S. Cl.
CPC .............. *A61K 39/04* (2013.01); *A61K 39/00* (2013.01); *A61K 39/39* (2013.01); *A61P 31/06* (2018.01); *A61K 2039/523* (2013.01); *A61K 2039/5254* (2013.01); *A61K 2039/5256* (2013.01); *A61K 2039/55505* (2013.01); *A61K 2039/55516* (2013.01); *A61K 2039/55555* (2013.01); *A61K 2039/55561* (2013.01); *A61K 2039/55572* (2013.01); *A61K 2039/55577* (2013.01)

(58) Field of Classification Search
None
See application file for complete search history.

(56) References Cited

U.S. PATENT DOCUMENTS

2014/0004151  A1    1/2014  Sette et al.
2018/0085355  A1    3/2018  Abramovitch et al.

FOREIGN PATENT DOCUMENTS

| KR | 10-0951057 B1 | 3/2010 |
| KR | 10-2019-0071322 A | 6/2019 |
| KR | 10-2019-0128999 A | 11/2019 |

OTHER PUBLICATIONS

Haile et al. Immunization with heat-killed *Mycobacterium bovis* bacille Calmette-Guerin (BCG) in EurocineTM L3 adjuvant protects against tuberculosis. Vaccine 22 (2004) 1498-1508.*
Jeong et al. Potential of *Mycobacterium tuberculosis* chorismate mutase (Rv1885c) as a novel TLR4-mediated adjuvant for dendritic cell-based cancer immunotherapy. Oncoimmunology 2022, vol. 11, No. 1, e2023340.*
Seo et al. Protection against tuberculosis by vaccination of secreted chorismate mutase (Rv1885c) combined with a hepatitis B virus (HBV)-derived peptide, Poly6, and alum adjuvants. Vaccine 47 (2025) 126710.*
Orr et al. Adjuvant formulation structure and composition are critical for the development of an effective vaccine against tuberculosis. Journal of Controlled Release 172 (2013) 190-200.*
Xia et al. The aroQ-Encoded Monofunctional Chorismate Mutase (CM-F) Protein Is a Periplasmic Enzyme in Erwinia herbicola. Journal of Bacreriology, Aug. 1993, 175(15): 4729-4737.*
Safar et al., "The effect of adjuvants and delivery systems on Th1, Th2, Th17 and Treg cytokine responses in mice immunized with *Mycobacterium tuberculosis*-specific proteins," PLOS One, 15 (2): e0228381 (2020).
Lee et al., "Diagnostic Potential of IgG and IgA Responses to *Mycobacterium tuberculosis* Antigens for Discrimination among Active Tuberculosis, Latent Tuberculosis Infection, and Non-Infected Individuals," 8: 979 (2020).
Fletcher et al., "Human biomarkers: can they help us to develop a new tuberculosis vaccine," Future Microbiology, 11 (6): 781-787 (2016).
Khanapur et al., "*Mycobacterium tuberculosis* chorismate mutase: A potential target for TB," Bioorganic & Medicinal Chemistry, 25: 1725-1736 (2017).

(Continued)

*Primary Examiner* — Nianxiang Zou
(74) *Attorney, Agent, or Firm* — Morgan, Lewis & Bockius LLP

(57)      ABSTRACT

An aspect provides a vaccine composition for preventing tuberculosis comprising chorismate mutase. The vaccine composition alone may induce immunity specific to *Mycobacterium tuberculosis*, and when provided together with an immune adjuvant, the vaccine composition may induce immunity specific to tuberculosis more effectively. Furthermore, when an existing vaccine for tuberculosis is used as a prime and the vaccine composition according to an aspect including chorismite mutase is provided as a booster, the immunity specific to tuberculosis may be induced significantly more effectively.

15 Claims, 65 Drawing Sheets

Specification includes a Sequence Listing.

(56)              References Cited

OTHER PUBLICATIONS

Protecting Groups in Organic Synthesis, John Wiley & Sons, Chapters 5 and 7 (1991).
International Search Report issued in corresponding International Patent Application No. PCT/KR2021/010711 dated Nov. 24, 2021.

* cited by examiner

M          1          2          3

CD40

In splenocytes

In lung cells

IL-10 total IgG

FIG. 15A

PBS GROUP

GROUP IMMUNIZED WITH BCG

GROUP IMMUNIZED WITH TBCM

GROUP IMMUNIZED WITH TBCM+ALUM

GROUP IMMUNIZED WITH TBCM+POL6

Ag85B specific cell lysis

PBS GROUP

IMMUNIZATION WITH BCG ALONE

BCG PRIME-TBCM (Pol6) BOOSTING IMMUNIZATION

TBCM (Pol6) IMMUNIZATION

PBS GROUP

IMMUNIZATION WITH BCG ALONE

BCG PRIME-TBCM (Alum) BOOSTING IMMUNIZATION

TBCM (Alum) IMMUNIZATION

VACCINE COMPOSITION FOR PREVENTING TUBERCULOSIS COMPRISING CHORISMATE MUTASE

A computer readable text file, entitled "SequenceListing.txt," created on or about Jan. 30, 2023 with a file size of 4,152 bytes contains the sequence listing for this application and is hereby incorporated by reference in its entirety.

TECHNICAL FIELD

The disclosure relates to a vaccine composition for preventing tuberculosis including chorismate mutase.

BACKGROUND ART

Currently, only an attenuated live vaccine, *Mycobacterium bovis Bacillus* Calmette-Guerin (*M. bovis* BCG, BCG), is used as a preventive vaccine worldwide against *Mycobacterium tuberculosis*. BCG vaccination impedes the progression of tuberculosis in primary lesions by inducing a cell-mediated immune response, and is known to be effective particularly in preventing severe tuberculosis, such as miliary tuberculosis, tuberculous meningitis, etc., in infants and children. However, the preventive effect of BCG vaccination ranges from 0% to 80% and differences thereof vary widely among individuals, and is known to having little effect on adults. In addition, due to use of a live vaccine, infection may be caused in immunocompromised people or infants. To compensate for such limits of BCG, research on the development of next-generation tuberculosis vaccines is under way.

Tuberculosis vaccine candidates that have recently reached clinical trials include vaccines using inactivated whole cells or extracts of Mycobacteria (Vaccae, DAR-901, RUTI), attenuated strains (VPM1002, MTBVAC), recombinant attenuated viruses expressing tuberculosis proteins (TB/FLU-04L, Ad5Ag85A, ChAd0x1, 85A/MVA95A), and mixtures of Mycobacteria fusion proteins with immune adjuvants (M72:AS01E, H56:IC31, ID93:GLA-SE, GamTBvac), and the like.

Among these vaccines, protein-based vaccines targeting the main immune antigens of *M. tuberculosis* (Ag85A/B, ESAT-6, TB10.4) and the like have a difficulty in inducing a sufficient immune response using these antigens only, and thus research on the development of immune adjuvants is also being conducted at the same time. Examples of main immune adjuvants applied in clinical trials include AS01 which is a liposome mixed with monophosphoryl lipid A and saponin QS-21, IC31 consisting of an oligo nucleotide and a cationic peptide, CFA01 which is a cationic liposome, GLA-SE which is an oil-in-water emulsion of MPL and glucopyranosyl lipid, and the like.

The development of such tuberculosis vaccine is studied mainly by using the Ag85A/B antigen. In the case of MVA85A designed to express the Ag85A antigen by a vaccinia viral vector, it was a promising tuberculosis vaccine candidate that has been in phase 2 clinical trials by 2015. However, cases failed to show a difference in the incidence of tuberculosis in a clinical trial conducted in South Africa have been reported. In these cases, there may be problems with vectors and administration methods. However, due to the presence of various antigens involved in the defense against tuberculosis, it is suggested to consider discovering new tuberculosis antigens other than the Ag85A/B antigen or conducting research on tuberculosis vaccines using various antigens. In this regard, it is confirmed that, when mice are immunized with a TBCM protein derived from *M. tuberculosis* and a peptide-derived adjuvant candidate material (e.g., Poly6) together, immunity of the mice was more improved compared to a case where mice are immunized with TBCM alone or a combination of TBCM and a previously widely used adjuvant, Alum consisting of aluminum salt. Thus, a new tuberculosis protein-based vaccine is to be developed through this combination.

DETAILED DESCRIPTION OF THE INVENTION

Technical Problem

An aspect is to provide a vaccine composition for preventing tuberculosis including chorismate mutase.

Another aspect is to provide a prime booster vaccine composition for preventing tuberculosis including chorismate mutase.

Another aspect is to provide an immune-boosting composition including chorismate mutase.

Another aspect is to provide a method of preventing tuberculosis, the method including administering chorismate mutase to a subject in need thereof.

Another aspect is to provide an immune-boosting method, the method including administering chorismate mutase to a subject in need thereof.

Technical Solution to Problem

An aspect provides a vaccine composition for preventing tuberculosis including chorismate mutase.

The chorismate mutase according to an aspect may be chorismate mutase derived from *Mycobacterium tuberculosis*, and specifically, may be a protein expressed by a polynucleotide consisting of the base sequence of GenBank Gene ID: 885772.

The chorismate mutase may include a protein having sequence homology of about 70% or more, about 75% or more, about 80% or more, about 85% more, about 90% or more, about 92% or more, about 95% or more, about 97% or more, about 98% or more, or about 99% or more to the amino acid sequence (SEQ ID NO: 2) of a protein expressed by the polynucleotide consisting of the base sequence of GenBank Gene ID: 885772.

In detail, the chorismate mutase may include the amino acid sequence of SEQ ID NO: 2. In addition, the chorismate mutase may exist in the form of a dimer.

In addition, to better obtain chemical stability, enhanced pharmacological properties (e.g., half-life, absorbency, titer, efficacy, etc.), modified specificity (e.g., broad spectrum of biological activity), and reduced antigenicity, a protecting group may be bound to a N-terminus or a C-terminus of the protein. The protecting group may be an acetyl group, a fluorenyl methoxy carbonyl group, a formyl group, a palmitoyl group, a myristyl group, a steelyl group, or polyethylene glycol (PEG). However, any substance capable of improving protein modification, particularly protein stability, may be used without limitation.

The term "stability" may refer to not only in vivo stability that protects the protein according to an aspect from attack of a proteases in a living body, but also storage stability (e.g., storage stability at room temperature).

In addition, the protein may additionally include a targeting sequence, a tag, and an amino acid sequence prepared for a specific purpose for a labeled residue.

The term "homology" is intended to indicate the degree of similarity with a wild-type amino acid sequence. Such homology comparison may be performed by using a comparison program widely known in the art, and homology between two or more sequences may be calculated as a percentage (%).

The protein may be derived from the nature, or may be obtained by various protein synthesis methods well known in the art. In an embodiment, the protein may be prepared by using protein recombination and a protein expression system, an in vitro synthesis method through chemical synthesis such as peptide synthesis, a cell-free protein synthesis method, or the like. In one or more embodiments, the protein may be a product obtained by culturing a peptide, an extract of plant-derived tissues or cells, or a microorganism (e.g., bacteria or fungi, and especially yeast). In detail, the protein may be obtained by amplifying a DNA sequence corresponding to the *M. tuberculosis* chorismate mutase (TBCM) protein by using the genomic DNA of *M, tuberculosis* as a template, cloning it into a pET28a expression vector, and expressing and purifying the protein in *E. coli.*

In an embodiment, the tuberculosis may include eye tuberculosis, skin tuberculosis, adrenal tuberculosis, kidney tuberculosis, epididymal tuberculosis, lymphatic gland tuberculosis, laryngeal tuberculosis, middle ear tuberculosis, intestinal tuberculosis, multidrug-resistant tuberculosis, pulmonary tuberculosis, gall tuberculosis, bone tuberculosis, throat tuberculosis, lymph gland tuberculosis, sepsis, breast tuberculosis, or spinal tuberculosis. In addition, the tuberculosis may be caused by Korean highly pathogenic *M. tuberculosis*, K strains, or Beijing tuberculosis strains.

The term "prevention" may refer to any performance that suppresses or delays the onset of tuberculosis in a subject by administration of the vaccine composition according to an aspect.

The term "vaccine" refers to a pharmaceutical composition including at least one immunologically active ingredient that induces an immunological response in an animal. The immunologically active ingredient in the vaccine may include suitable elements (subunit vaccine) of live or dead viruses or bacteria, whereby these elements are prepared (called polynucleotide vaccination) by: destroying whole viruses or bacteria or growing cultures thereof and subsequently purifying to obtain desired structure(s), by a synthesis process induced by suitable manipulations of suitable systems using bacteria, insects, mammals, or other species and subsequently isolation and purification processes, or by induction of the aforementioned synthesis process in an animal in need of a vaccine by direct mixing of genetic materials using a suitable pharmaceutical composition. The vaccine may include one of the aforementioned elements or simultaneously at least one of the aforementioned elements.

In an embodiment, the vaccine composition may increase an expression level of at least one selected from IFN-γ, IL-12, IL-17, and TNF-α, and enhance induction of Th1 cell-mediated immunity, thereby providing a preventive effect on tuberculosis.

The vaccine composition may include an active ingredient alone, or may be provided by additionally including at least one immunologically acceptable carrier, excipient, or diluent.

In detail, the carrier may be, for example, a colloidal suspension, a powder, a saline solution, a lipid, a liposome, a microsphere, or a nano-spherical particle. Such a carrier may be complexed with or associated with a delivery vehicle, and may be delivered into a living body by using a delivery system known in the art, such as a lipid, a liposome, a microparticle, gold, a nanoparticle, a polymer, a condensation reagent, a polysaccharide, a polyamino acid, a dendrimer, a saponin, an adsorption-enhancing substance, or a fatty acid.

When the vaccine composition is formulated, a commonly used diluent or excipient, such as a lubricant, a sweetener, a flavoring agent, an emulsifier, a suspension, a preservative, a filler, an extender, a binder, a wetting agent, a disintegrant, a surfactants, and the like, may be used for preparation. Examples of a solid formulation for oral administration are a tablet, a pill, a powder, a granule, a capsule, and the like. Such a solid formulation may be prepared by mixing the composition with at least one excipient, such as starch, calcium carbonate, sucrose or lactose, gelatin, and the like. Also, in addition to a simple excipient, a lubricant, such as magnesium stearate and talc, may be used. Examples of a liquid formulation for oral administration are a suspension, an oral liquid, an emulsion, a syrup, and the like. In addition to water and liquid paraffin, which are simple diluents commonly used, various excipients, such as a wetting agent, a sweetening agent, a fragrance, a preservative, and the like, may be included. Formulations for parenteral administration, a sterile aqueous solution, a non-aqueous solution, a suspension, an emulsion, a lyophilized formulation, and a suppository may be included. As a non-aqueous solvent and suspension, propylene glycol, polyethylene glycol, vegetable oil, such as olive oil, and injectable ester, such as ethyl oleate, and the like may be used. As a suppository base, witepsol, macrogol, tween 61, cacao butter, laurin butter, glycerinated gelatin, and the like may be used. When prepared in the form of eye drops, a known diluent or excipient may be used.

The vaccine composition may be provided in the form of a mixture with a known vaccine composition for preventing tuberculosis or an existing tuberculosis vaccine. When the vaccine composition includes other vaccines having a preventive effect on tuberculosis, mixing in an amount that obtains a maximum effect with a minimum amount without any side effect is important, and such an amount may be easily determined by a person skilled in the art.

The other tuberculosis vaccines may be a previously known vaccine composition for preventing tuberculosis, an existing tuberculosis vaccine, or a newly developed tuberculosis vaccine.

In addition, in an embodiment, the vaccine composition may be administered alone or in combination with a known composition having a preventive effect on tuberculosis or with other tuberculosis vaccines, and may be administered simultaneously, separately, or sequentially, once or multiple times. Consideration all of the aforementioned factors, determining an administration method, an administration period, an administration dose, and the like to obtain a maximum effect with a minimum amount without any side effect is important, and these matters may be easily determined by a person skilled in the art.

In a case where the vaccine composition is mixed with other tuberculosis vaccines or administered in combination therewith, a synergistic effect in which the preventive effect on tuberculosis, i.e., boosting immune activity, is more significant than a case where the composition is provided alone or administered alone.

In an embodiment, the other tuberculosis vaccines may be *Bacillus* Calmette-Guerin (BCG).

The term "administration" refers to introducing a predetermined substance into an object by an appropriate method, and the term "subject" refers to all living organisms that can have tuberculosis, such as rats, mice, livestocks, and the like. A specific example of the living organisms is a mammal including a human.

In an embodiment, an administration route of the vaccine composition may be oral, intravenous, intramuscular, intra-arterial, intramedullary, intradural, intracardiac, percutaneous, subendothelial, intraperitoneal, intranasal, intestinal, intrathoracic, topical, sublingual, or intrectal application or external skin application, and specifically, may be include least one selected from subcutaneous injection and intranasal injection.

The vaccine composition may be administered to a subject in an immunologically effective amount. The term "immunologically effective amount" refers to an amount sufficient to exhibit a preventive effect on tuberculosis and an amount that does not cause a side effect or a severe or excessive immune reaction. The exact administration concentration may vary depending on a specific immunogen to be administered, may be easily determined by a person skilled in the art according to factors well known in the medical field, such as age, weight, health condition, and gender of a person to be vaccinated, drug sensitivity of a subject, an administration route, and an administration method, and the like, and may be administered once or several times.

For example, the vaccine composition according to an embodiment may be administered at a dose in a range of 0.1 ng/kg/day to 100 mg/kg/day.

In an embodiment, the administration of the vaccine composition may be performed once a day or in several times in divided doses. Specifically, based on 7 days, the vaccine composition may be administered at a period of 1 day of break after 6 days of administration, 2 days of break after 4 days of administration, 3 days of break after 4 days of administration, 4 days of break after 3 days of administrations, 5 days of break after 2 days of administration, and 6 days of break after 1 day of administration.

The vaccine composition according to an embodiment may include an immunologically acceptable vaccine protector, an immunopotentiator, a diluent, an absorption promoter, and the like, as needed. The vaccine protector may include, for example, a lactose phosphate glutamate gelatin mixture. The immunopotentiator may include, for example, aluminum hydroxide, mineral oil or other oils, or auxiliary molecules, such as interferons, interleukins, or growth factors, added to the vaccine or produced in the body after each induction by such additional substances. When the vaccine is a liquid formulation or in the form of an injection, the vaccine may include propylene glycol and a sufficient amount (e.g., about 1%) of sodium chloride to prevent hemolysis, as needed.

The vaccine composition according to an embodiment may further include, specifically an immune adjuvant as an immunopotentiator.

The immune adjuvant may include at least one selected from IL-12, granulocyte-macrophage colony-stimulating factor (GM-CSF), squalene, GLA-SE which is an oil-in-water emulsion of MPL and glucopyranosyl lipid, C-type lectin ligands (e.g., TDB), α-galactosylceramide, MF59, AS03, AS04, poly(I:C), monophosphoryl lipid A (MPL), GLA, flagellin, imiquimod, R848, CpG ODN, CpG DNA, QS-21 which is saponin, Freund adjuvant, muramyl dipeptide, lipopolysaccharide (LPS), Quil-A, aluminum salts (e.g., Alum), AS01 which is a liposome mixed with monophosphoryl lipid A and saponin QS-21, IC31 consisting of an oligo nucleotide and a cationic peptide, CFA01 which is a cationic liposome, and a polypeptide of SEQ ID NO: 1.

In detail, the immune adjuvant may include at least one selected from Alum consisting of aluminum salts and the polypeptide of SEQ ID NO: 1, and in more detail, may include both Alum consisting of aluminum salts the polypeptide of SEQ ID NO: 1.

The peptide, polypeptide, or amino acid of the protein may be conservatively or non-conservatively substituted in the present specification.

The term "conservatively substituted" as used herein refers to substitution of an amino acid present in the natural base sequence of a peptide with a natural or non-naturally occurring amino acid or a peptidomimetic having a similar steric property. When a side chain of the naturally occurring amino acid to be substituted is polar or hydrophobic, the conservative substitution should be present with a naturally occurring amino acid, a non-naturally occurring amino acid, or a peptidomic, each being polar or hydrophobic likewise (except for having the same steric property as the side chain of the substituted amino acid).

Since naturally occurring amino acids are typically classified according to properties thereof, conservative substitutions by naturally occurring amino acids may be readily determined by considering that the charged amino acids of the present disclosure are substituted with sterically similar uncharged amino acids that are considered conservative substituents.

To produce conservative substitutions with non-naturally occurring amino acids, amino acid analogues (e.g., synthetic amino acids) known in the art may also be used. Peptidomimetics of naturally occurring amino acids are well described in the documents known to a person skilled in the art.

When the conservative substitution is performed, the substituted amino acid should have the same or similar functional group on the side chain as the original amino acid.

The term "non-conservative substituents" as used herein refers to substitution of the same amino acid as present in a parent sequence with another naturally occurring or non-naturally occurring amino acid having different electrochemical and/or steric properties. Thus, the side chain of the substituted amino acid may be significantly larger than the side chain of the natural amino acid to be substituted, and/or may have functional groups with electrical properties that are significantly different from those of the amino acid to be substituted. Specific examples of the non-conservative substituents of the aforementioned type are substituents of phenylalanine or cyclohexyl methylglycine for alanine, isoleucine for glycine, or $-NH-CH[(-CH_2)_5-COOH]-CO-$ for aspartic acid.

Although the peptide or polypeptide as used herein are linear type, possible use of a cyclic peptide will be recognized unless cyclization does not significantly interfere with the peptide properties.

Since the peptide or polypeptide as used herein is used in a therapeutic agent that requires a soluble form of a peptide or polypeptide, the peptide or polypeptide of some embodiments herein may include at least one of serine and threonine that are unnatural or natural amino acids and capable of increasing the stability of the peptide or polypeptide due to hydroxyl-containing side chains, but embodiments are not limited thereto.

The N-terminus and C-terminus of the peptide or polypeptide of the present specification may be protected by a functional group. Suitable functional groups are described in "Protecting Groups in Organic Synthesis", Green and Wuts, Eds., John Wiley and Sons, Inc., Chapters 5 and 7, 1991, describing the contents of which are incorporated herein by reference. Thus, to produce an end-capped modified peptide or polypeptide, the peptide or polypeptide may be modified at the N-(amine) terminus and/or C-(carboxyl) terminus.

The expressions "end-capped modified polypeptide" and "protected polypeptide" as used herein may be used interchangeably herein, and refer to a polypeptide having modified N-(amine) terminus and/or C-(carboxyl) terminus. The end-capped modification refers to attachment of a chemical moiety to the terminus of a polypeptide to form a cap. Such a chemical moiety refers to an end-capped moiety in the present specification, and is interchangeably referred to as a peptide-protecting moiety or functional group in the present specification and in the art. Hydroxyl protecting groups may include ester, carbonate, and carbamate protecting groups, but are not limited thereto. Amine protecting groups may include alkoxy and aryloxy carbonyl groups, but are not limited thereto. Carboxylic acid protecting groups may include aliphatic esters, benzyl esters and aryl esters, but are not limited thereto.

The expression "end-capped moiety" as used herein refers to a moiety that modifies an N-terminus and/or C-terminus of a moiety when attached to the terminus. The end-capped modification typically results in masking charges at the end of the peptide and/or modifying chemical properties, such as hydrophobicity, hydrophilicity, reactivity, solubility, and the like, of the charges. By selecting the nature of the end-capped modifications, not only hydrophobicity/hydrophilicity, but also solubility of the peptide may be finely adjusted. In certain embodiments, the protecting groups may promote transport of the peptide attached thereto into cells. Such residues may be hydrolytically or enzymatically degraded in vivo in cells.

In certain embodiments, the end-capping may end-capping at N-terminus. Representative examples of end-capped residues at N-terminus may include formyl, acetyl (also referred to as "AC" herein), trifluoroacetyl, benzyl, benzyloxycarbonyl (also referred to as "Cbz" herein), tert-butoxycarbonyl (also referred to as "Boc" herein), trimethylsilyl (also referred to as "TMS" herein), 2-trimethylsilyl-ethanesulfonyl (also referred to as "SES" herein), trityl, substituted trityl groups, such as allyloxy carbonyl, 9-fluorenylmethyloxycarbonyl (also referred to as "Fmoc"), and nitro-veratryloxycarbonyl (also referred to as "NVOC" herein).

In certain embodiments, the end-capping may include end-capping at C-terminus. Examples of end-capped residues at C-terminus are typical residues that induce acylation of a carboxyl group at the C-terminus, such as alkyl ether, tetrahydropyranyl ether, trialkylsilyl ether, allyl ether, monomethoxytrityl, and dimethoxytrityl as well as benzyl and trityl ether. Optionally, the —COOH group of the end-capping at the C-terminus may be modified into an amide group.

The end-capping modification of other peptides includes substitution of amine and/or carboxyl with other moieties such as hydroxy, thiol, halide, alkyl, aryl, alkoxy, aryloxy, and the like.

Another aspect provides a prime-booster vaccine composition for preventing tuberculosis including chorismate mutase.

Descriptions of the chorismate mutase, tuberculosis, prevention, vaccine, or the like may be within the ranges above.

The term "prime-booster vaccine" as used herein refers to a combination of vaccines for at least one boosting immunity with a vaccine different from the one used for the prime immunization, or a method of administering such vaccines.

The chorismate mutase according to an embodiment may be chorismate mutase derived from *M. tuberculosis*, and specifically, may be a protein expressed by a polynucleotide consisting of the base sequence of GenBank Gene ID: 885772.

In an embodiment, the prime booster vaccine composition for preventing tuberculosis may further include an immune adjuvant.

The immune adjuvant may be at least one selected from squalene, GLA-SE, Freund adjuvant, muramyl dipeptide, lipopolysaccharide (LPS), Quil-A, Alum consisting of aluminum salts, AS01 consisting of a liposome mixed with monophosphoryl lipid A and saponin QS-21, IC31 consisting of an oligo nucleotide and a cationic peptide, CFA01 which is a cationic liposome, and a polypeptide of SEQ ID NO: 1.

In detail, the immune adjuvant may include at least one selected from Alum consisting of aluminum salts and the polypeptide of SEQ ID NO: 1, and in more detail, may include both Alum consisting of aluminum salts and the polypeptide of SEQ ID NO: 1.

In addition, in an embodiment, the prime-booster vaccine composition for preventing tuberculosis may increase an expression level of at least one selected from IFN-γ, IL-12, IL-17, and TNF-α, and may enhance induction of Th1 cell-mediated immunity, thereby providing a preventive effect on tuberculosis.

In an embodiment, an administration route of the prime-booster vaccine composition for preventing tuberculosis may be oral, intravenous, intramuscular, intra-arterial, intramedullary, intradural, intracardiac, percutaneous, subendothelial, intraperitoneal, intranasal, intestinal, intrathoracic, topical, sublingual, or intrectal application or external skin application, and in detail, may be include least one selected from subcutaneous injection and intranasal injection.

In addition, the prime-booster vaccine composition for preventing tuberculosis may be a booster vaccine using an attenuated virus (e.g., adenovirus or vaccinia virus) expressing a tuberculosis antigen (e.g., Ag85A/B, ESAT-6, TB10.4, etc.), or may be a BCG prime-booster vaccine.

Another aspect provides an immune-boosting composition including chorismate mutase.

Descriptions of the chorismate mutase, tuberculosis, prevention, vaccine, or the like may be within the ranges above.

The immune-boosting composition may increase an expression level of at least one selected from IFN-γ, IL-12, IL-17, and TNF-α, and may enhance induction of Th1 cell-mediated immunity, thereby providing an immune-boosting effect.

Another aspect provides a method of preventing tuberculosis, the method including administering chorismate mutase to a subject in need thereof.

Descriptions of the chorismate mutase, tuberculosis, prevention, vaccine, subject, administration, or the like may be within the ranges above.

In an embodiment, an administration route of the immune-boosting composition may be oral, intravenous, intramuscular, intra-arterial, intramedullary, intradural, intracardiac, percutaneous, subendothelial, intraperitoneal, intranasal, intestinal, intrathoracic, topical, sublingual, or intrectal application or external skin application, and in detail, may be include least one selected from subcutaneous injection and intranasal injection.

Another aspect provides an immune-boosting method, the method including administering chorismate mutase to a subject in need thereof.

9

10

Descriptions of the chorismate mutase, tuberculosis, prevention, vaccine, subject, administration, or the like may be within the ranges above.

In an embodiment, an administration route of the chorismate mutase may be oral, intravenous, intramuscular, intra-arterial, intramedullary, intradural, intracardiac, percutaneous, subendothelial, intraperitoneal, intranasal, intestinal, intrathoracic, topical, sublingual, or intrectal application or external skin application, and in detail, may be include least one selected from subcutaneous injection and intranasal injection.

The chorismate mutase may increase an expression level of at least one selected from IFN-γ, IL-12, IL-17, and TNF-α, and may enhance induction of Th1 cell-mediated immunity, thereby providing an immune-boosting effect.

Advantageous Effects of Disclosure

The vaccine composition for preventing tuberculosis including chorismate mutase according to an embodiment may induce *M. tuberculosis*-specific immunity alone, and may induce tuberculosis-specific immunity more effectively when provided together with an immune adjuvant. Furthermore, when the vaccine composition for preventing tuberculosis including chorismate mutase according to an embodiment is provided as a booster together with an existing tuberculosis vaccine as a prime, the tuberculosis-specific immunity may be induced significantly effectively.

BRIEF DESCRIPTION OF DRAWINGS

FIG. 19 is a diagram showing results of CTL responses induced by each immunized group; In detail.

FIG. 20 is a diagram showing an immunization experiment schedule (BCG prime-TBCM boosting) of a mouse by using a combination of TBCM and various adjuvant combinations after BCG immunization, wherein, in detail.

FIG. 21 is a diagram showing results of measuring CFU of *M. tuberculosis* in organs of a mouse after infecting a mouse immunized with BCG prime-TBCM boosting with *M. tuberculosis*. In detail.

MODE OF DISCLOSURE

Hereinafter, the present disclosure will be described in detail with reference to Examples below. However, these Examples are provided for illustrative purposes only, and the scope of the present disclosure is not limited thereto.

EXAMPLES

Figure 1A:
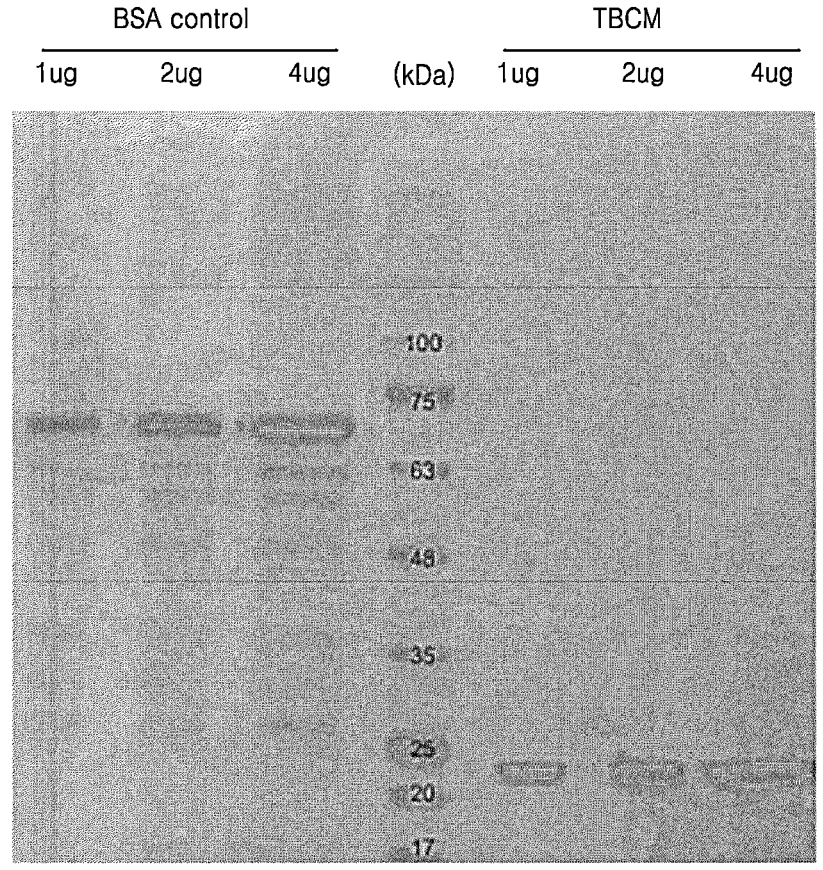
FIG. 1(A) shows coomassie blue staining results of a separated and purified TBCM protein on which SDS-PAGE is performed by concentrations.
Figure 1B:
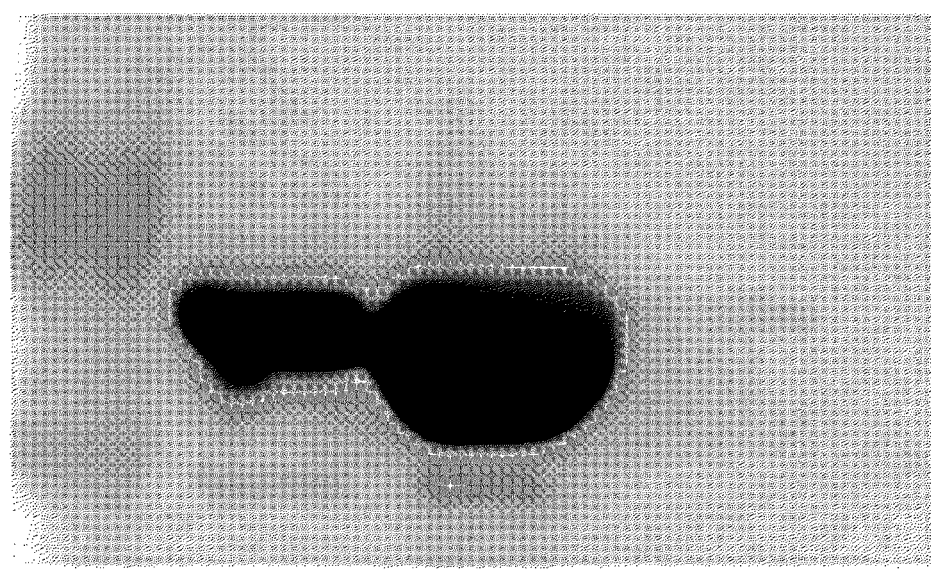
FIG. 1(B) shows western blotting results of the separated and purified TBCM protein treated with a polyclonal anti-TBCM antibody (M, marker; 1, TBCM (1 μg); 2, TBCM (5 μg); 3, and p24 (5 μg)).

1. Preparation and Confirmation of *M. tuberculosis* Chorismate Mutase (TBCM) Protein Expression Vector A polynucleotide sequence of SEQ ID NO: 2 encoding a protein of *M. tuberculosis*, TBCM (Rv1885c), was amplified by using the genomic DNA of *M. tuberculosis* as a template. Then, the amplified sequence was cloned into a pET28a expression vector (SEQ ID NO: 3; His tag included) to express a protein in *E. coli*. By purification, a TBCM protein of about 25 kD was obtained (FIG. 1).

2. Activation of Dendritic Cells by Peptide-Derived Adjuvant

After treatment with a peptide-derived adjuvant candidate, Pol6 (GRLVFQ, SEQ ID NO: 1), by concentrations (1 ng/ml, 10 ng/ml, 100 ng/ml, 1,000 ng/ml, and 10,000 ng/ml), the expression levels of dendritic cell maturation markers, CD40, CD86, and MHCII, were confirmed by flow cytometry.

Figure 2A:
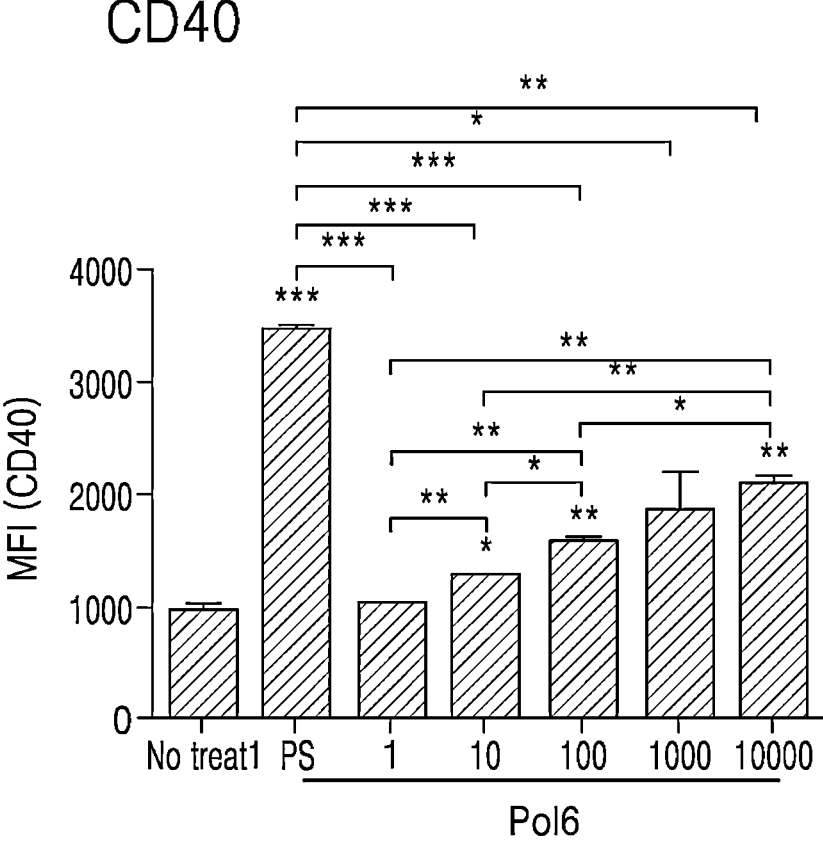
FIG. 2 shows a graph analyzing the expression of Pol6 by measuring dendritic cell maturation markers ((A) CD40, (B) CD86, and (C) MHCII) by flow cytometry after Pol6 is treated with dendritic cells by concentrations (statistical significance is tested by Student-t-test,*, P<0.05; , P<0.01; and *, P<0.001).
Figure 2B:
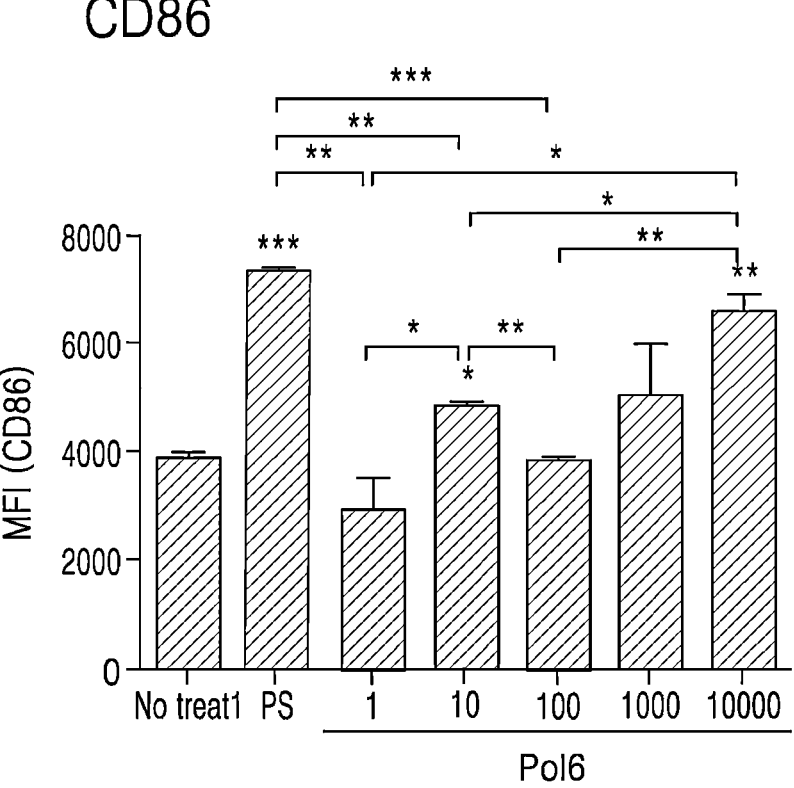
Figure 2C:
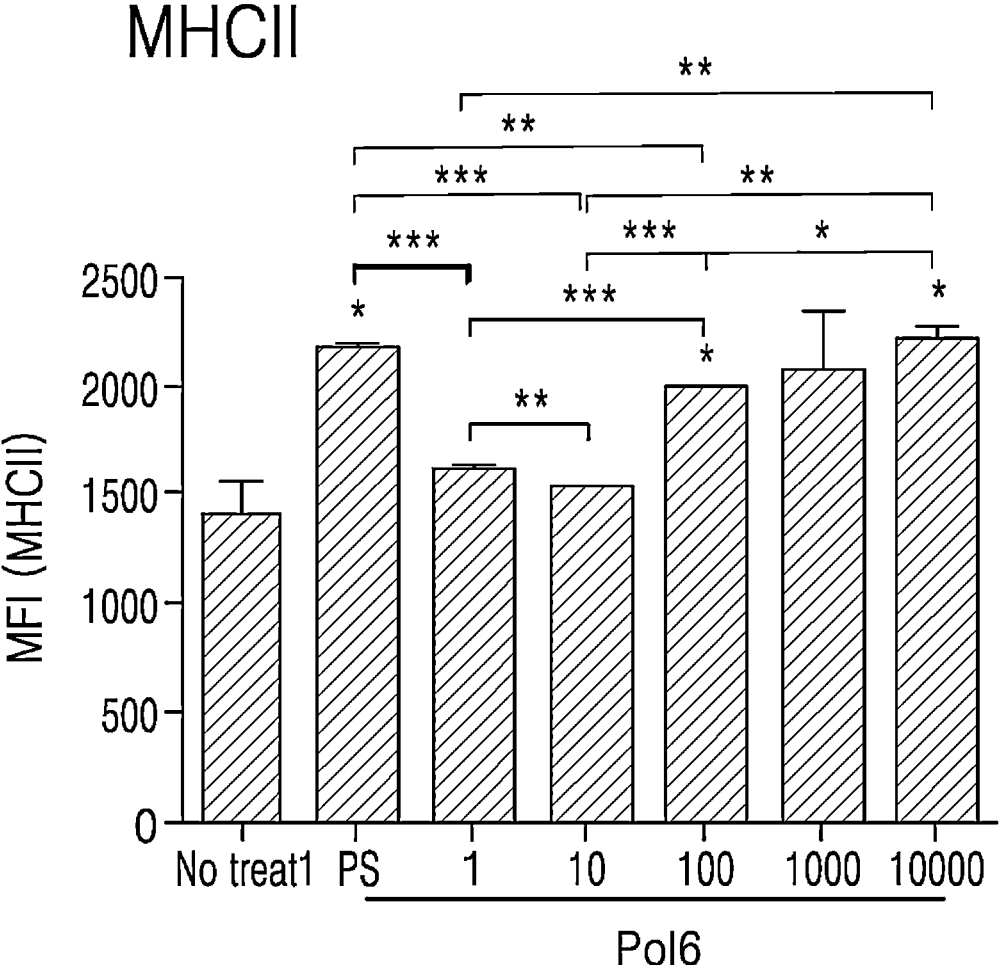

As a result, it was confirmed that the expression of CD40, CD86, and MHCII molecules in dendritic cells increased in a concentration-dependent manner when treated with Pol6 (FIG. 2).

3. Evaluation of Ability for Immune Induction Specific to TBCM and Tuberculosis Upon Mouse Immunization with TBCM and Pol6

Figure 3:
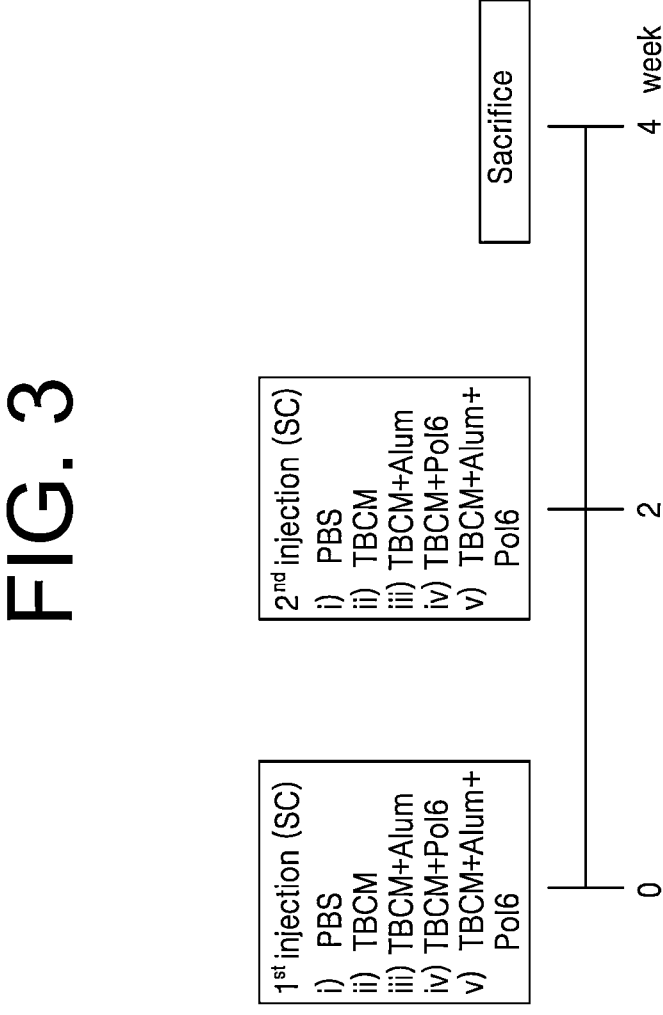
FIG. 3 is a diagram showing subcutaneous (SC) immunization schedule of mouse through a combination of TBCM and various adjuvants.

(1) Results of Ability for Immune Induction Specific to TBCM by (Subcutaneous, SC) Immunization with TBCM and Pol6 in Combination Mice were immunized (by SC injection) twice at 2-week intervals with a combination of TBCM and various adjuvants (TBCM alone, TBCM+Alum, TBCM+Pol6, and TBCM+Alum+Pol6) according to the schedule shown in FIG. 3. After the mice were sacrificed, TBCM-specific immune responses were observed in splenocytes and serum. The concentrations of TBCM protein and adjuvant were as follows:

i) TBCM (10 μg/mouse);

ii) Alum (100 μg/mouse); and iii) Pol6 (5 μg/mouse),

1) IFN-γ Enzyme-Linked Immunospot (ELISPOT) Assay

By using splenocytes of mice immunized with a combination of respective protein and adjuvant, the expression level of IFN-γ in response to TBCM antigen stimulation was confirmed by ELISPOT.

Figure 4:
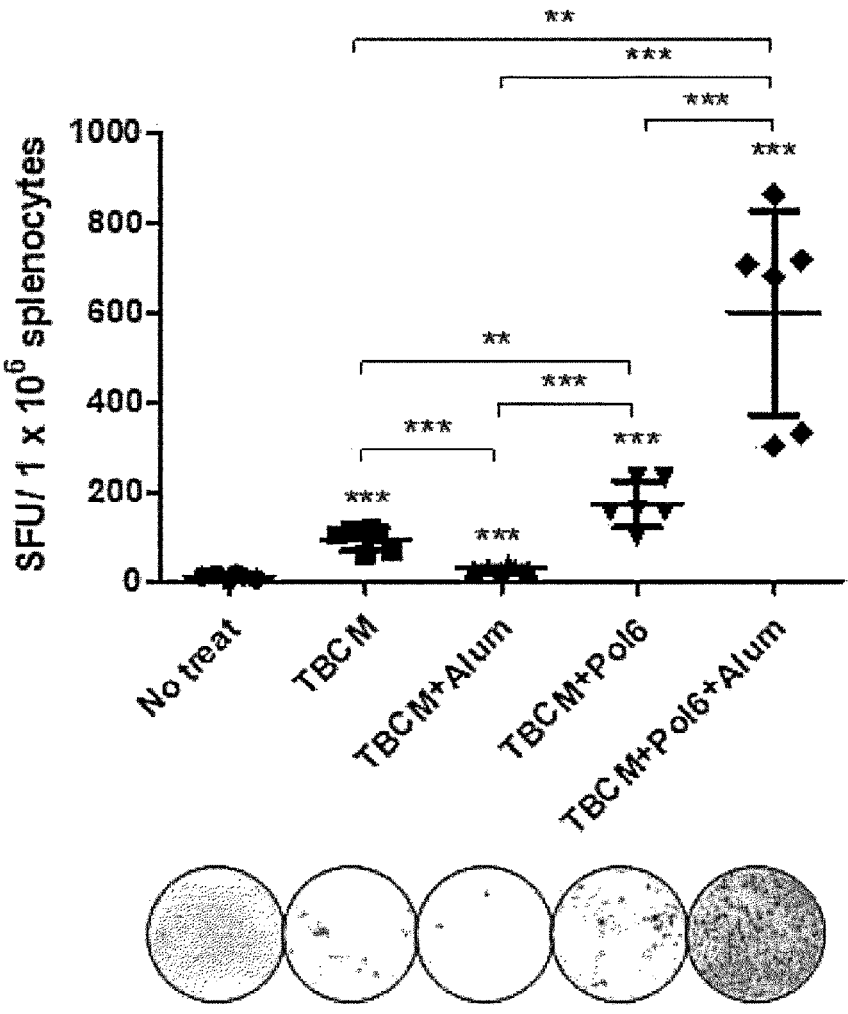
FIG. 4 is a diagram showing data obtained by measuring an expression level of IFN-γ in cells by ELISPOT when splenocytes obtained by immunization with a combination of TBCM and various adjuvants are stimulated with TBCM (statistical significance is tested by Student-t-test, *, P<; 0.05; , P<; 0.01; and *, P<0.001).
Figure 5A:
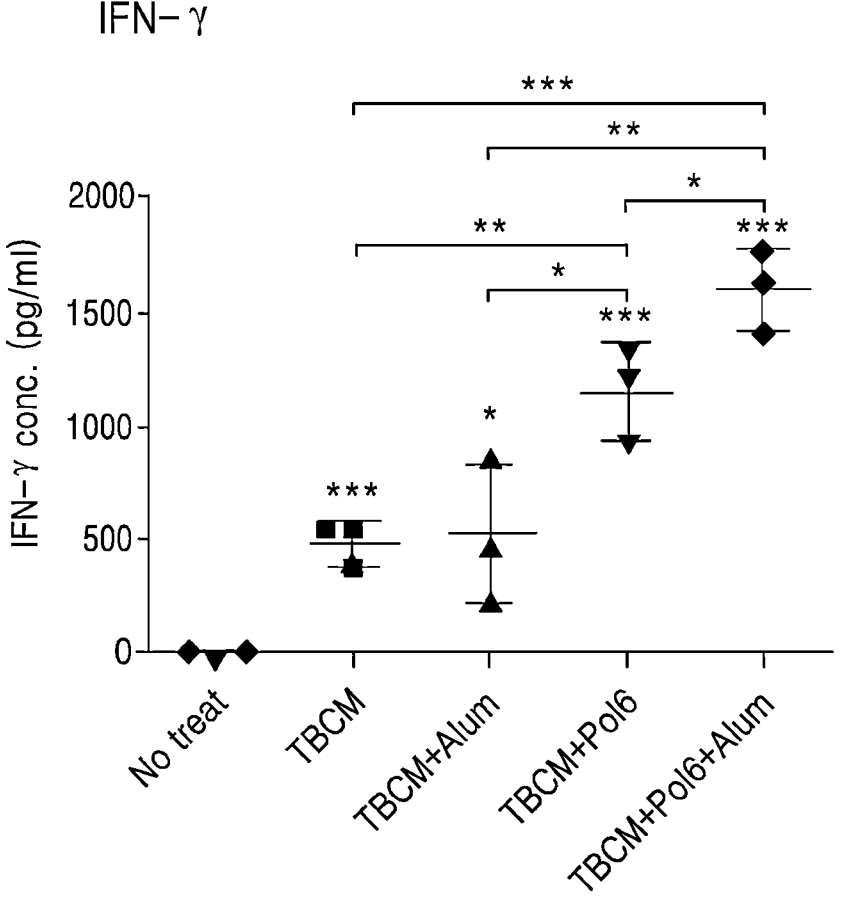
FIG. 5 is a diagram showing data obtained by confirming expression of (A) IFN-γ, (B) IL-12, (C) TNF-α, and (D) IL-10 cytokines in cells by ELISA when splenocytes obtained by immunization with a combination of TBCM and various adjuvants are stimulated with TBCM (statistical significance is tested by Student-t-test, *, P<; 0.05; , P<; 0.01; and *, P<0.001).
Figure 5B:
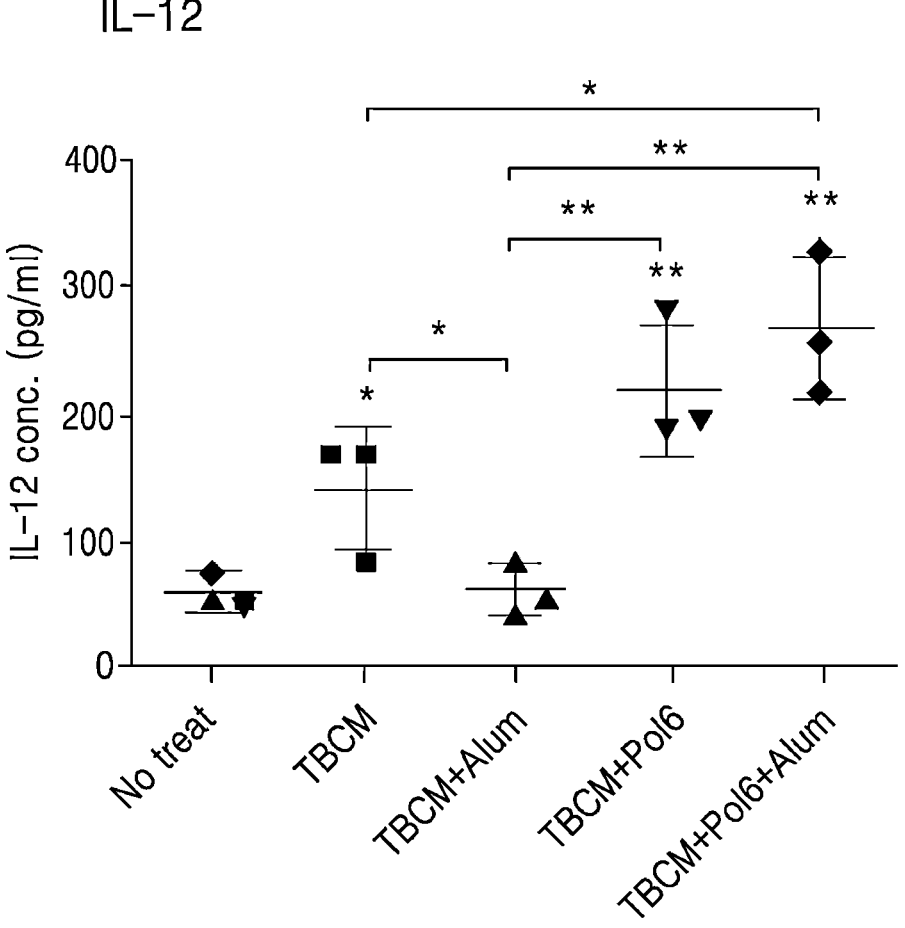
Figure 5C:
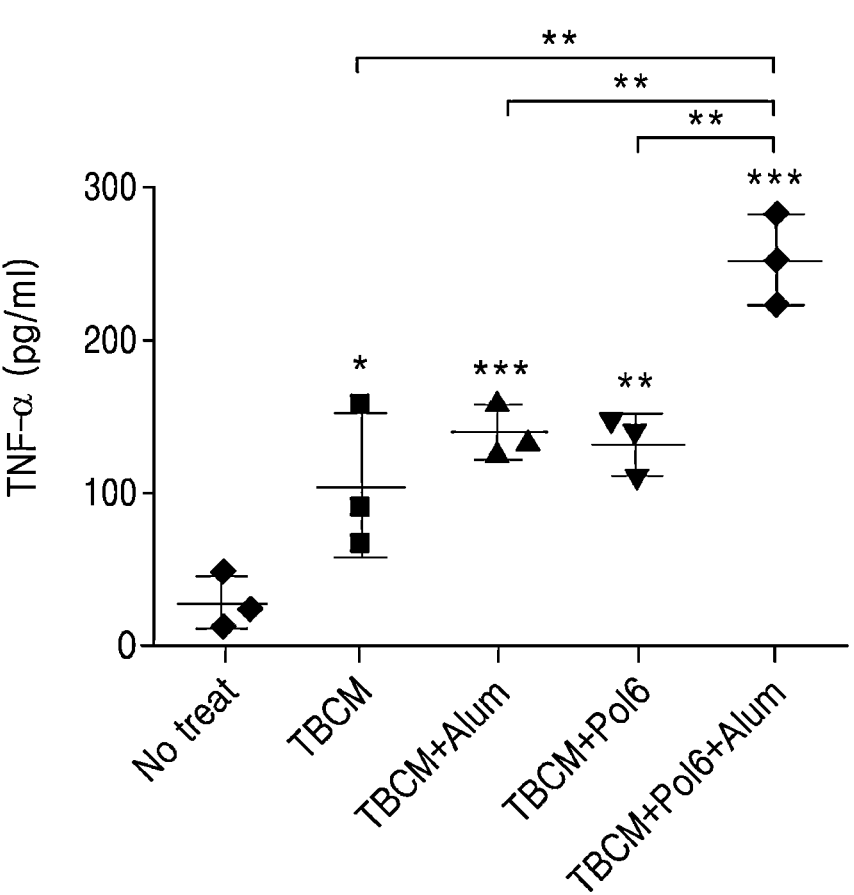
Figure 5D:
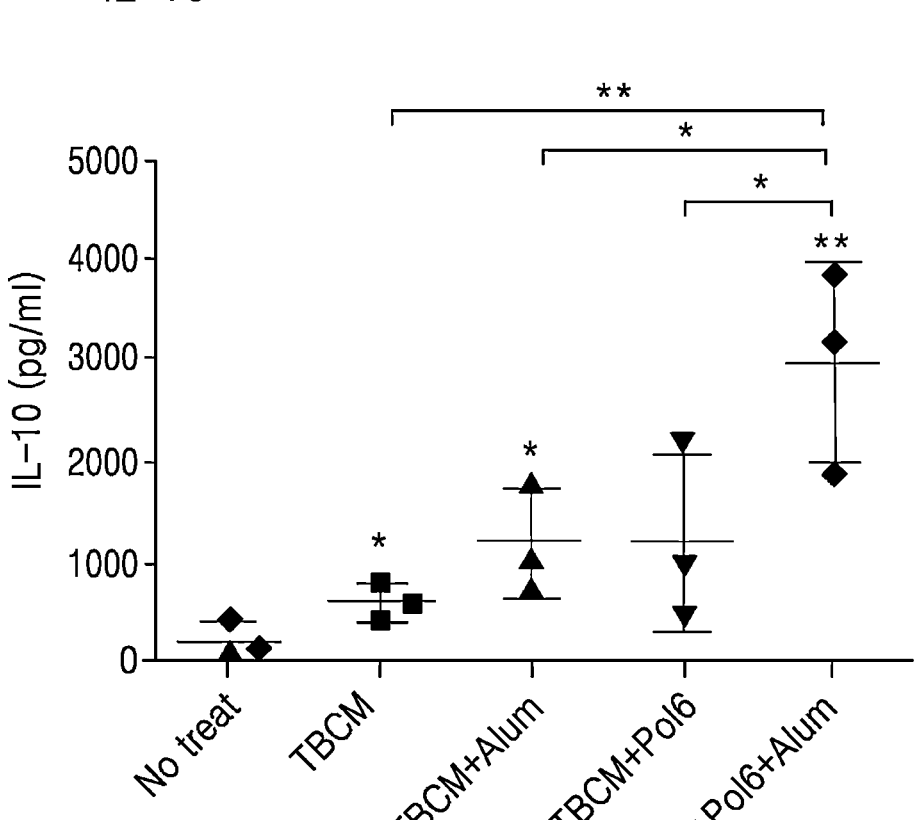

As a result, it was confirmed that, compared to cases immunized with TBCM alone and a combination of TBCM+Alum, IFN-γ spots were increased at a statistically significant level in a case immunized with a combination of TBCM+Pol6. In addition, it was confirmed that the expression level of IFN-γ specific to TBCM was at the highest level in a case immunized with a combination of TBCM+Alum+Pol6 (FIG. 4).

2) Measurement of Cytokines

After splenocytes of mice immunized with a combination of respective protein and adjuvant were stimulated with the TBCM protein, ELISA for IFN-γ, IL-12, TNF-α, and IL-10 was performed in a cell culture medium.

As a result, it was confirmed that the expression of IFN-γ and IL-12, which are important cytokines for protective immunity, in splenocytes of mice immunized with a combination of TBCM+Pol6 increased with statistical significance, compared to cases immunized with TBCM alone and a combination of TBCM+Alum (FIG. 5).

In addition, in a case immunized with a combination of TBCM+Alum+Pol6, the expression levels of IFN-γ and IL-12 were higher than those in a case immunized with other combinations (FIG. 5).

Regarding TNF-α, which is an inflammatory cytokine, and IL-10, which is an anti-inflammatory cytokine, a case immunized with a combination of TBCM+Pol6 showed similar expression patterns with a case immunized with TBCM alone and a combination of TBCM+Alum. In splenocytes of mice immunized with a combination of TBCM+Alum+Pol6, the expression levels of TNF-α and IL-10 were higher than those in a case immunized with other combinations (FIG. 5).

3) Measurement of IgG in Serum

IgG2, IgG1, and total IgG specific to TBCM in serum of mice immunized with a combination of respective protein and adjuvant were evaluated by ELISA.

Figure 6A:
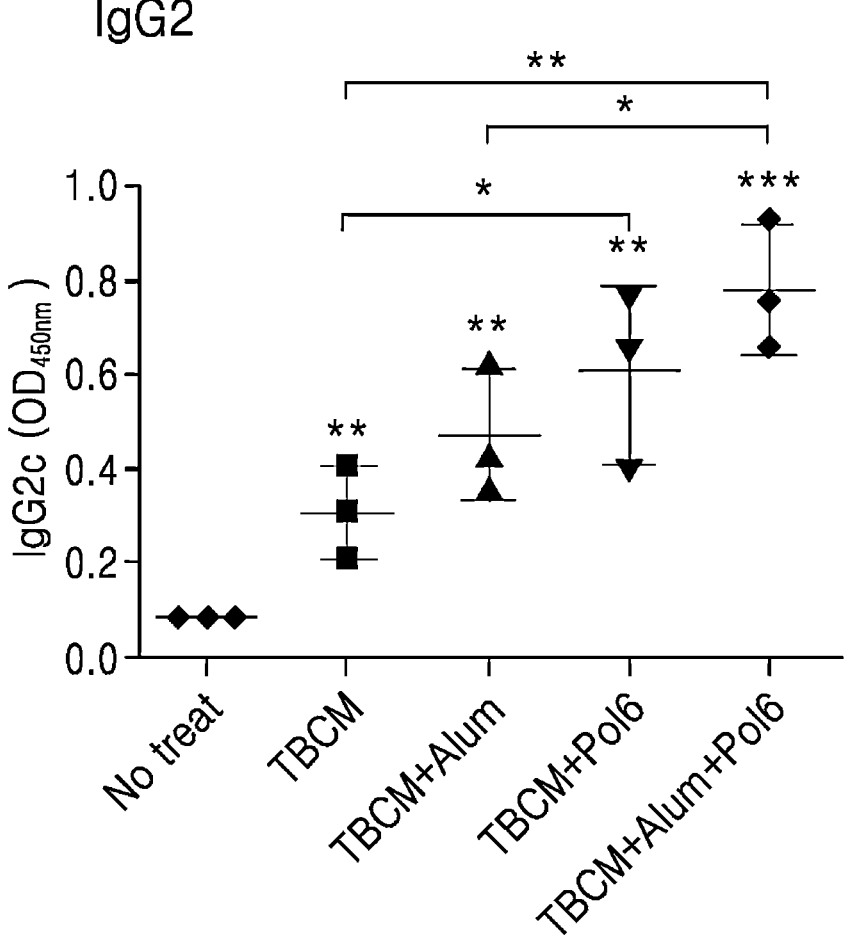
FIG. 6 is a diagram showing data obtained by confirming expression of (A) IgG2, (B) IgG1, and (C) total IgG that are specific to TBCM in serum by ELISA after immunization with a combination of TBCM and various adjuvants (statistical significance is tested by Student-t-test, *, P<0.05; , P<0.01; and *, P<0.001).
Figure 6B:
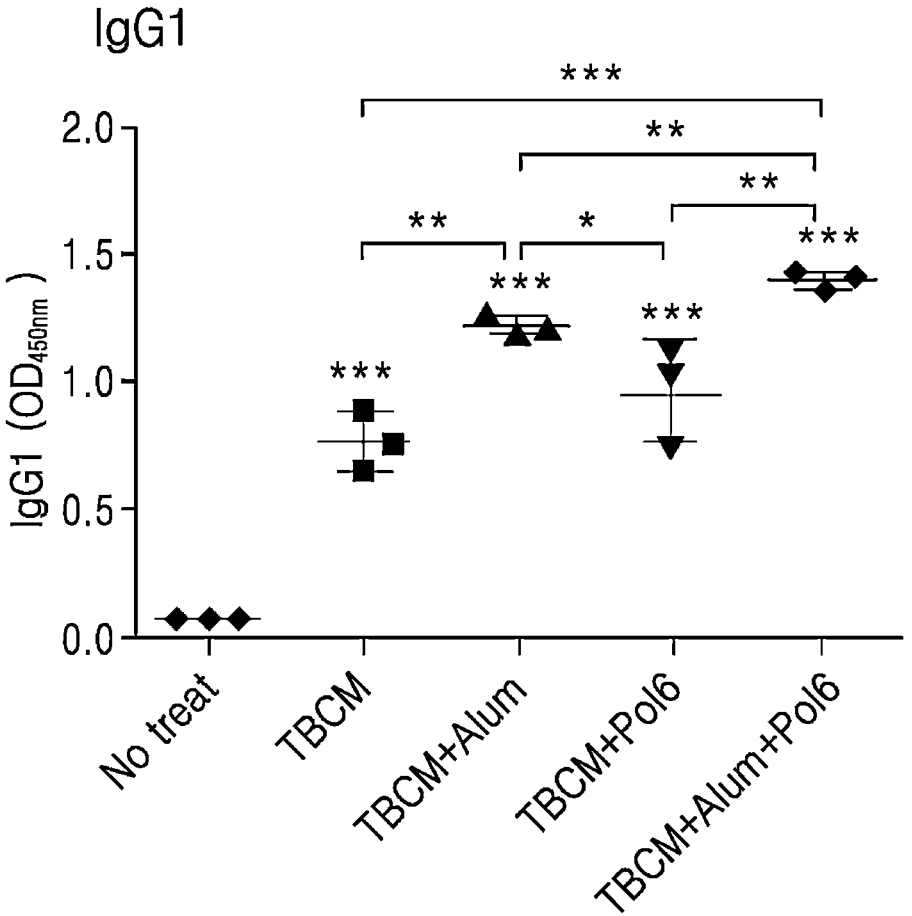
Figure 6C:
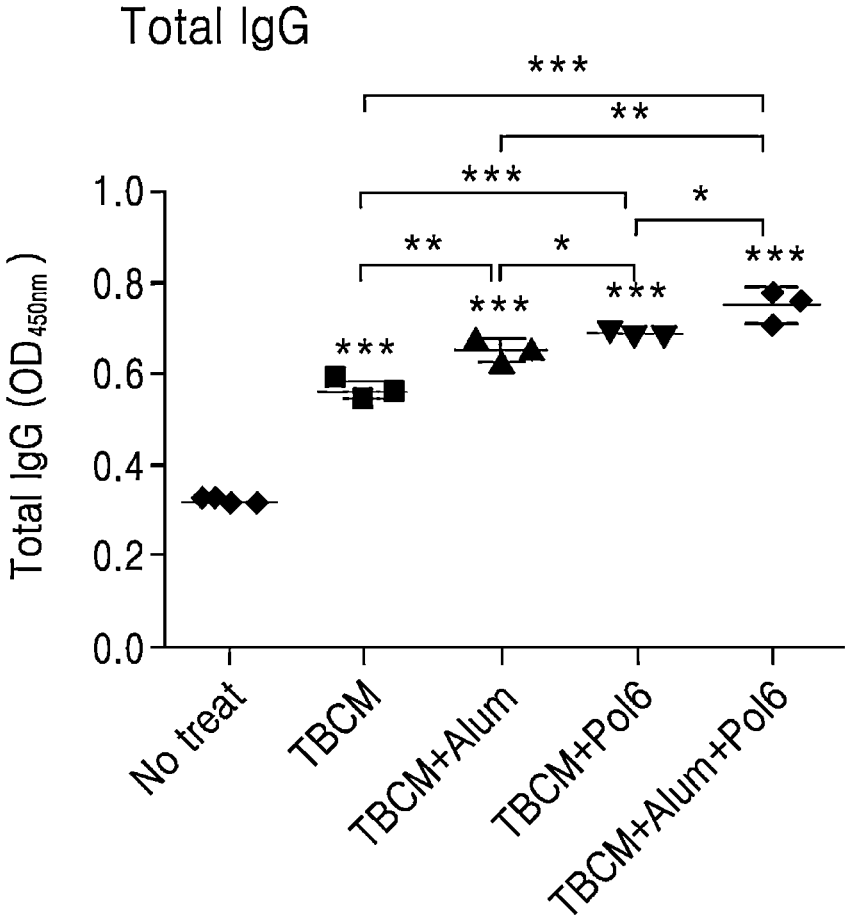

Comparing the expression of IgG2, the expression of IgG2 increased in a group immunized with an adjuvant in addition to TBCM compared to a group immunized with TBCM alone. In detail, a case immunized with a combination of TBCM+Pol6 showed relatively increased expression compared to a case immunized with a combination of TBCM+Alum, but there was no statistical significance. In addition, in a case immunized with a combination of TBCM+Alum+Pol6, the expression level of IgG2 was the highest with statistical significance among all other immunization groups except for a group immunized with a combination of TBCM+Pol6 (FIG. 6).

Regarding IgG1, the IgG1 expression in a case immunized with a combination of TBCM+Pol6 was similar with that in a case immunized with TBCM alone and was relatively low compared to that in a case immunized with a combination thereof TBCM+Alum. As in the previous comparison of IgG2 expression, the IgG1 expression in a case immunized with a combination of TBCM+Alum+Pol6 was tended to increase compared to cases of other immunized groups (FIG. 6).

IgG2 is known to be associated with the Th1 immune response and IgG1 is known to be associated with the Th2 immune response. In this regard, it was found that the IgG2 expression higher in a case immunized with a combination of TBCM+Pol6 than in cases immunized with TBCM alone and a combination of TBCM+Alum and the IgG1 expression similar to or lower mean that the Th1 biased immune response was increased by such combinations.

Figure 7:
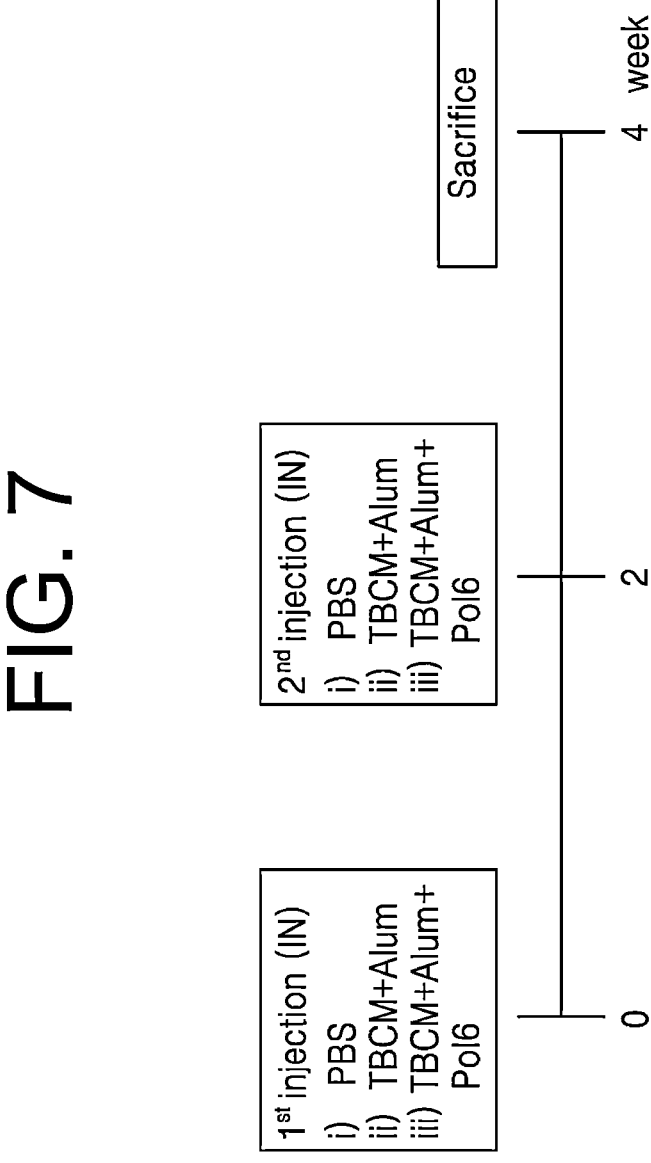
FIG. 7 is a diagram showing IN immunization schedule of mouse through a combination of TBCM and Alum or additionally Pol6.

(2) Results of Ability for Immune Induction Specific to TBCM by (Intranasal, IN) Immunization with TBCM and Pol6 in Combination Mice were immunized ((by intranasal (IN) injection) twice at 2-week intervals with a combination of TBCM and alum or additionally with Pol6 according to the schedule shown in FIG. 7. After the mice were sacrificed, TBCM-specific immune responses were observed in splenocytes, pneumocytes, bronchoalveolar lavage (BAL) fluid, and serum. The concentrations of TBCM protein and adjuvant were as follows:

i) TBCM (10 µg/mouse);
    ii) Alum (100 µg/mouse); and
    iii) Pol6 (5 µg/mouse).

1) IFN-γ ELISPOT Assay

By using splenocytes and pneumocytes of mice immunized with a combination of TBCM and Alum or additionally Pol6, the expression level of IFN-γ in response to TBCM antigen stimulation was confirmed by ELISPOT.

Figure 8A:
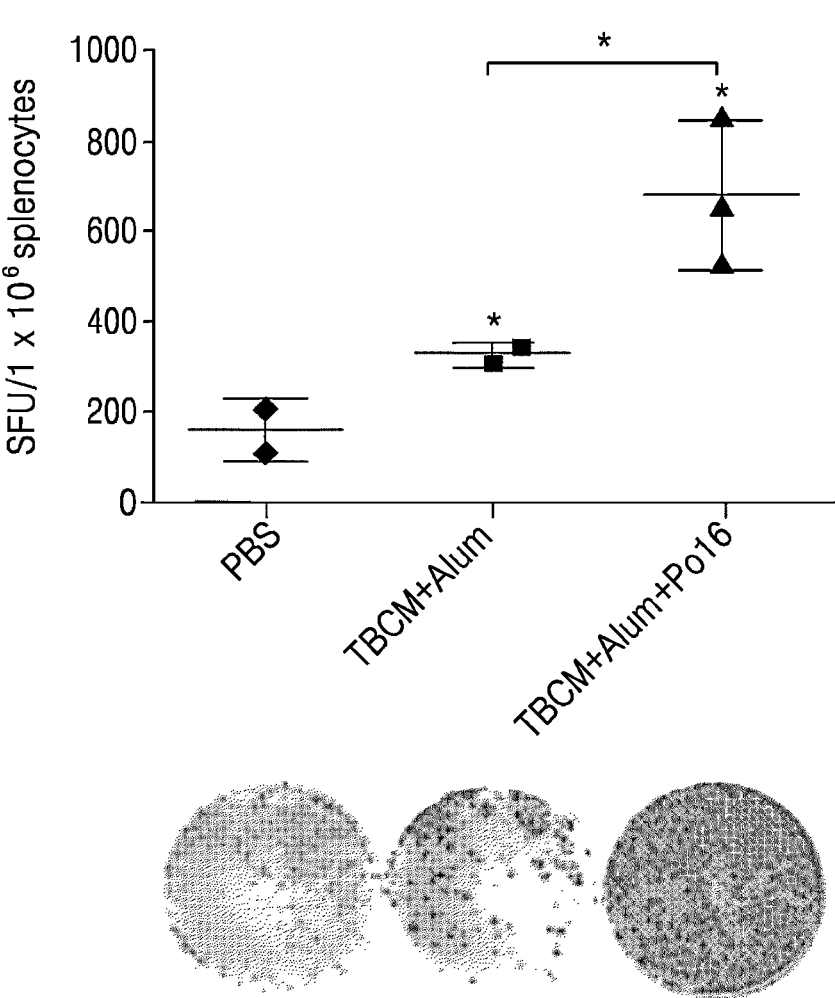
FIG. 8 is a diagram showing data obtained by measuring an expression level of IFN-γ in cells by ELISPOT when splenocytes obtained by immunization (IN route) with a combination of TBCM and Alum or additionally Pol6 are stimulated with TBCM (statistical significance is tested by Student-t-test, *, P<; 0.05).
Figure 8B:
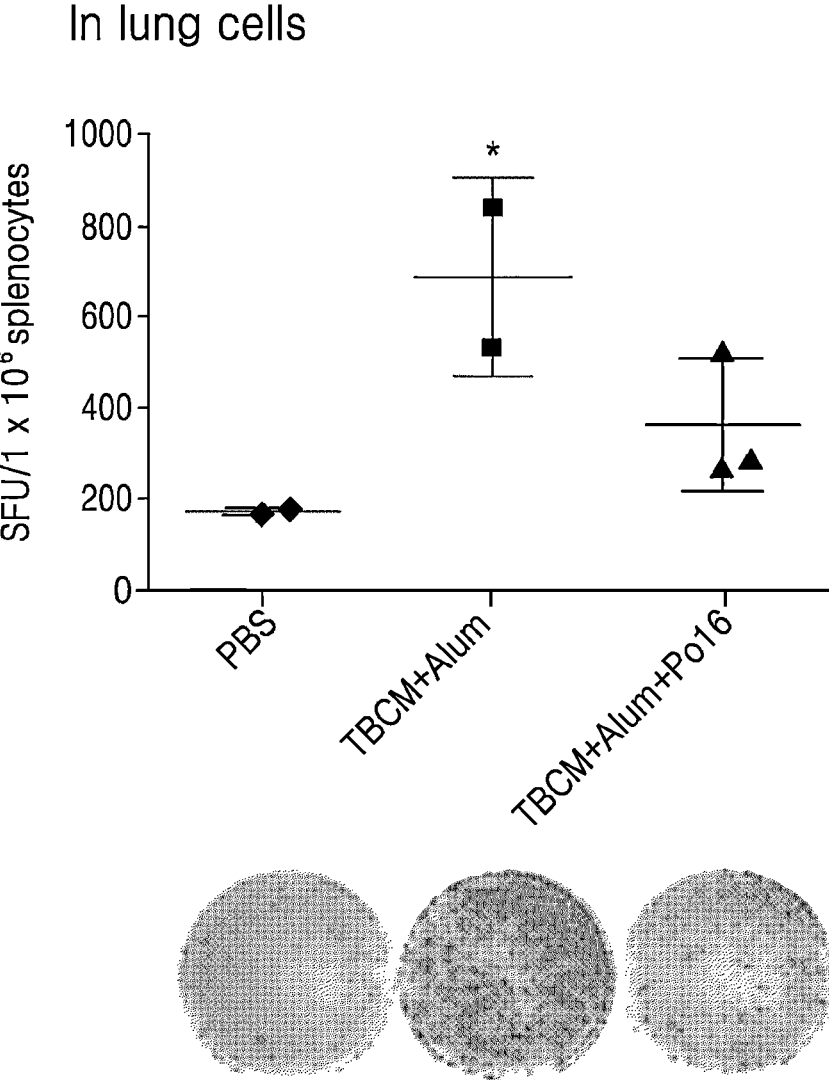
Figure 9A:
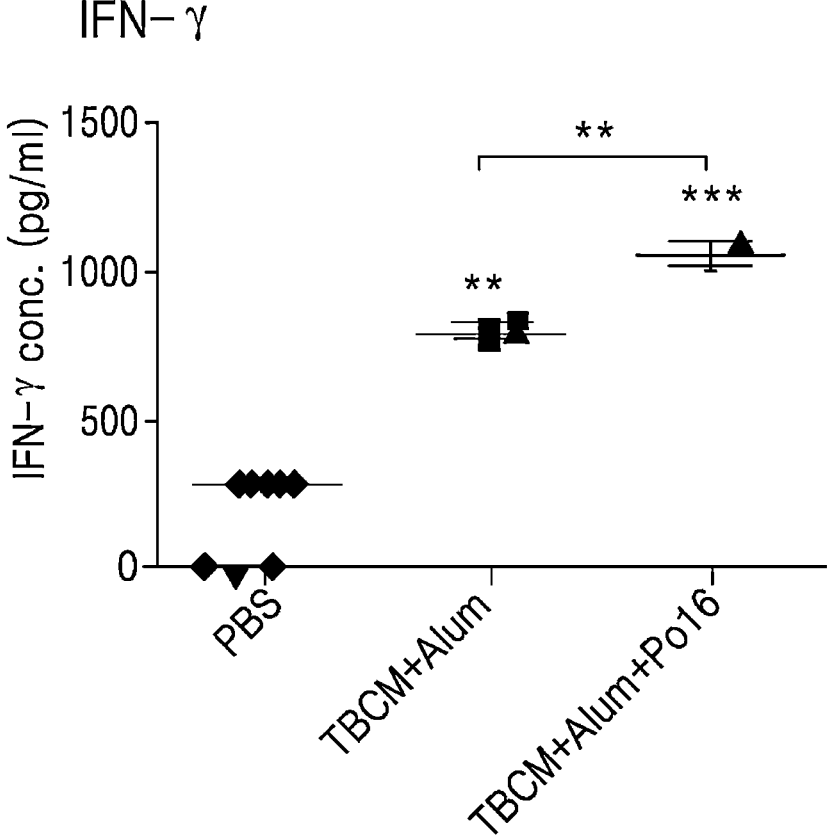
FIG. 9 is a diagram showing data obtained by confirming expression of (A) IFN-γ, (B) IL-12, (C) IL-17, and (D) IL-10 cytokines in a cell medium by ELISA when splenocytes obtained by immunization (intranasal (IN) route) with a combination of TBCM and Alum or additionally Pol6 (statistical significance is tested by Student-t-test, *, P<; 0.05; , P<; 0.01; and *, P<0.001).
Figure 9B:
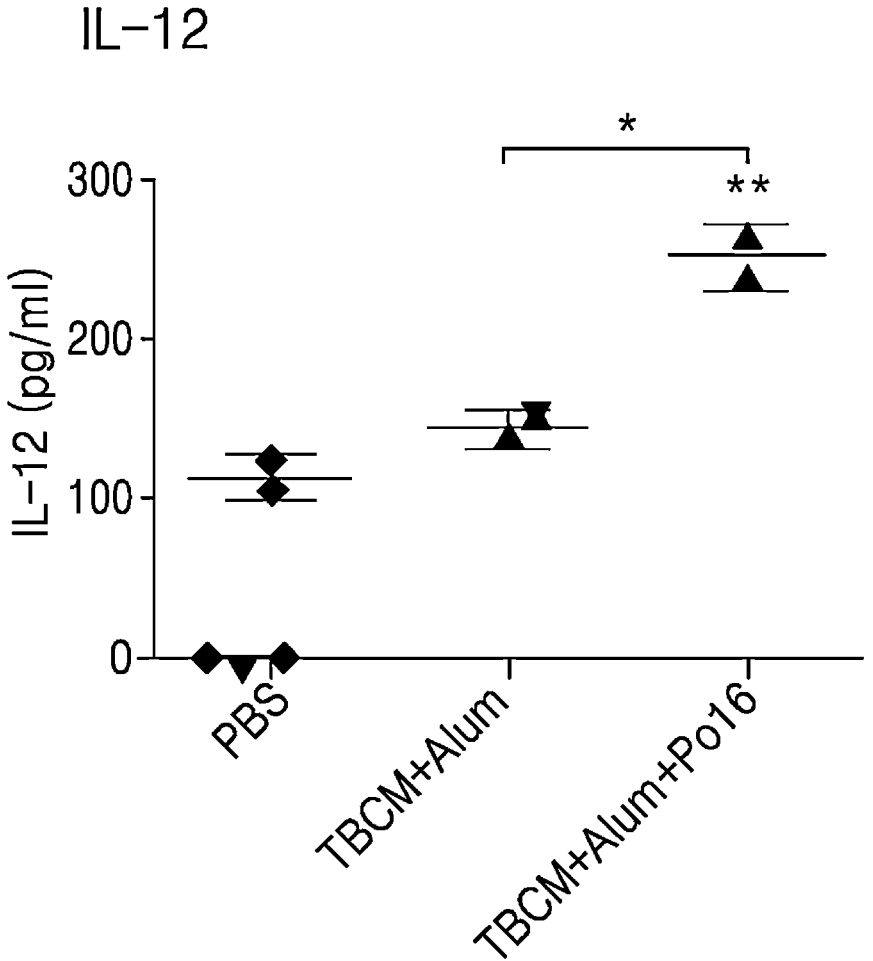
Figure 9C:
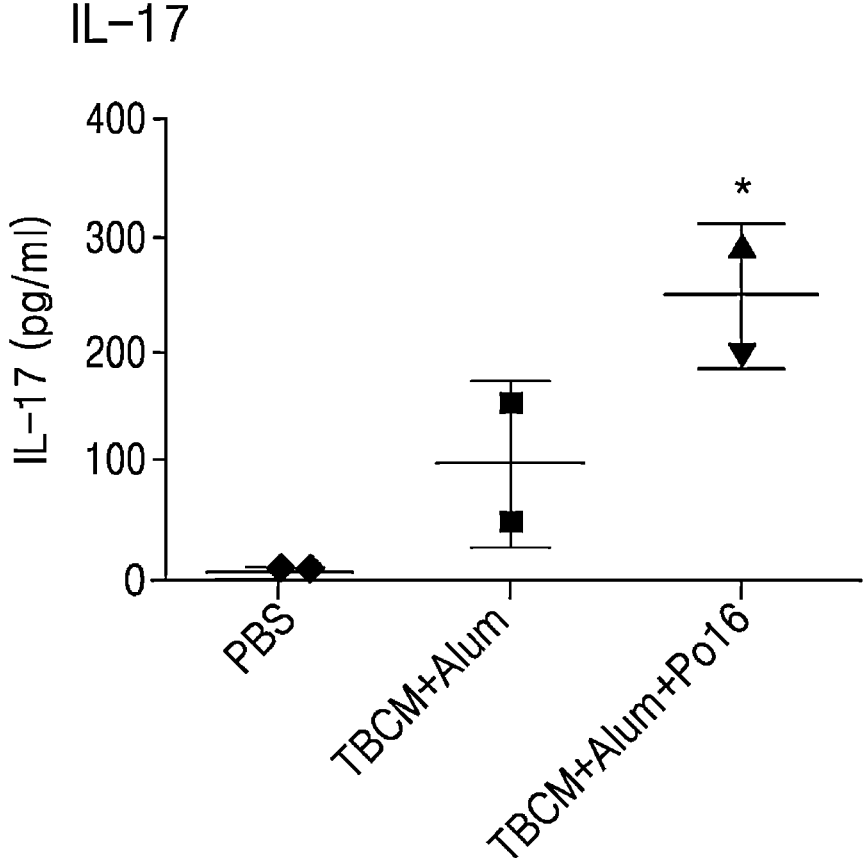
Figure 9D:
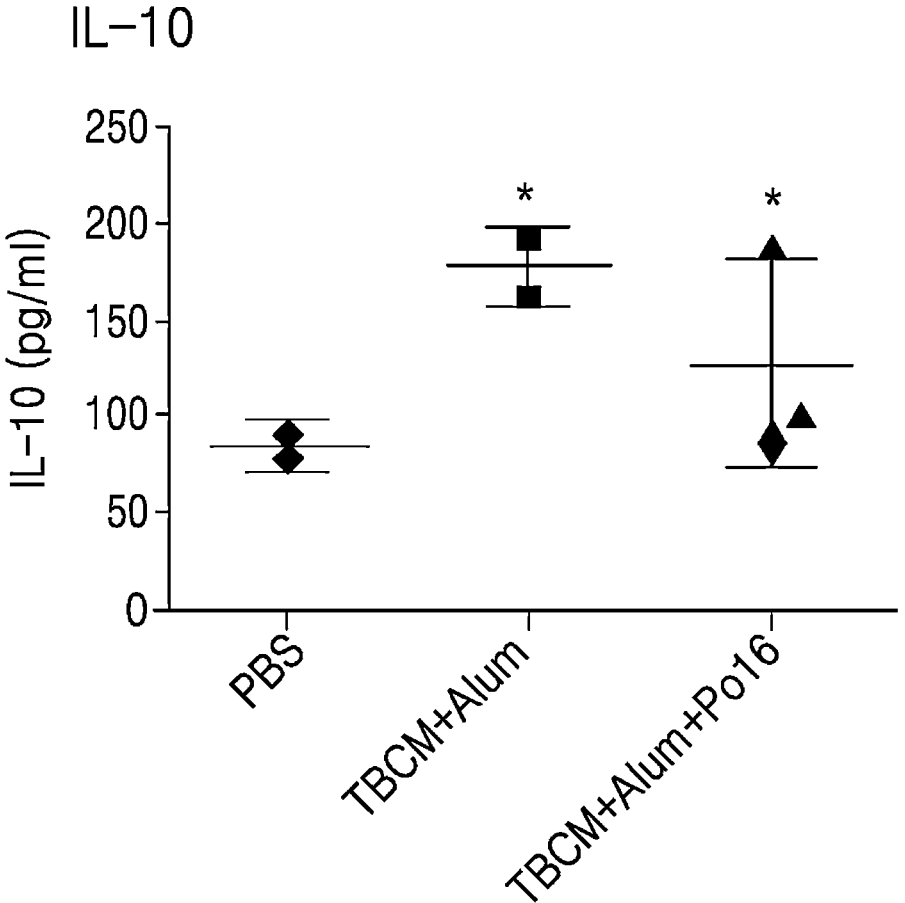
Figure 10A:
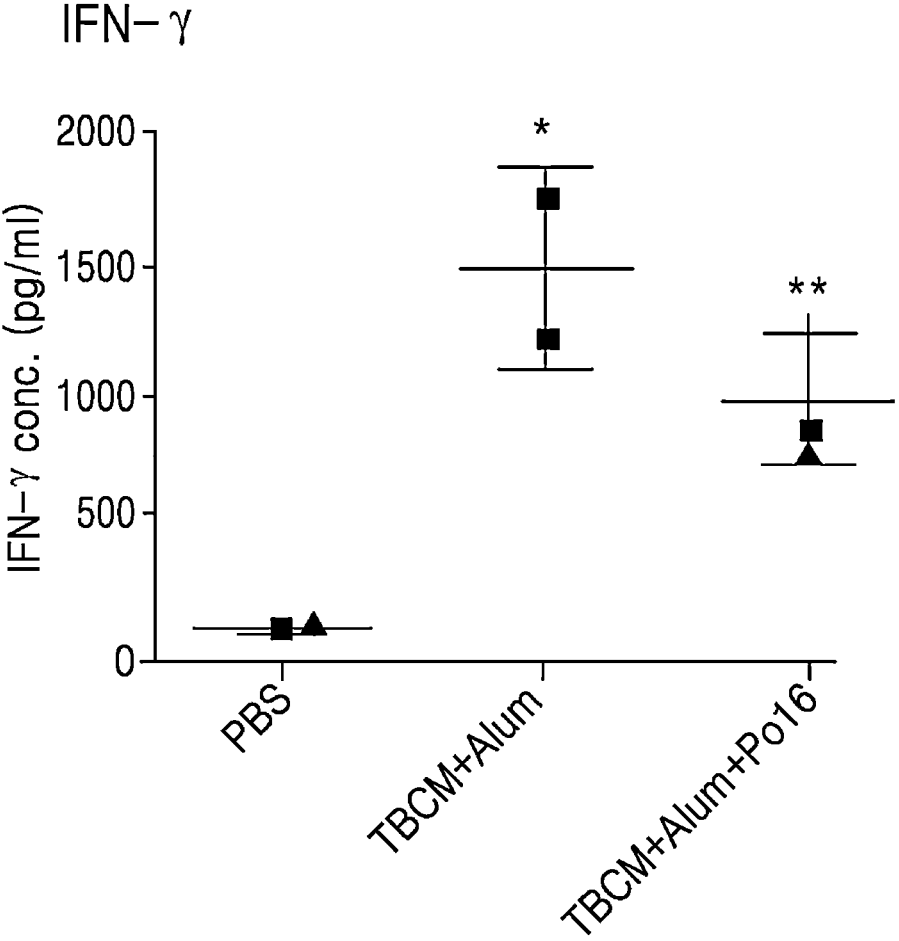
FIG. 10 is a diagram showing data obtained by confirming expression of (A) IFN-γ, (B) IL-12, (C) IL-17, and (D) IL-10 cytokines in a cell medium when pneumocytes obtained by immunization (IN route) with a combination of TBCM and Alum or additionally Pol6 (statistical significance is tested by Student-t-test, *, P<; 0.05; , P<; 0.01; and *, P<0.001).
Figure 10B:
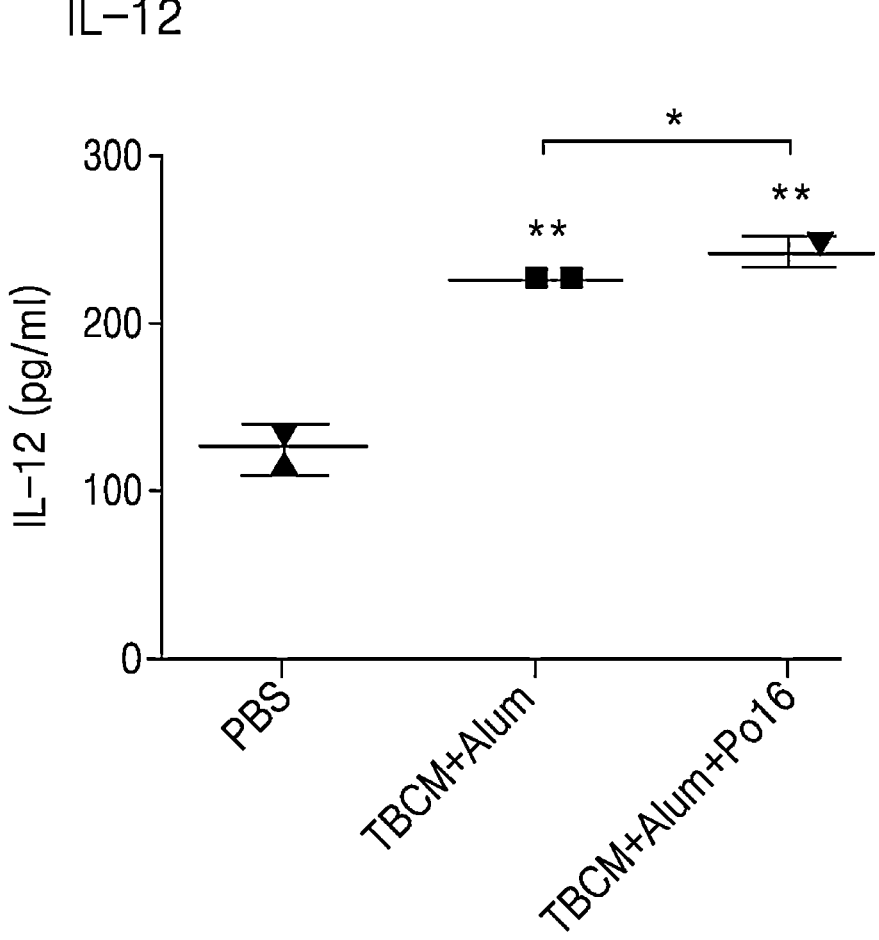
Figure 10C:
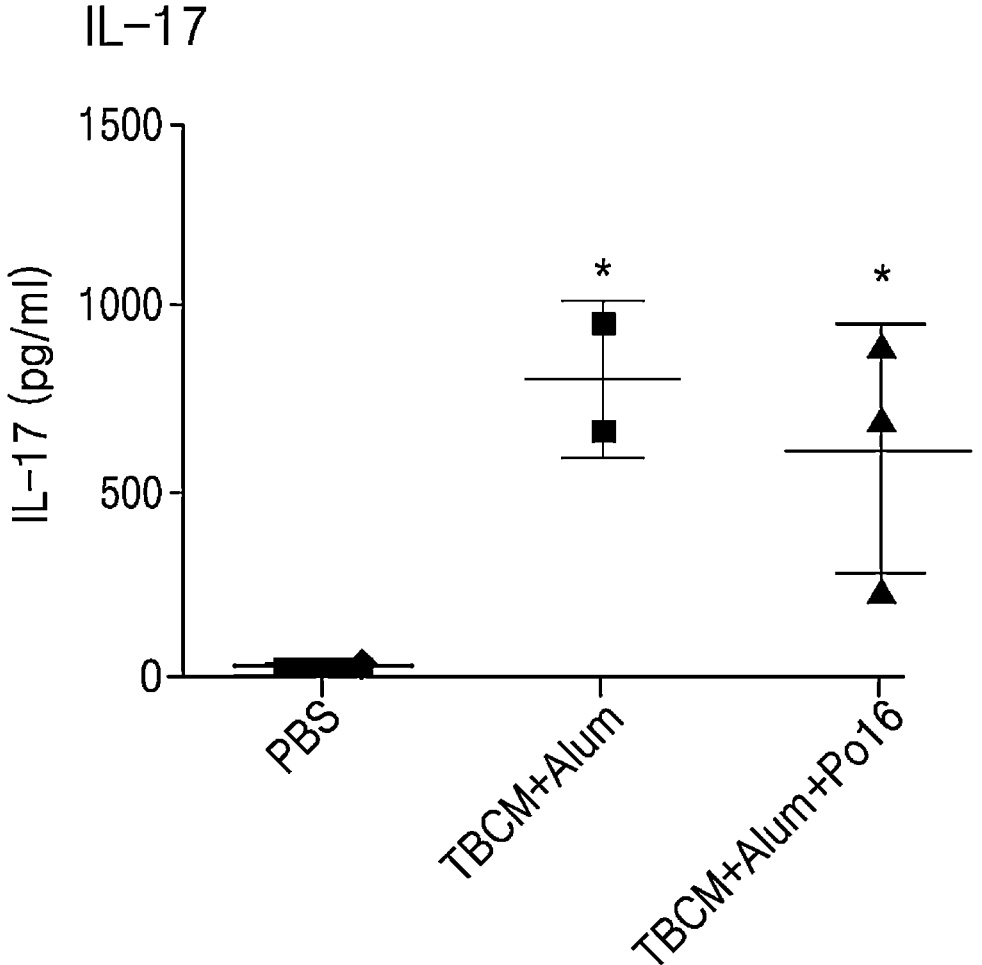
Figure 10D:
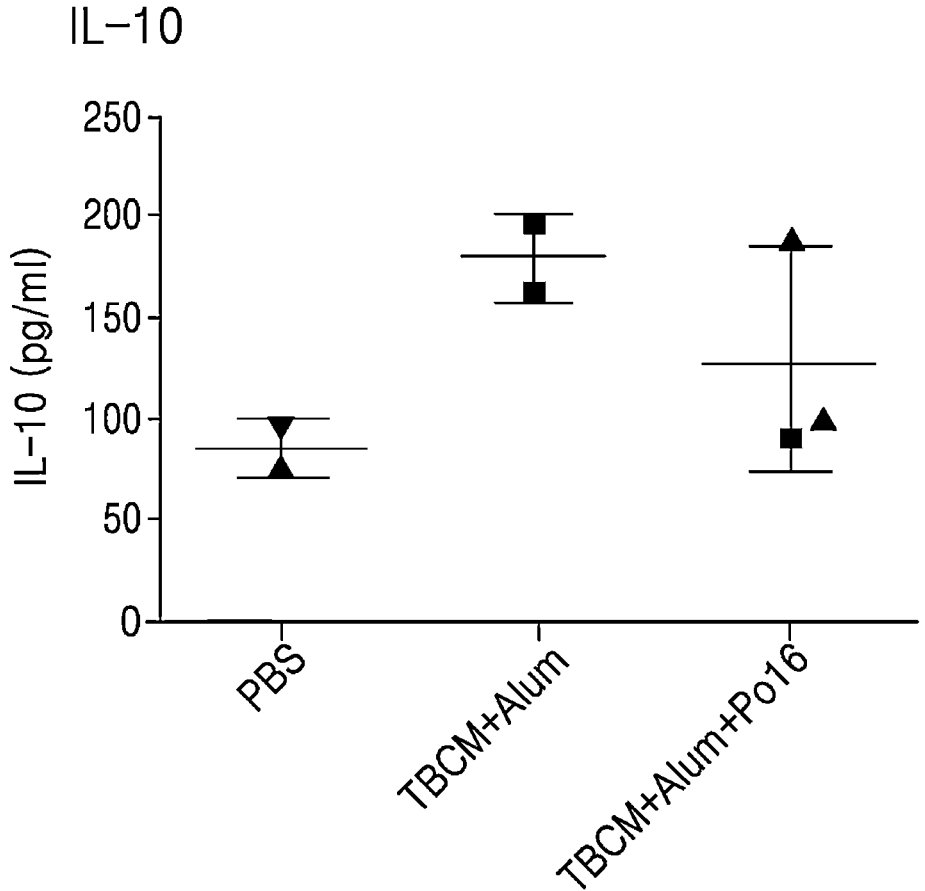

As a result, it was confirmed that IFN-γ specific to TBCM was increased in all cells by immunization with TBCM+Alum or TBCM+Alum+Pol6 compared to a PBS group. However, IFN-γ was produced the most in splenocytes of a group immunized with TBCM+Alum+Pol6 and in pneumocytes of a group immunized with TBCM+Alum (FIG. 8).

2) Measurement of Cytokines

After splenocytes and pneumocytes of mice immunized with a combination of TBCM and Alum or additionally Pol6 were stimulated with the TBCM protein, ELISA for IFN-γ, IL-12, IL-17, and IL-10 was performed in a cell culture medium. In addition, ELISA for IL-12 was performed in BAL fluid.

As a result, it was confirmed that, in a similar manner as in the results of IFN-γ ELISPOT in splenocytes, the expression levels of IFN-γ, IL-12, and IL-17 in a group immunized with TBCM+Alum+Pol6 were increased with statistical significance, compared to a group immunized with TBCM+Alum (FIG. 9). It was also confirmed that, in pneumocytes, the expression levels of IFN-γ and IL-17 in a group immunized with TBCM+Alum was increased compared to a group immunized with TBCM+Alum+Pol6, but there was no statistical significance (FIG. 10).

Regarding IL-10 which is an anti-inflammatory cytokine, the highest expression of IL-10 was shown in both splenocytes and pneumocytes upon immunization with a combination of TBCM+Alum (FIGS. 9 and 10).

Figure 11:
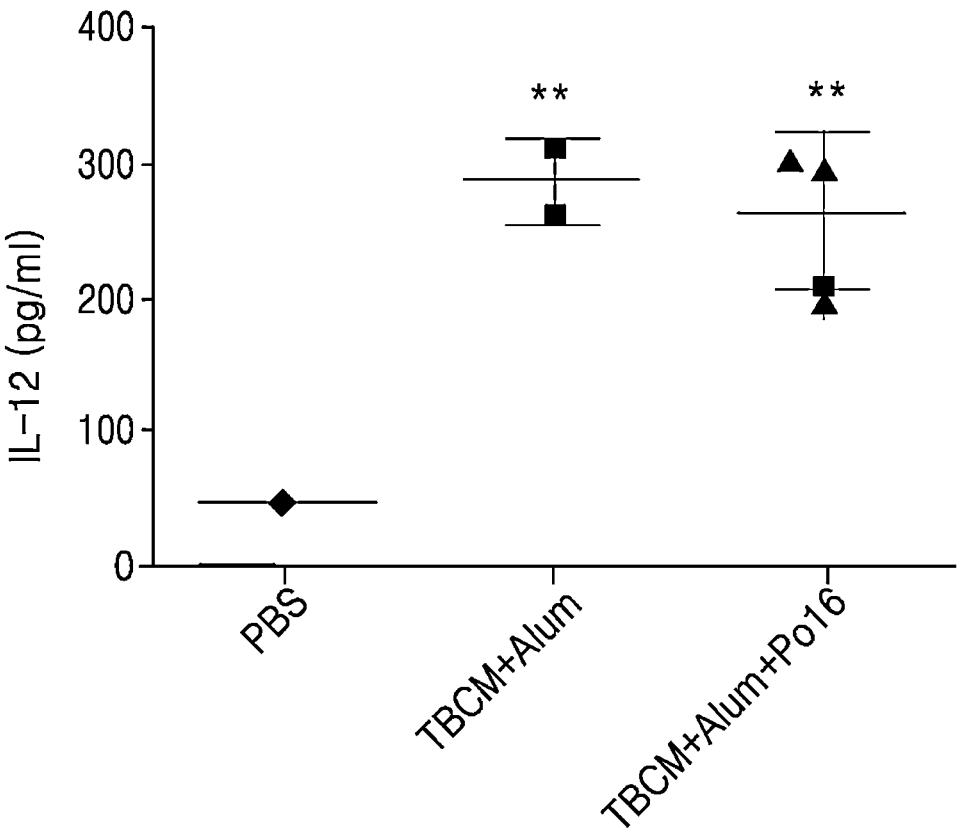
FIG. 11 is a diagram showing the result of confirming an expression level of IL-12 in bronchoalveolar lavage (BAL) fluid by ELISA after immunization (IN route) with a combination of TBCM and Alum or additionally Pol6 (statistical significance is tested by Student-t-test, **, P<0.01).
Figure 12A:
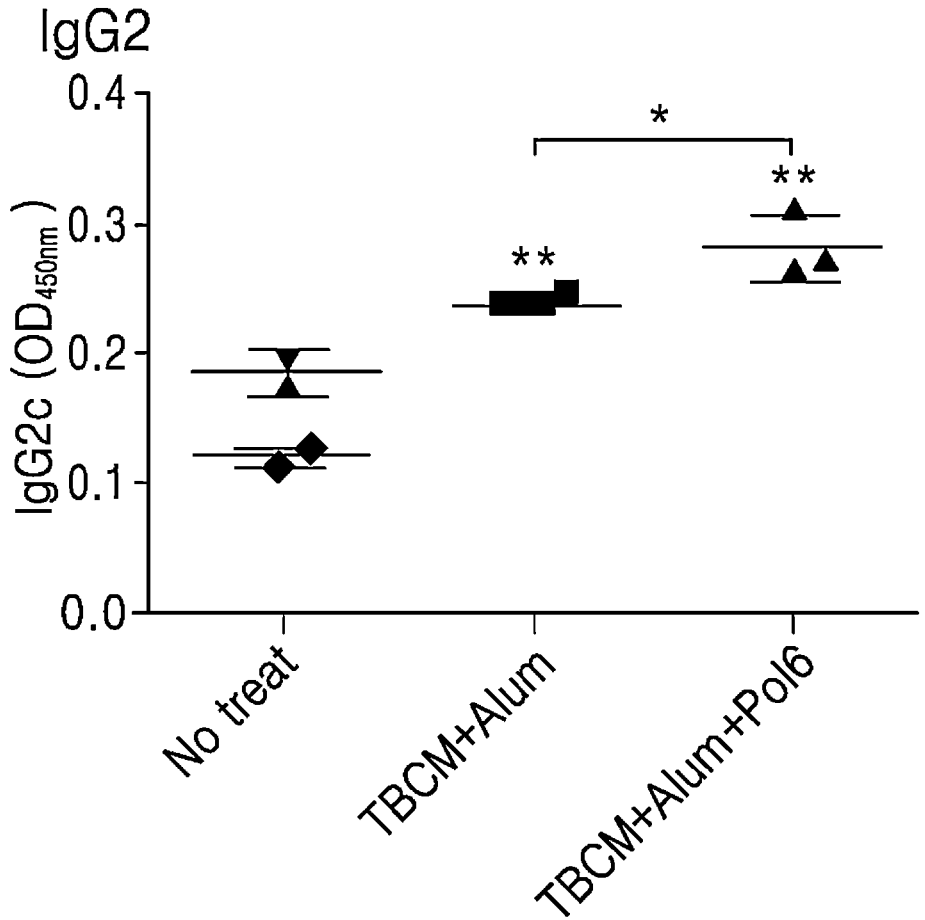
FIG. 12 is a diagram showing data obtained by confirming expression of (A) IgG2, (B) IgG1, (C) total IgG, and (D) IgA in serum and BAL fluid by ELISA after immunization (IN route) with a combination of TBCM and Alum or additionally Pol6 (statistical significance is tested by Student-t-test, *, P<; 0.05; , P<; 0.01; and *, P<0.001).
Figure 12B:
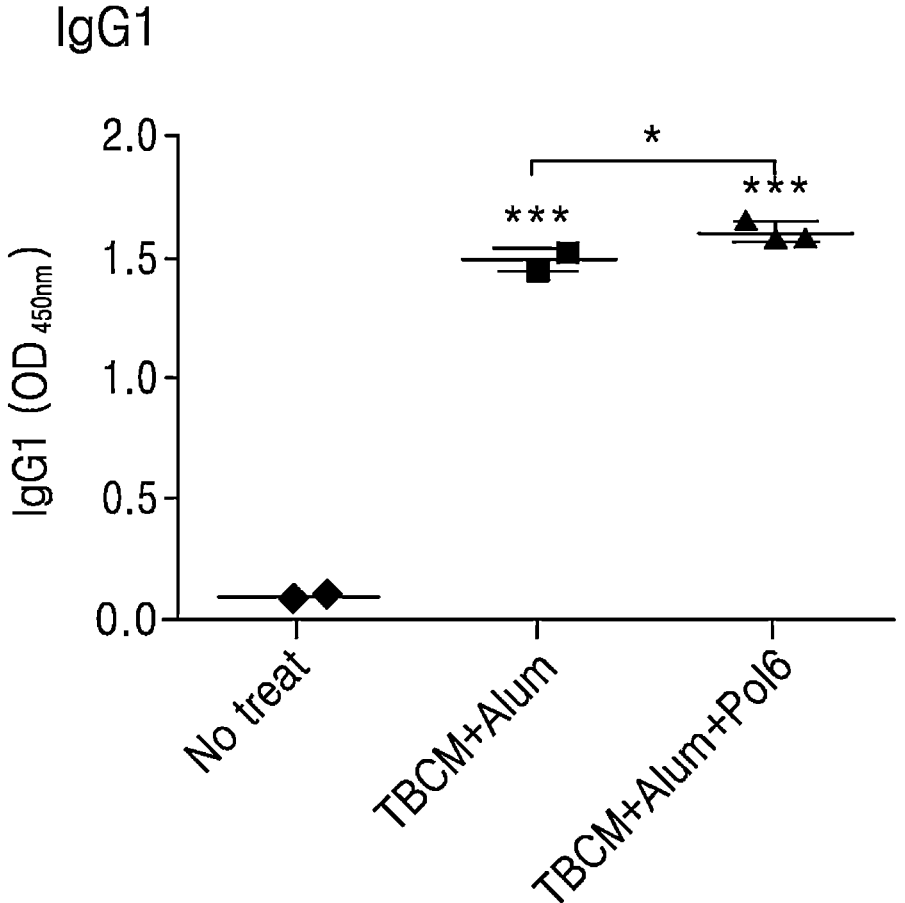
Figure 12C:
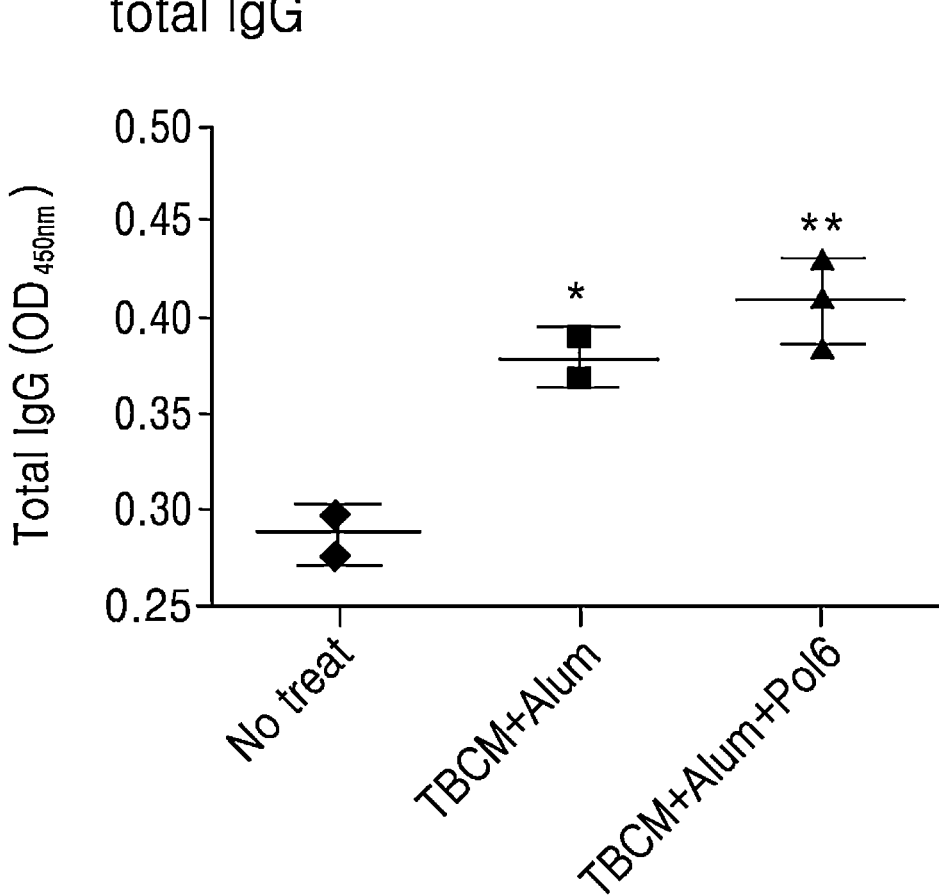
Figure 12D:
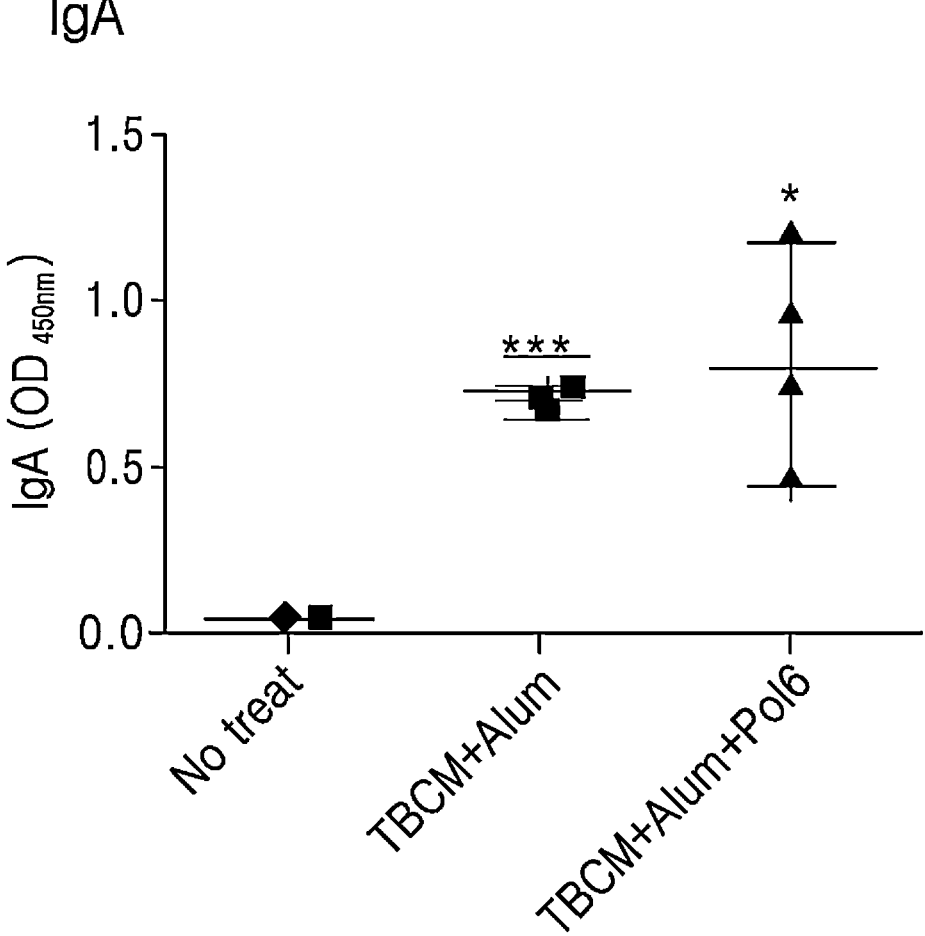

In addition, only the expression level of IL-12 was confirmed in BAL fluid, whereas the expression of IL-12 was increased at a statistically significant level in both groups immunized with a combination of TBCM+Alum and a combination of TBCM+Alum+Pol6, respectively, compared to a PBS group. However, there was no difference between the two groups (FIG. 11).

3) Measurement of IgG and IgA in Serum and BAL Fluid

IgG2, IgG1, total IgG, and IgA specific to TBCM in serum and BAL fluid of mice immunized with a combination of TBCM and Alum or additional Pol6 were evaluated by ELISA.

The expression of IgG2, IgG1, and total IgG in serum increased in both groups immunized with a combination of TBCM+Alum and a combination of TBCM+Alum+Pol6, respectively, but showed a relatively higher expression pattern in a group immunized with a combination of TBCM+Alum+Pol6 (FIG. 12). In addition, in the case of IgA which plays an important role in mucosal immunity, the expression of IgA increased in both immunized groups in the BAL fluid (FIG. 12).

Figure 13:
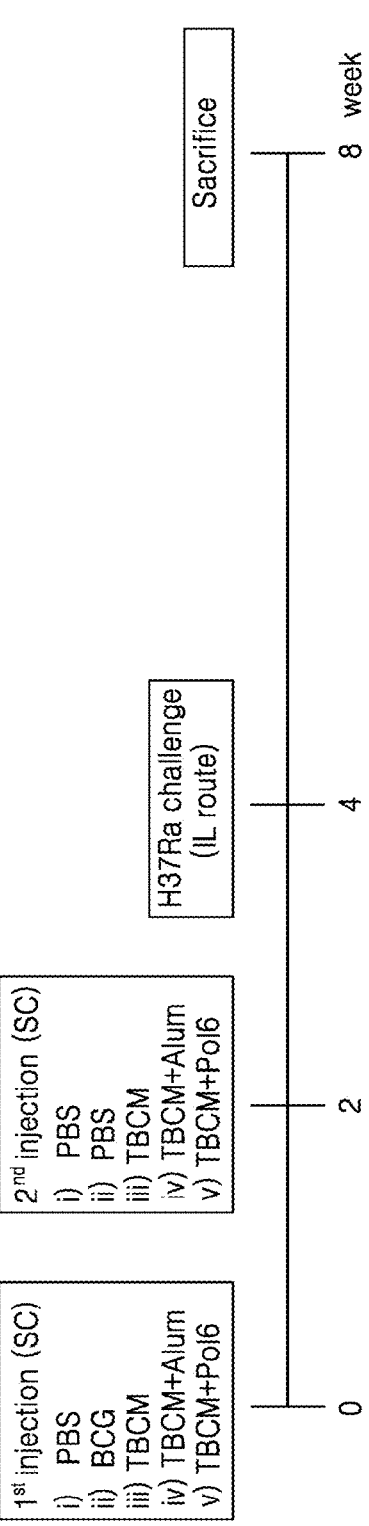
FIG. 13 is a diagram showing an immunization schedule of mouse through a combination of TBCM and various adjuvants. In detail, a BCG-immunized group is selected as a comparative group, and after completion of the immunization, a mouse was sacrificed 4 weeks after H37Ra infection (IN) to observe immune responses, measure colony forming unit (CFU) in organs and proceed hematoxylin and eosin (H&E) staining in lung tissue.

(3) Evaluation of Ability for Tuberculosis Defense Induction by Immunization with TBCM Protein and Pol6 in Combination After mice were immunized (by SC injection) twice at 2-week intervals with a combination of TBCM and various adjuvants (TBCM alone, TBCM+Alum, TBCM+Pol6, and TBCM+Alum+Pol6) according to the schedule shown in FIG. 13, the mice were infected (by IN injection) with a H37Ra strain. After the mice were sacrificed 4 weeks after the infection, immune responses specific to TBCM and the tuberculosis antigen Ag85B in splenocytes and serum were observed, and the number of H37Ra bacteria (CFU) in organs and the inflammatory response patterns in lung tissue were confirmed by H&E staining. A BCG-immunized (by SC injection) group was selected as a comparative group. The concentrations of TBCM protein and adjuvants used for the immunization and the number of BCG bacteria were as follows:

i) TBCM (10 µg/mouse);
    ii) Alum (100 µg/mouse);
    iii) Pol6 (5 µg/mouse); and
    iv) BCG ($1 \times 10^6$ CFU/mouse).

1) Measurement of Cytokines

After splenocytes of mice immunized with a combination of respective protein and adjuvant and infected with H37Ra were stimulated with TBCM and Ag85B proteins, respectively, and ELISA for IFN-γ, IL-12, TNF-α, and IL-10 in cell culture medium was performed.

As a result, upon stimulation with TBCM, it was confirmed that the IFN-γ expression increased with statistical significance by immunization with a combination of TBCM+Pol6 compared to cases immunized with BCG, TBCM alone, and a combination of TBCM+Alum. Meanwhile, upon stimulation with Ag85B, it was confirmed that the IFN-γ expression increased by immunization with a combination of TBCM+Alum compared to cases immunized with BCG, TBCM alone, and a combination of TBCM+Pol6.

Figure 14A:
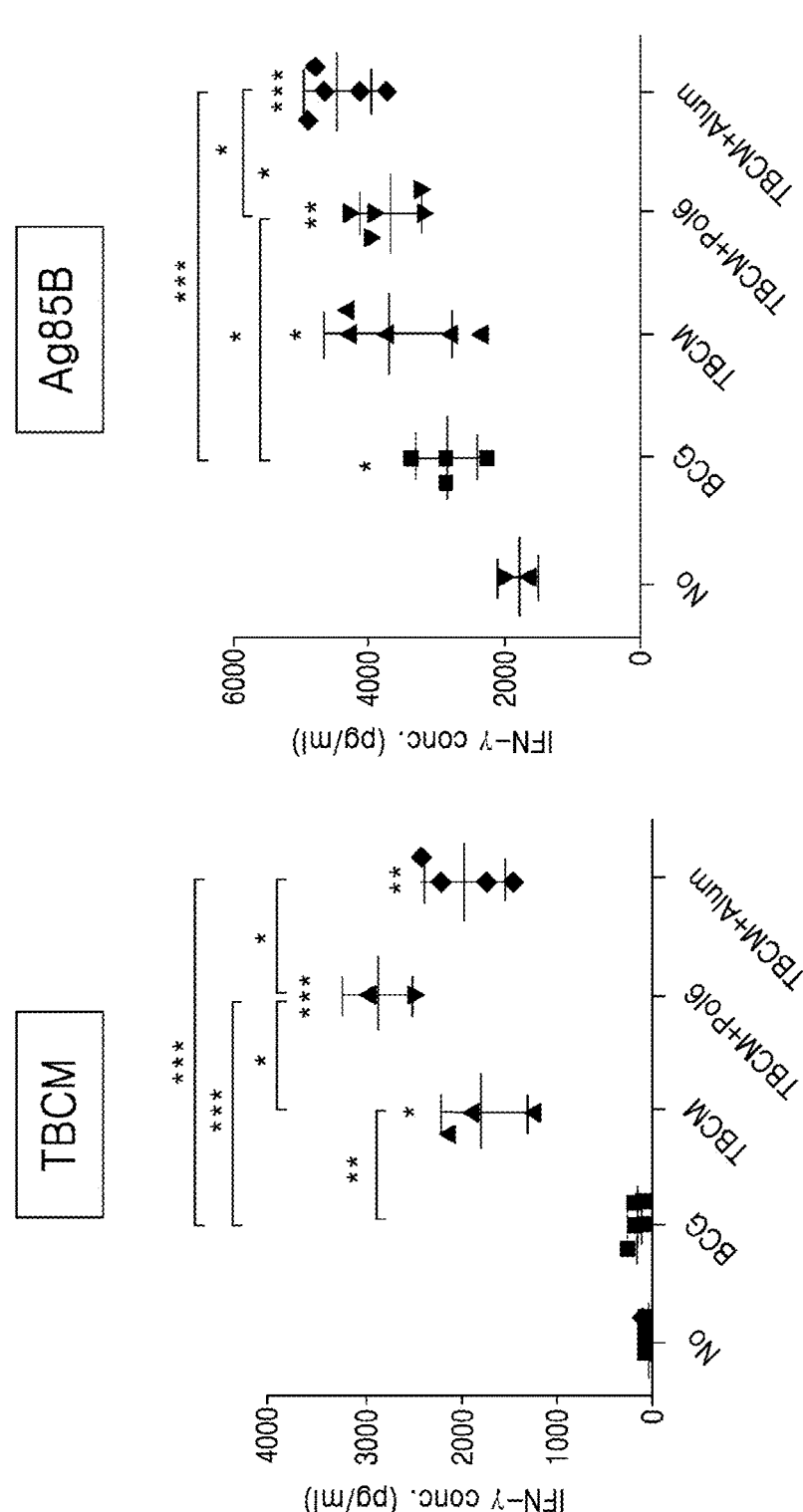
FIGS. 14 and 15 show results confirming expression of IFN-γ (FIG. 14A), IL-12 (FIG. 14B), TNF-α (FIG. 15A), and IL-10 (FIG. 15B) in a cell medium by ELISA when splenocytes obtained by immunizing with a combination of TBCM and various adjuvants and infecting H37Ra are stimulated with TBCM and Ag85B proteins (statistical significance is tested by Student-t-test, *, P<0.05; , P<0.01; and *, P<0.001).
Figure 14B:
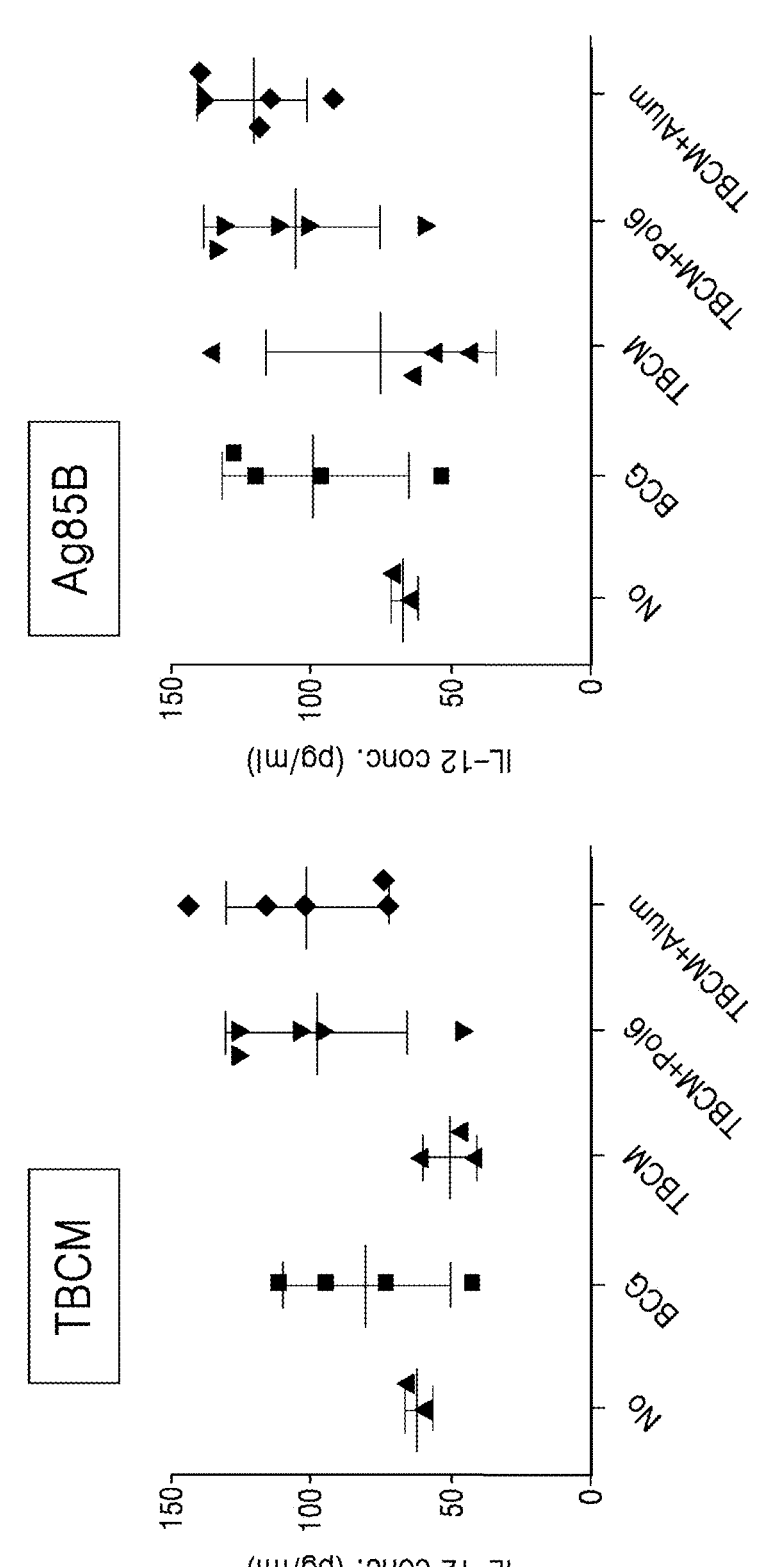

Regarding IL-12 upon stimulation with TBCM and Ag85B, respectively, cases immunized with a combination of TBCM+Pol6 and a combination of TBCM+Alum showed the IL-12 expression at almost the same level compared to other immunized groups (FIG. 14B).

Figure 15A:
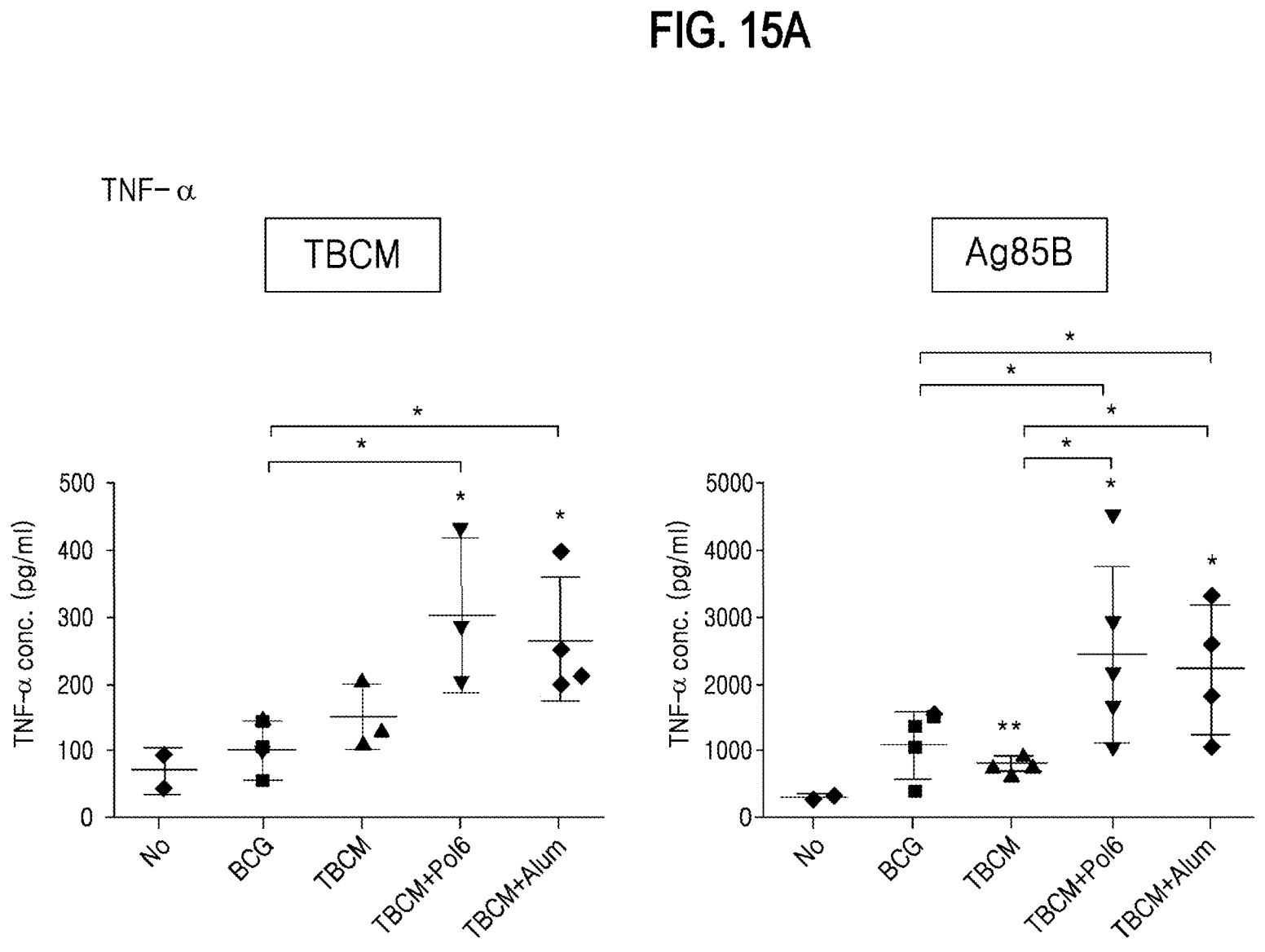

Regarding TNF-α in a similar manner as in the trend of IL-12, cases immunized with a combination of TBCM+Pol6 and TBCM+Alum showed increased IL expression compared to other immunized groups (FIG. 15A).

Figure 15B:
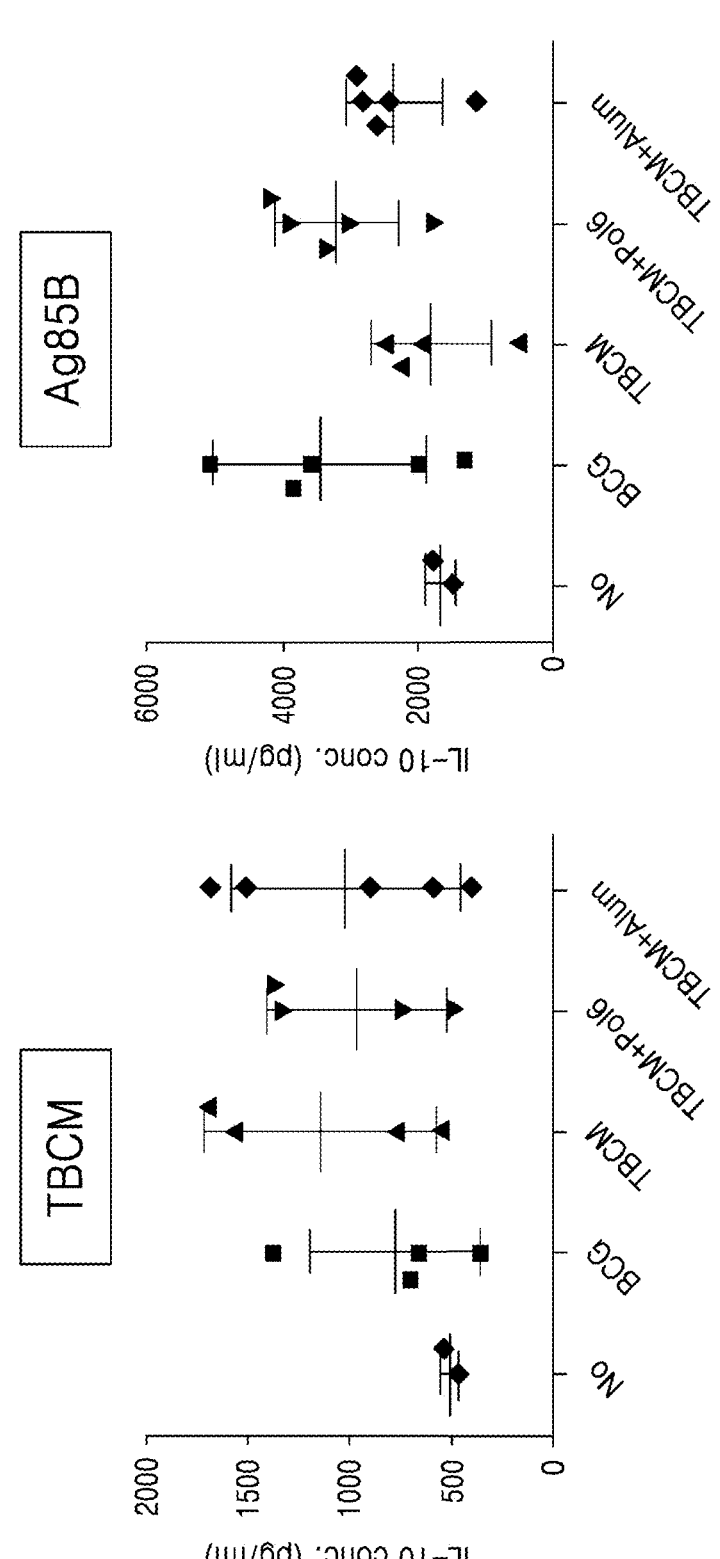
Figure 16A:
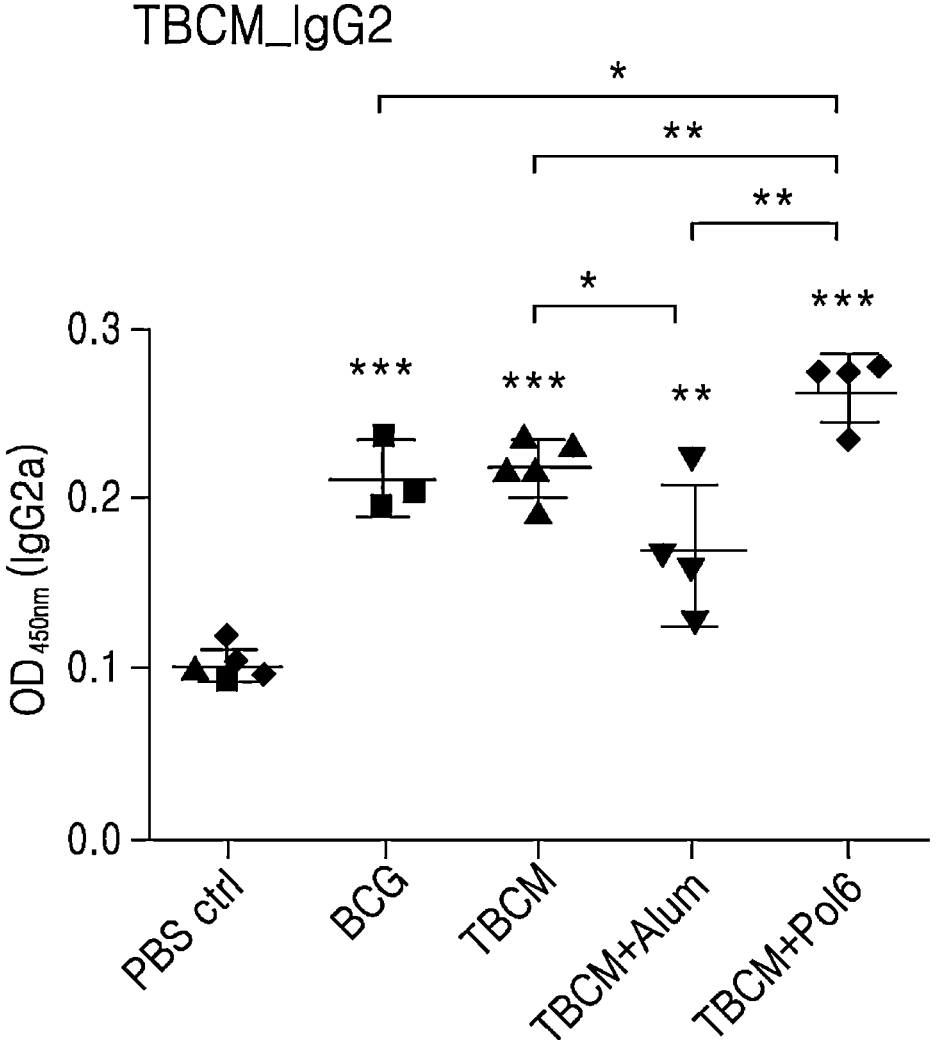
FIG. 16 shows results confirming expression of IgG2 (A and D), IgG1 (B and E), and total IgG (C and F) that are specific to TBCM and Ag85B proteins by ELISA in serum obtained by infecting H37Ra after immunization with a combination of TBCM and various adjuvants (statistical significance is tested by Student-t-test, *, P<0.05; , P<0.01; and *, P<0.001).
Figure 16B:
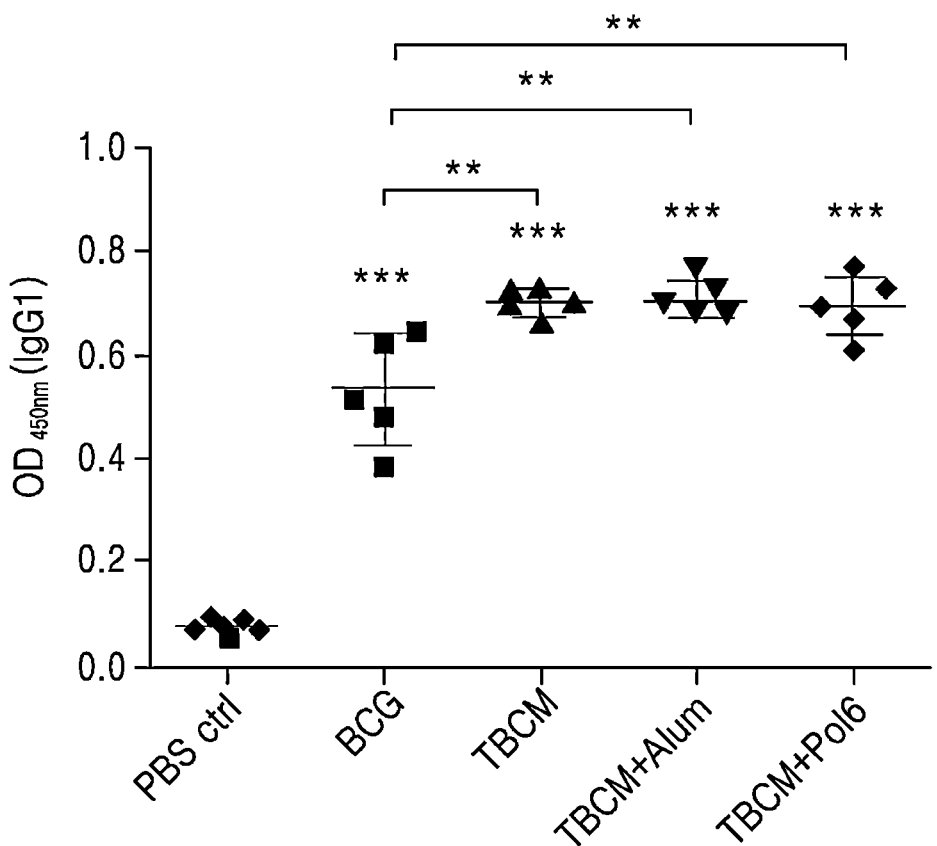
Figure 16C:
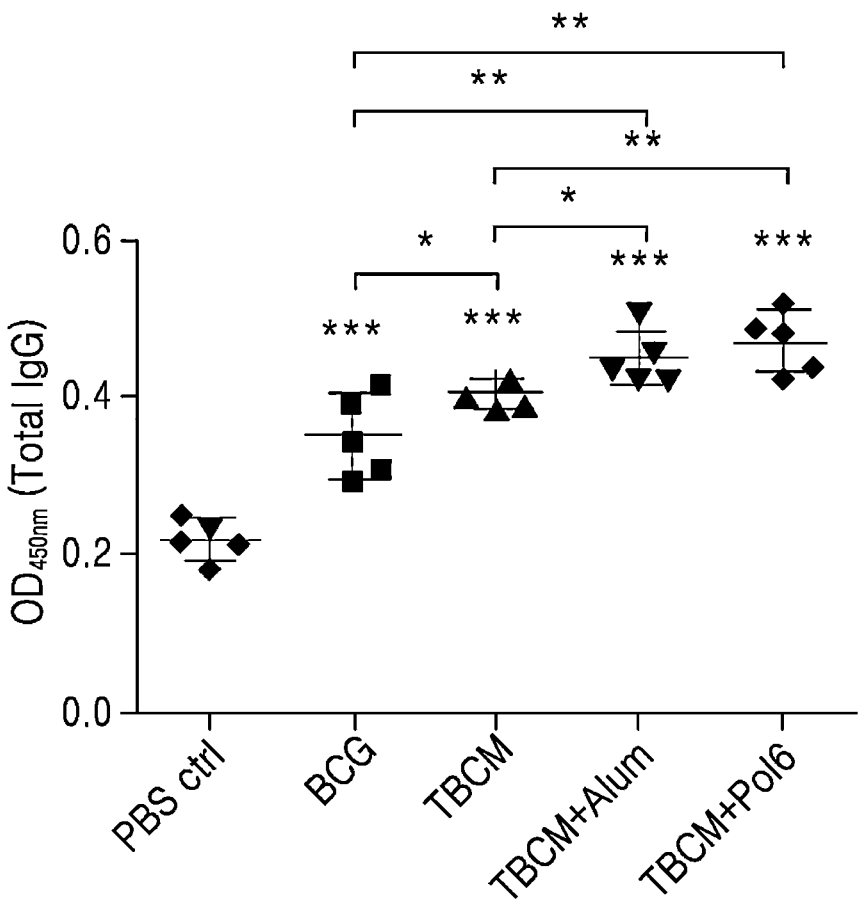
Figure 16D:
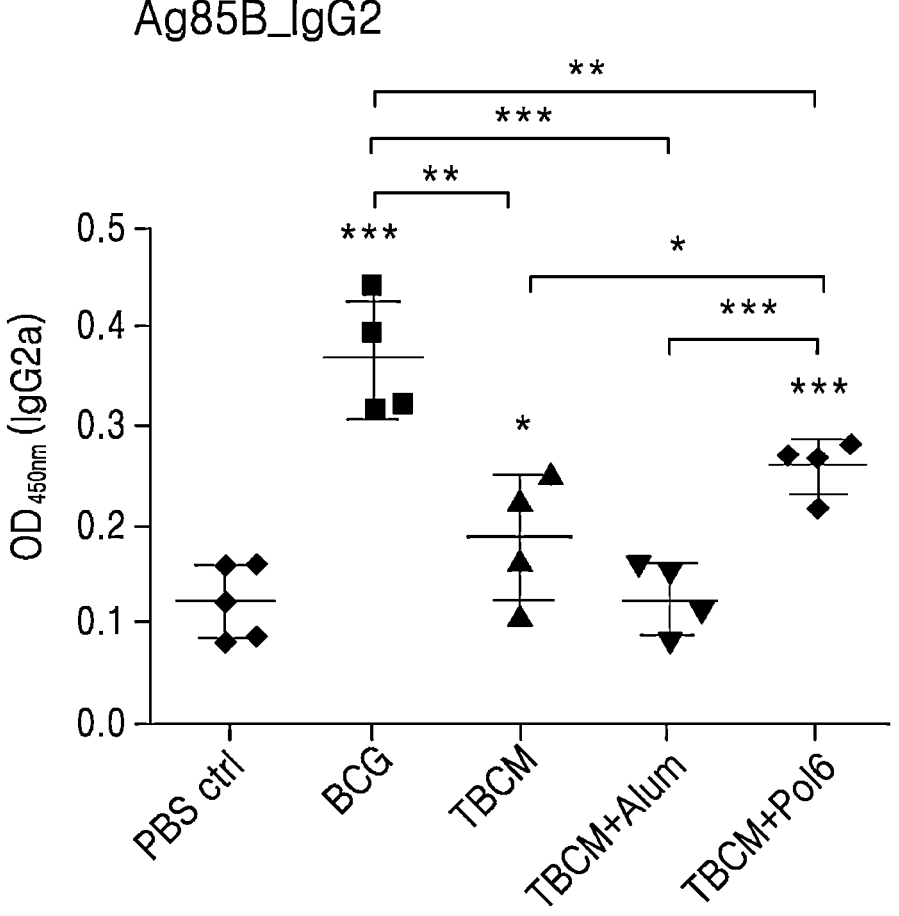
Figure 16E:
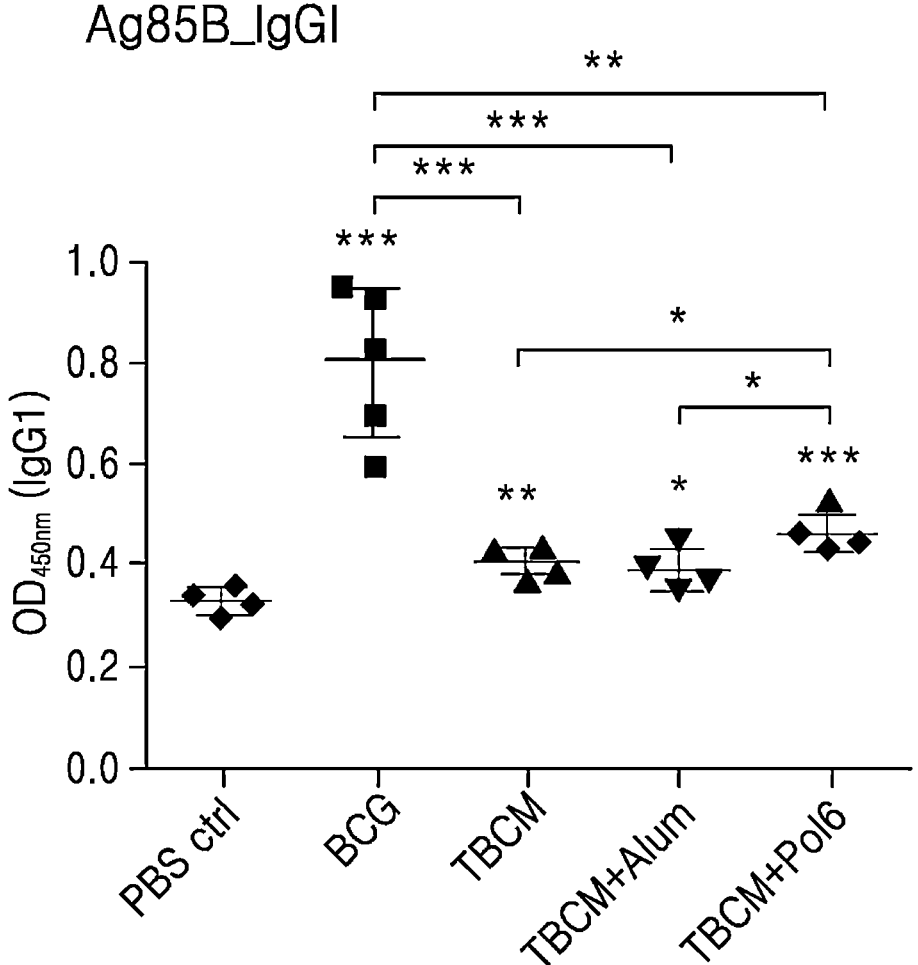
Figure 16F:
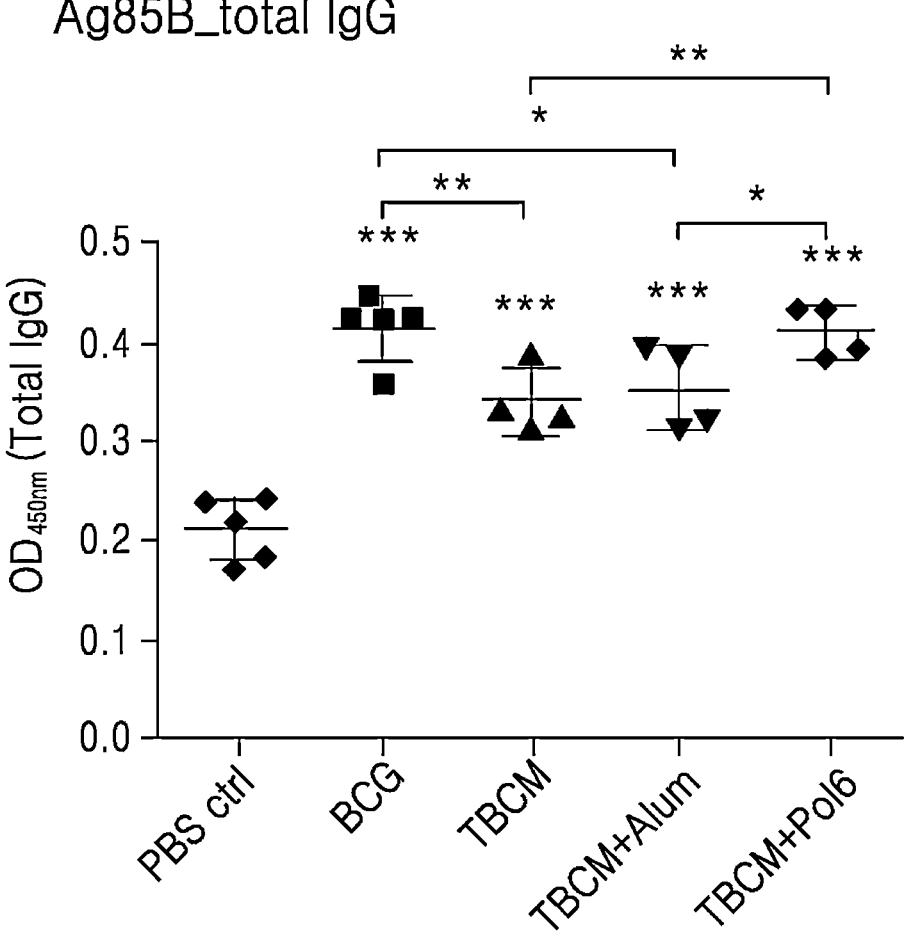

Regarding IL-10 which is an anti-inflammatory cytokine, all immunized groups, except for the non-immunized group, showed similar or no significant differences, probably because the immune response was observed after injection with *M. tuberculosis* (FIG. 15B).

2) Measurement of IgG in Serum

The expression of IgG2, IgG1, and total IgG specific to TBCM and Ag85B proteins in serum of mice immunized with a combination of TBCM protein and adjuvant and infected with *M. tuberculosis* was evaluated and confirmed by ELISA.

As a result, when the TBCM-specific IgG expression pattern was observed, the IgG2 expression by immunization with a combination of TBCM+Pol6 increased with statistical significance compared to other immunized groups. Regarding IgG1, a similar level of expression was observed in other immunized groups except for a BCG-immunized group. Overall, it was confirmed with total IgG that the expression level of TBCM-specific IgG was highest when immunized with a combination of TCM+Pol6, but there was no significance with the results of immunization with a combination of TBCM+Alum (FIG. 16).

When observing the expression pattern of IgG specific to the tuberculosis antigen Ag85B, IgG2 and IgG1 were expressed at the highest level by BCG immunization. It was confirmed that the immunization with a combination of TBCM+Pol6 also induced much expression of IgG2, except for the BCG immunization. In addition, the fact that the expression of Ag85B-specific IgG in the group immunized TBCM+Pol6 was induced to a similar level with the expression in the BCG-immunized group was confirmed by the total IgG results (FIG. 16).

3) Confirmation of CFU in Organs

After mice were immunized with a combination of TBCM and various adjuvants and infected with the H37Ra bacteria (FIG. 13), the mice were sacrificed, and the lungs were homogenized and diluted in PBS at an appropriate dilution factor. A portion of each dilution was spread on a 7H10 solid medium (supplemented with OADC), and then cultured for about 4 weeks in a 5% $CO_2$ incubator at 37° C. Thereafter, the number of grown colonies was confirmed and CFU was calculated.

Figure 17:
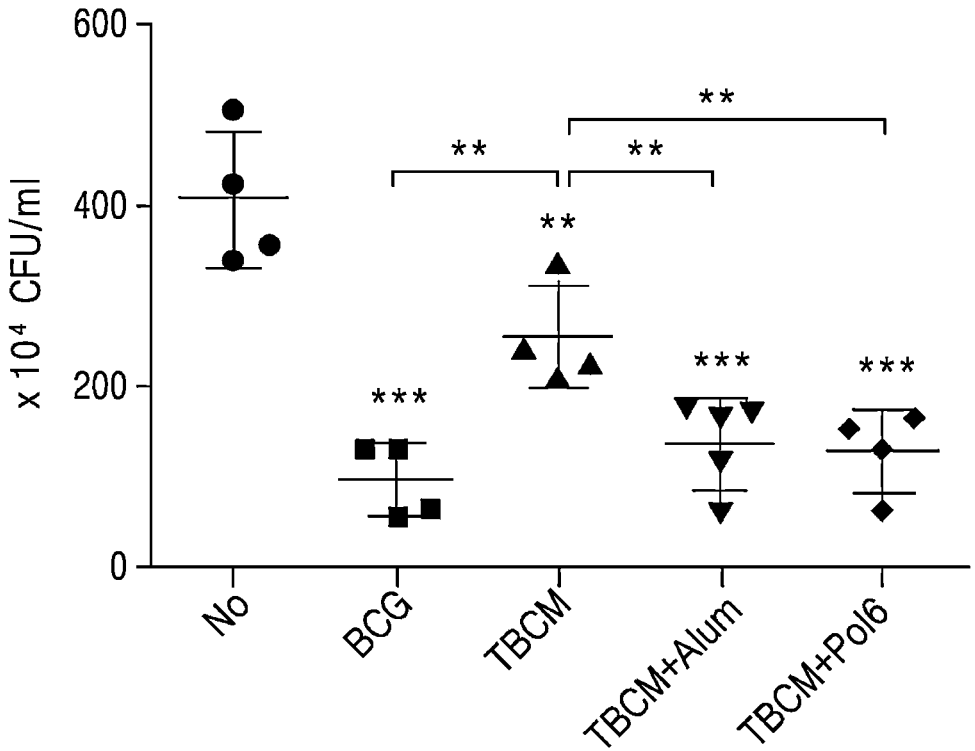
FIG. 17 is a diagram showing the results of comparing the number of H37Ra colonies identified in lungs (statistical significance is tested by Student-t-test, , P<0.01; and *, P<0.001).
Figure 18A:
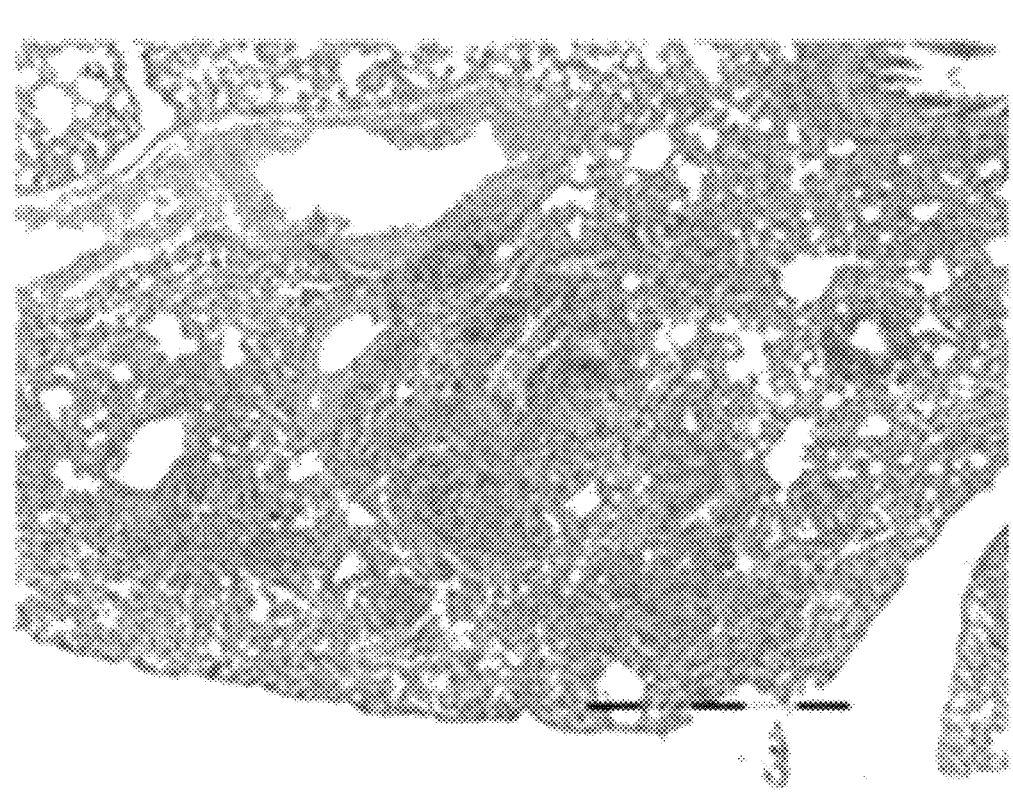
FIG. 18 shows H&E staining photographs of lung tissue of a H37Ra-infected mouse after immunization with a combination of TBCM and various adjuvants.
Figure 18B:
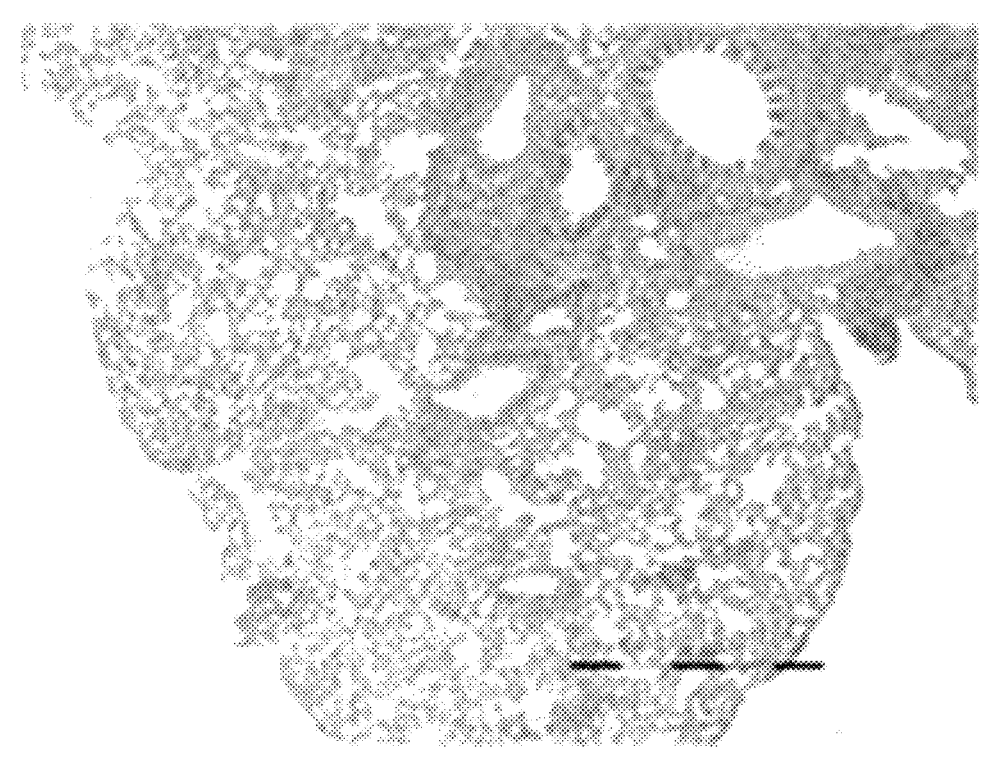
Figure 18C:
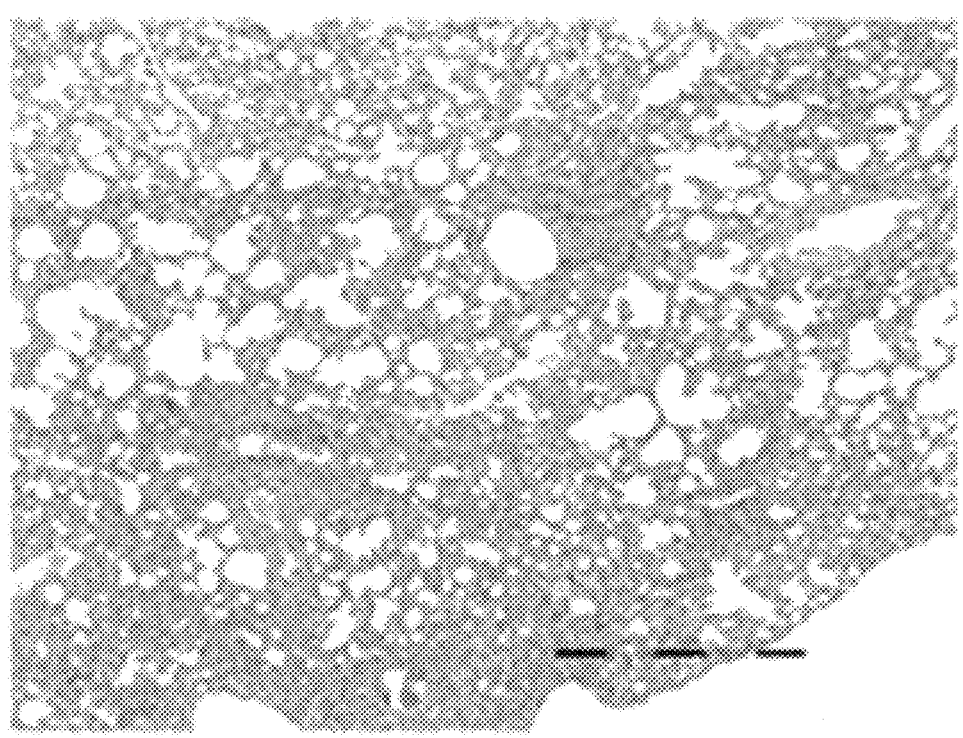
Figure 18D:
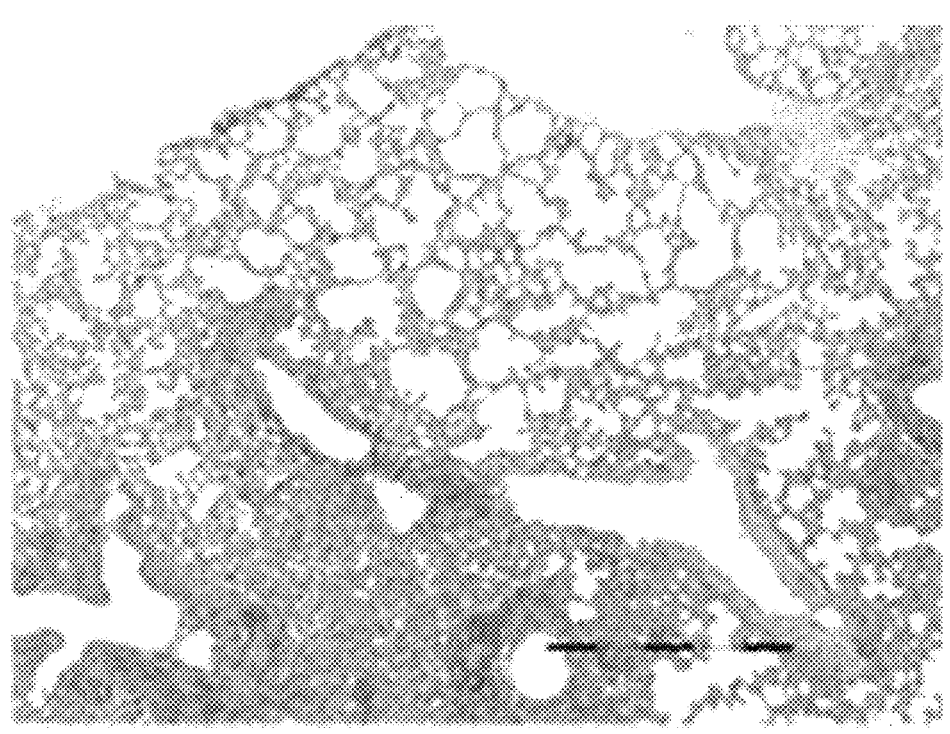
Figure 18E:
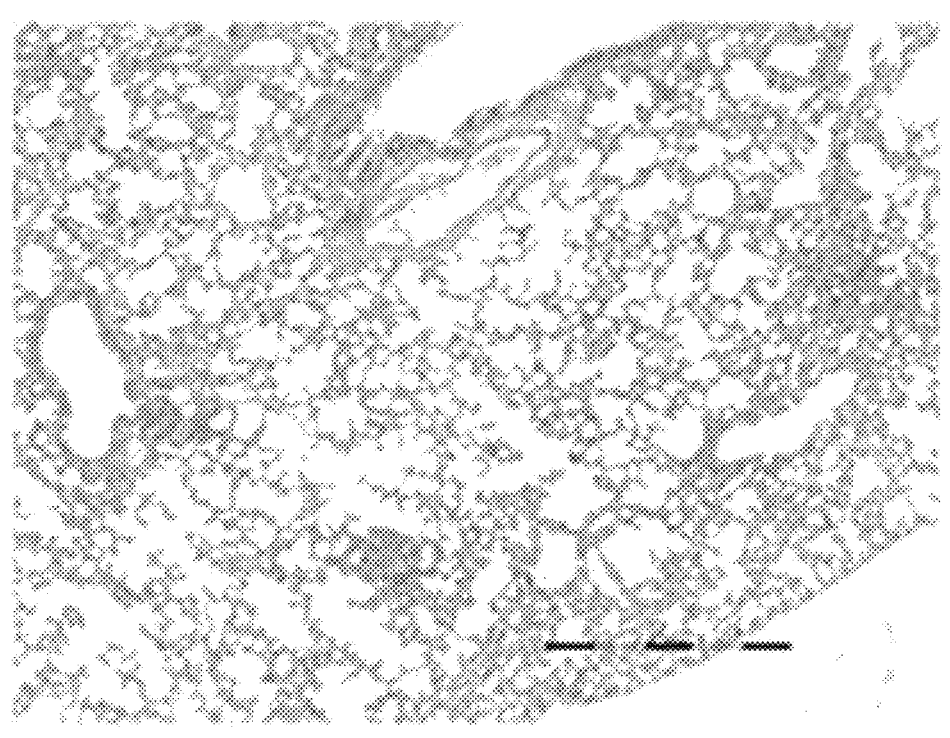

When the CFU was calculated in the lungs, the CFU of all immunized groups was decreased compared to the non-immunized group. The CFU of the groups immunized with BCG, TBCM+Alum showed the lowest pattern, but there was no difference between the groups (FIG. 17). The result of reduced CFU of infected H37Ra at a level similar to BCG which is currently used as a tuberculosis vaccine indicates the possibility of developing a tuberculosis vaccine of TBCM protein.

4) Histopathological Evaluation of Lung Tissue

After mice were immunized with a combination of TBCM and various adjuvants and infected with H37Ra bacteria (FIG. 13), the mice were sacrificed, and a portion of the lungs was fixed with formalin. The fixed samples were embedded in paraffin and subjected to H&E staining. The stained tissue was observed under a microscope to confirm the difference in inflammatory response.

As a result of confirming the H&E staining, the inflammation generally tended to be alleviated in all immunized groups compared to the group infected with H37Ra only (decreased number of cells in tissue, decreased thickness of alveolar septa, etc.), but the degree inflammation relief tended to be the highest in the group immunized with TBCM+Pol6 group (FIG. 18).

5) Evaluation of Cytotoxic T Lymphocyte (CTL) Response

Splenocytes (effector cells) of mice immunization with a combination of TBCM and various adjuvants and infected with H37Ra and P815 cells (H-2d, target cells) stimulated with Ag85B and TBCM proteins were cultured together for 6 hours. Afterwards, the cytotoxicity evaluation was conducted by measuring the amount of lactate dehydrogenase (LDH) exposed in the cell culture medium.

Figure 19A:
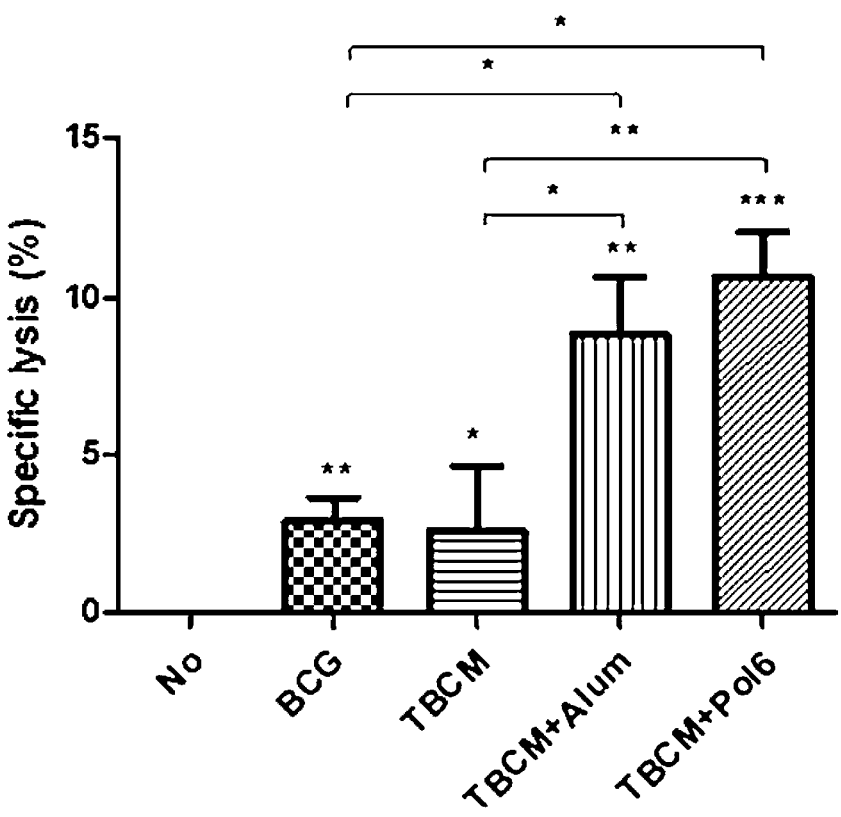
FIG. 19A shows TBCM specific lysis.
Figure 19B:
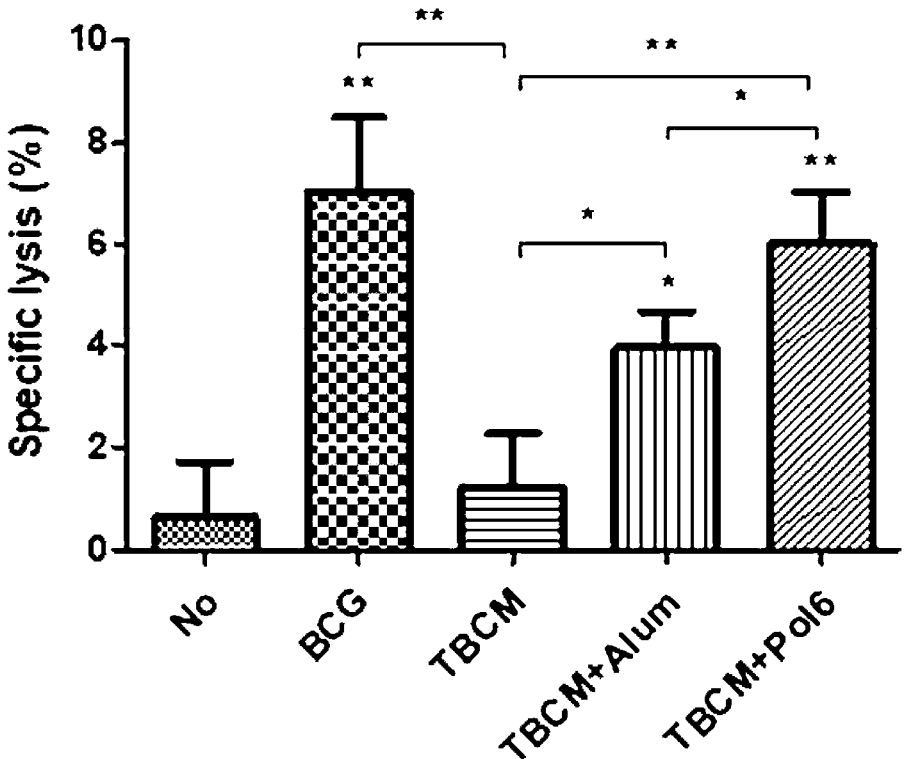
FIG. 19B shows Ag85B specific lysis (statistical significance is tested by Student-t-test,, P<0.01, *, P<0.001).

As a result, it was confirmed that the CTL response to TBCM was increased by the immunization with a combination of TBCM+Alum and a combination of TBCM+Pol6, and that the CTL response to Ag85B was the highest in the BCG-immunized group, but Ag85B-specific cell lysis in the group immunized with TBCM+Pol6 was higher than in other immunization groups (groups immunized with TBCM alone and TBCM+Alum) (FIG. 19).

Figure 20A:
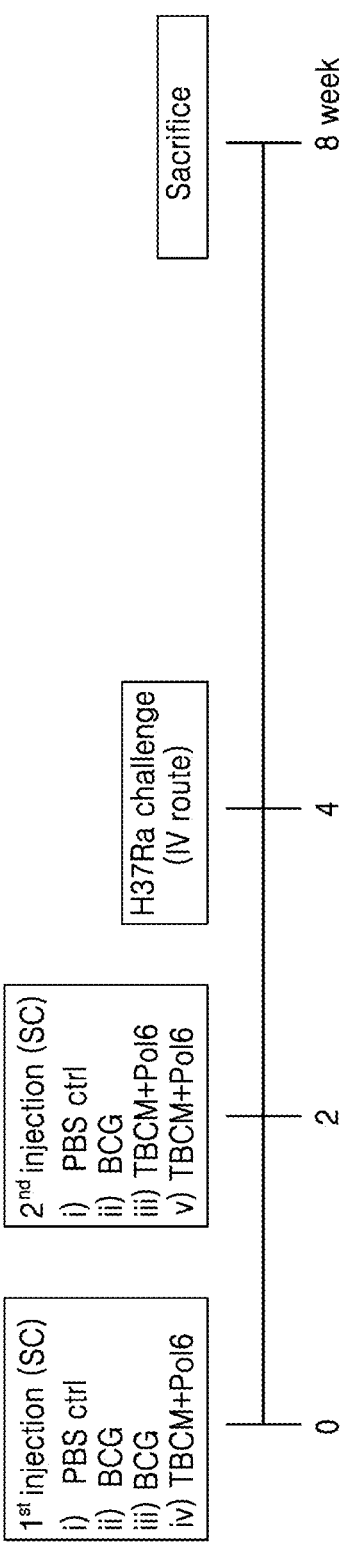
FIG. 20(A) shows a BCG prime-TBCM (P016) boosting immunization schedule.
Figure 20B:
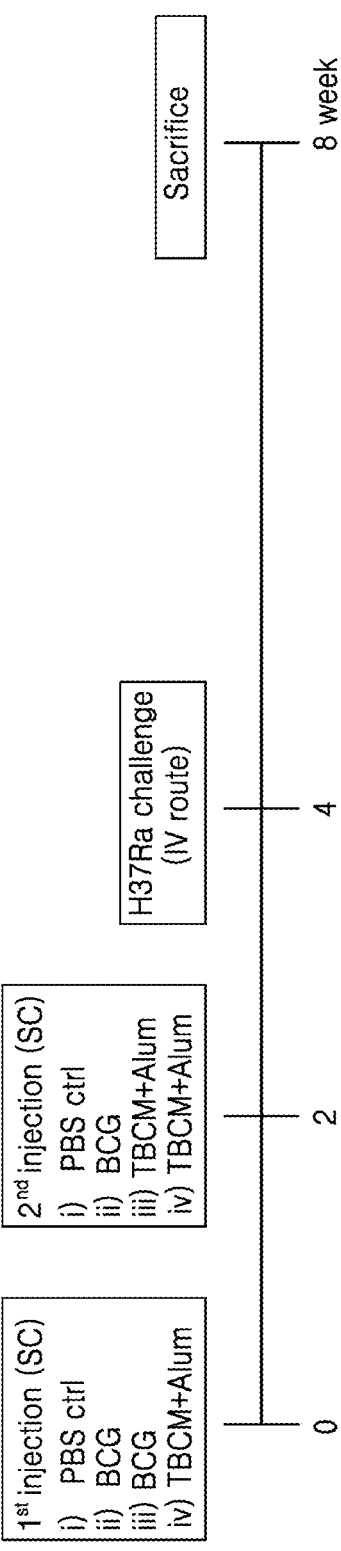
FIG. 20(B) shows a BCG prime-TBCM (Alum) boosting immunization schedule. After completion of immunization, the mouse was sacrificed 4 weeks after H37Ra infection (IV) to proceed and intra-organ CFU and lung tissue H%E staining.
Figure 21A:
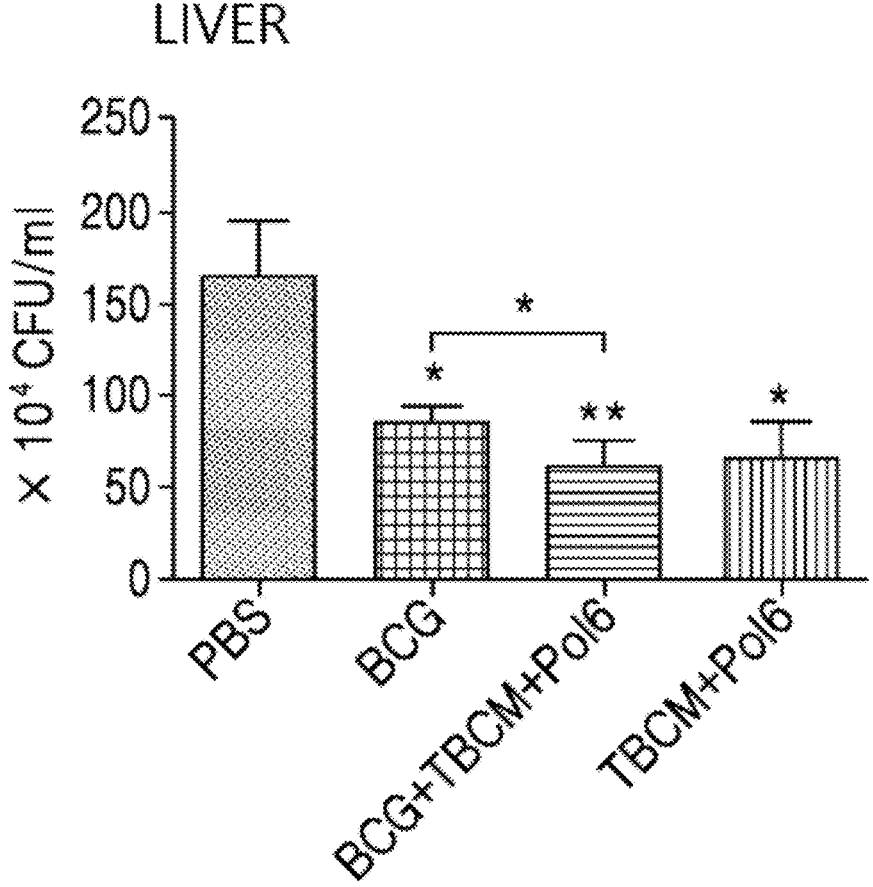
FIG. 21(A) to 21(C) represent BCG prime-TBCM (P016) boosting immunity.
Figure 21B:
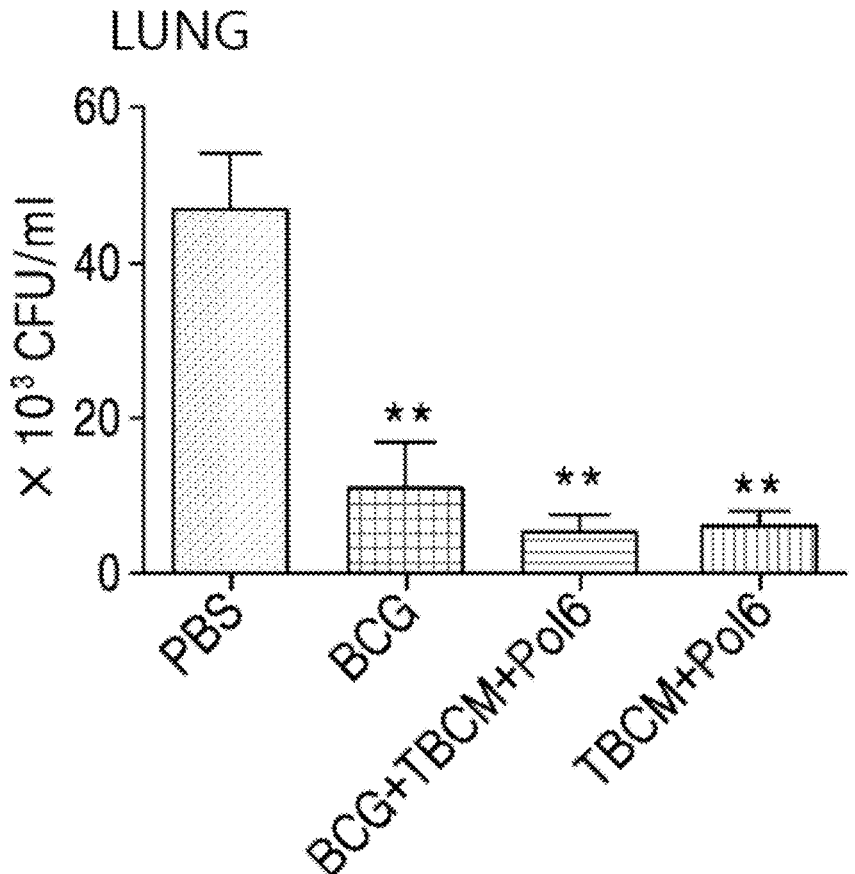
Figure 21C:
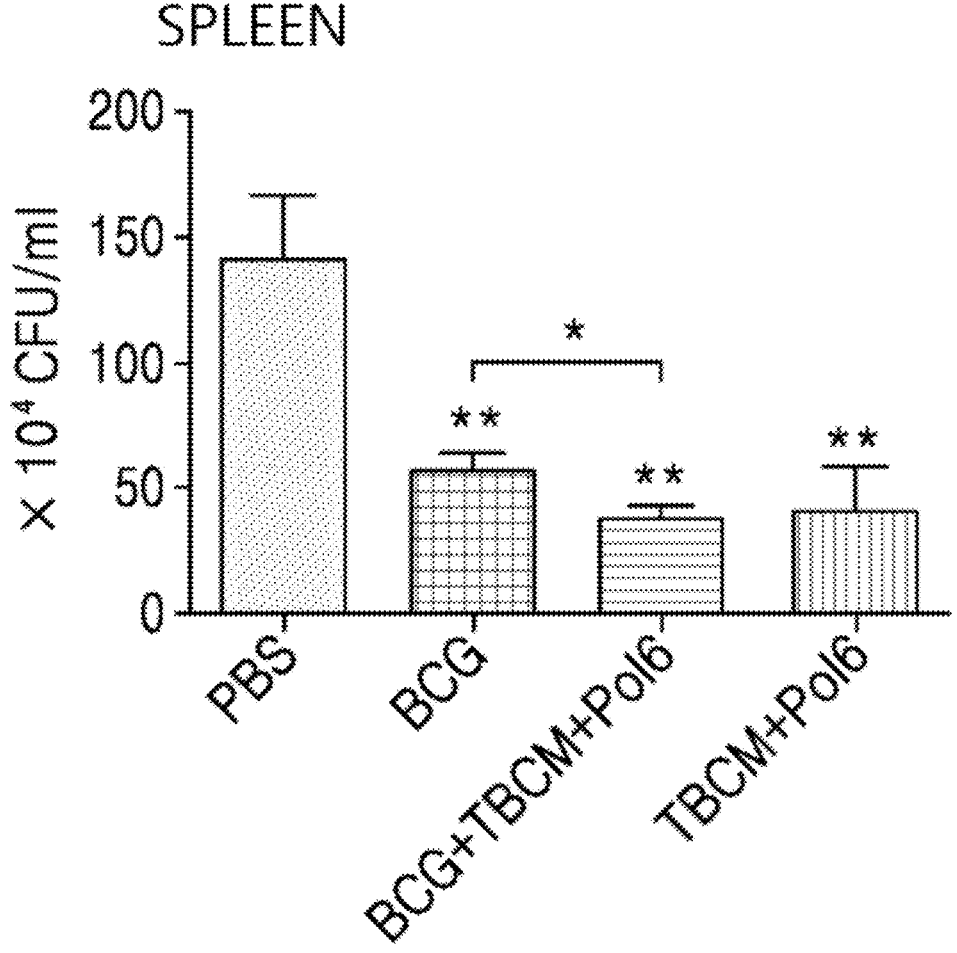
Figure 21D:
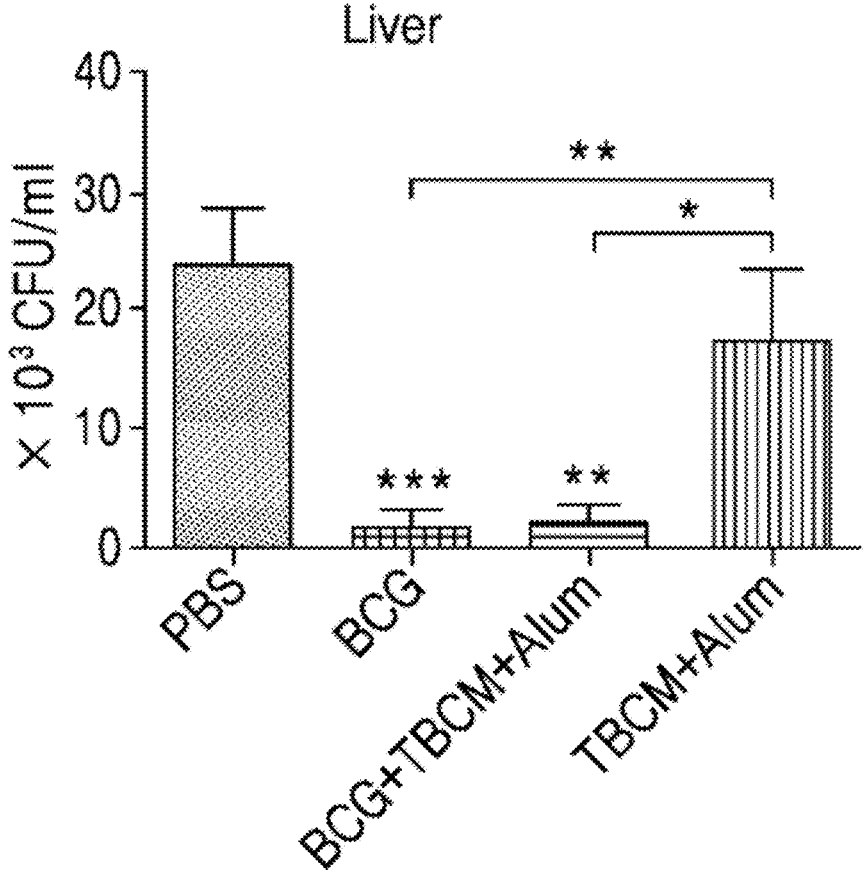
FIG. 21(D) to 21(F) represent BCG prime-TBCM (Alum) boosting immunity (statistical significance is tested by Student-t-test, *, P<0.05; , P<0.01; *, P<0.001).
Figure 21E:
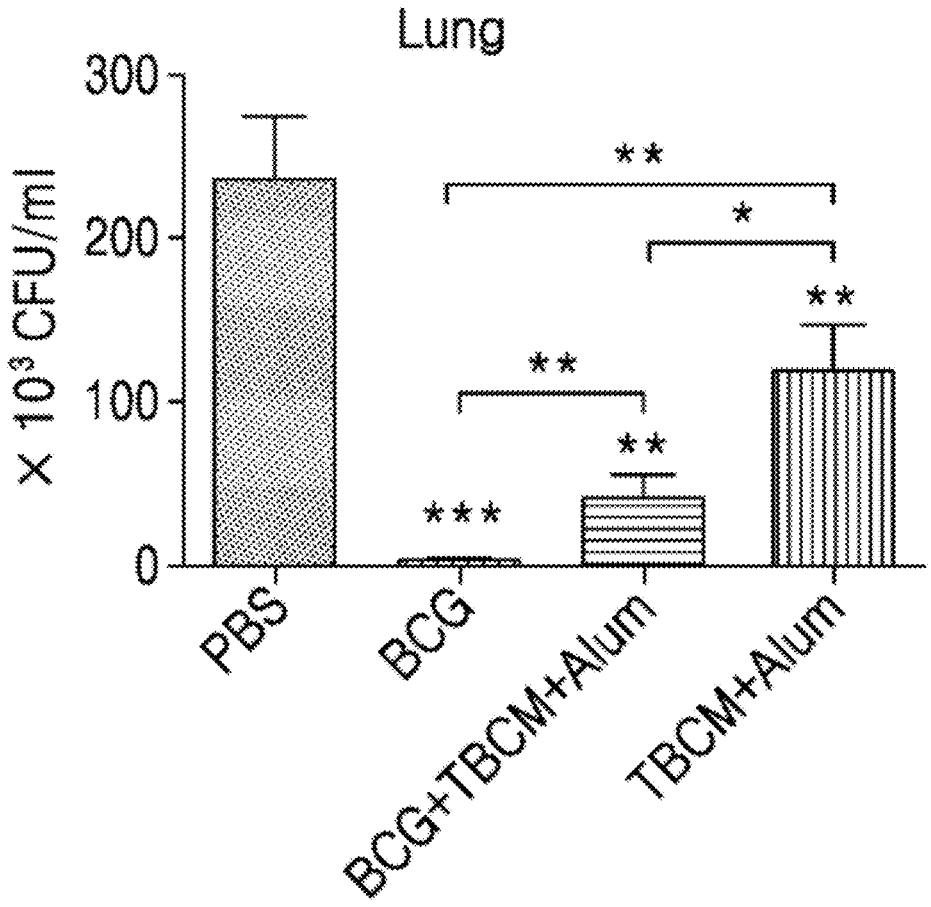
Figure 21F:
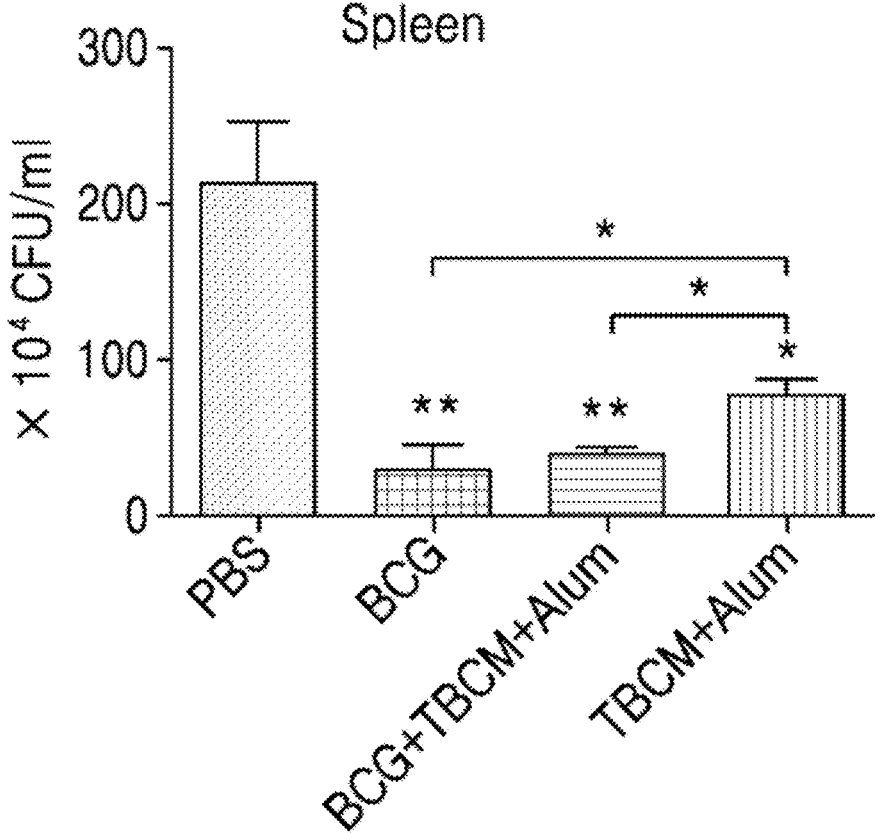
Figure 22A:
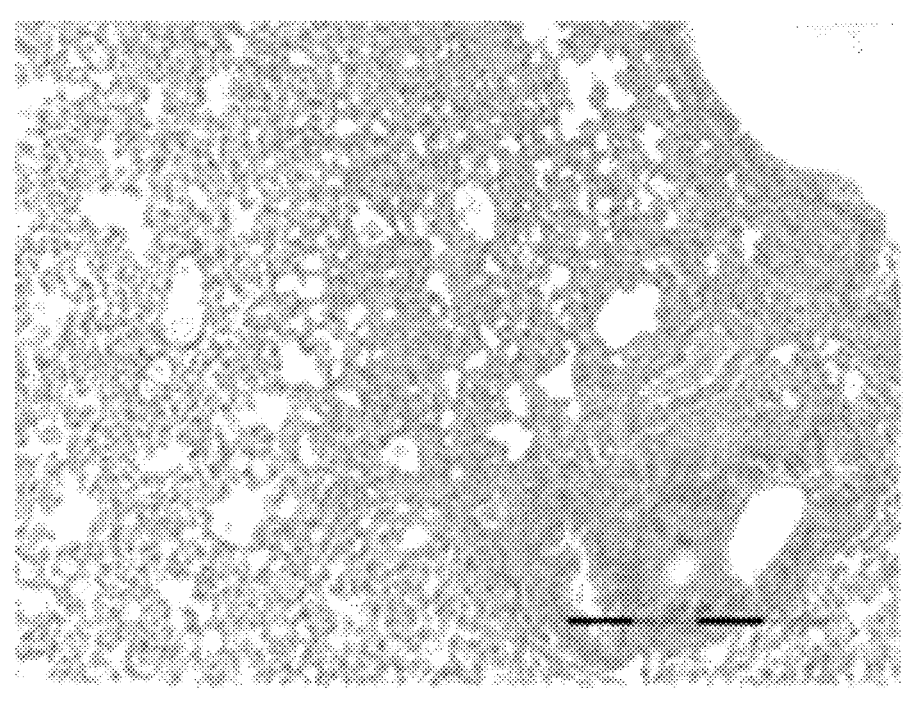
FIG. 22 shows H&E staining photographs of lung tissue of H37Ra-infected mice after BCG prime-TBCM (Pol6) boosting immunization.
Figure 22B:
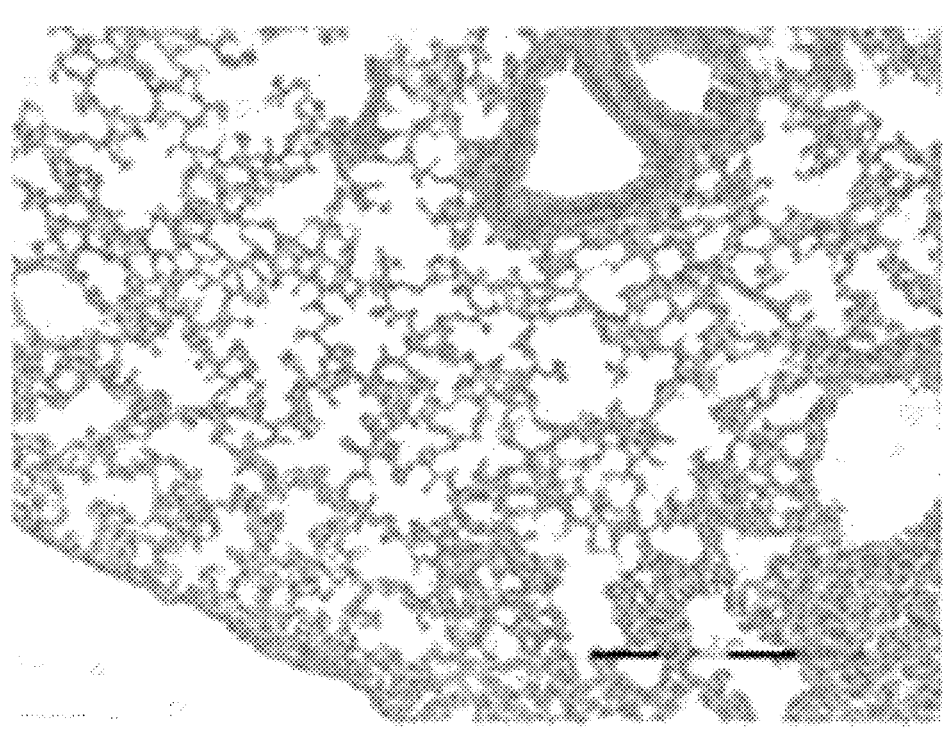
Figure 22C:
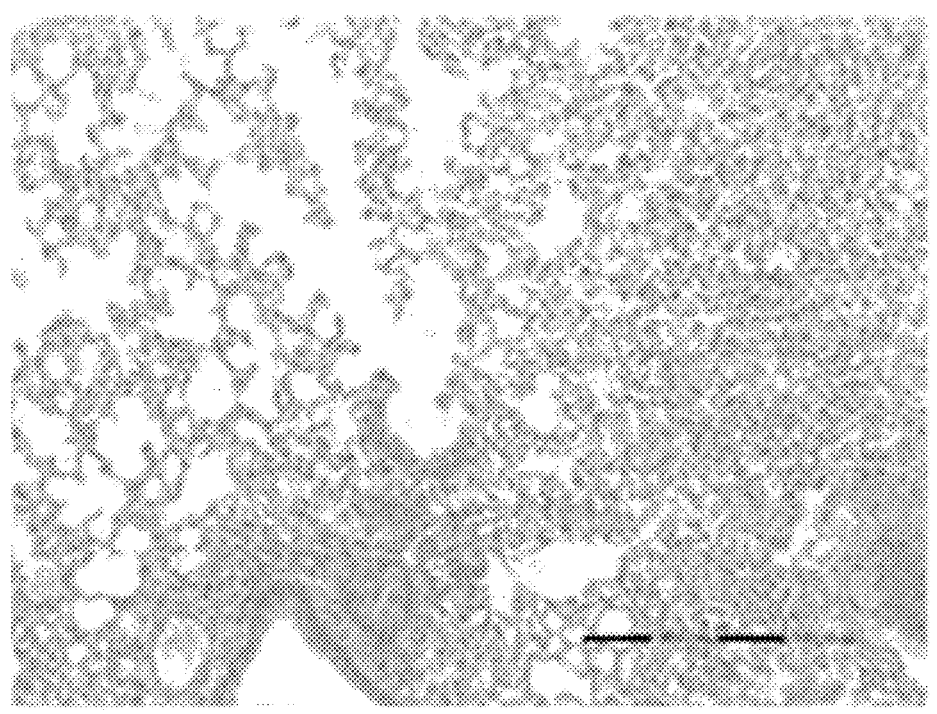
Figure 22D:
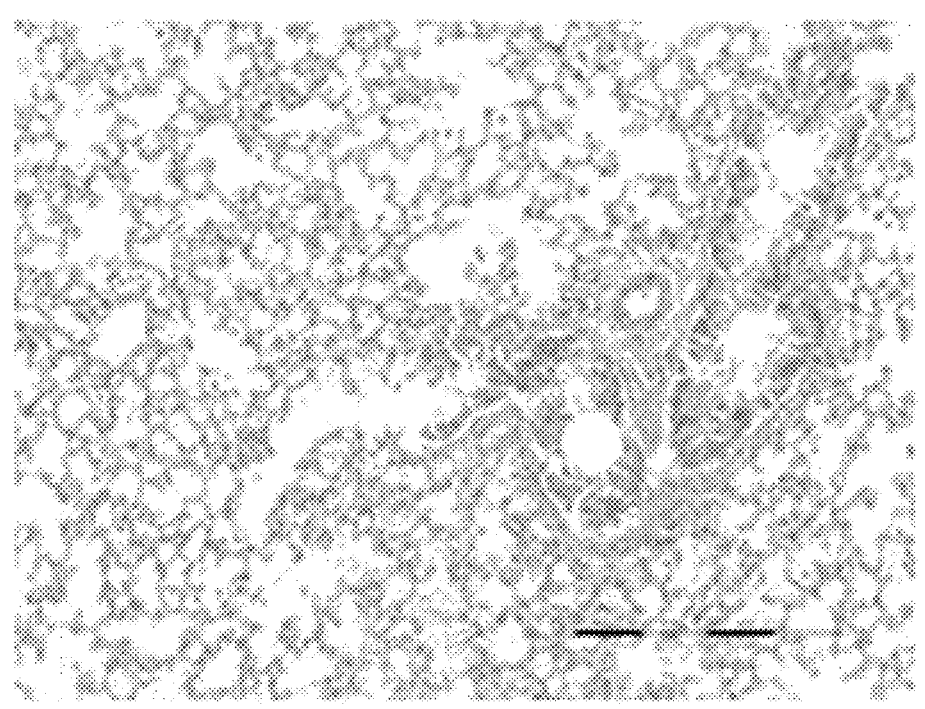
Figure 23A:
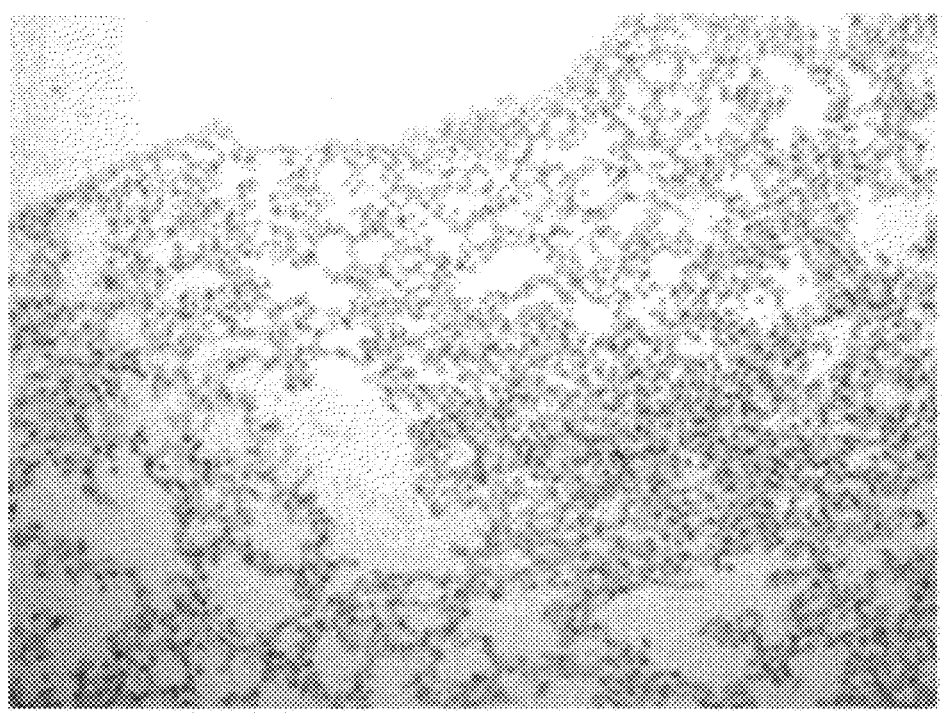
FIG. 23 shows H&E staining photographs of lung tissue of a H37Ra-infected mouse after BCG prime-TBCM (Alum) boosting immunization.
Figure 23B:
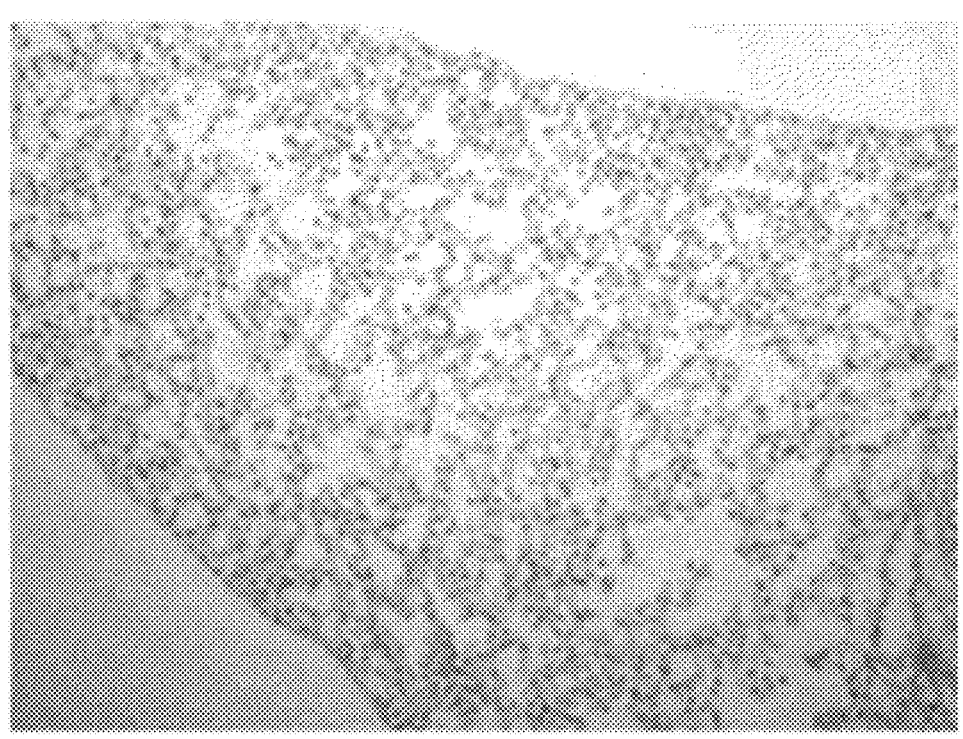
Figure 23C:
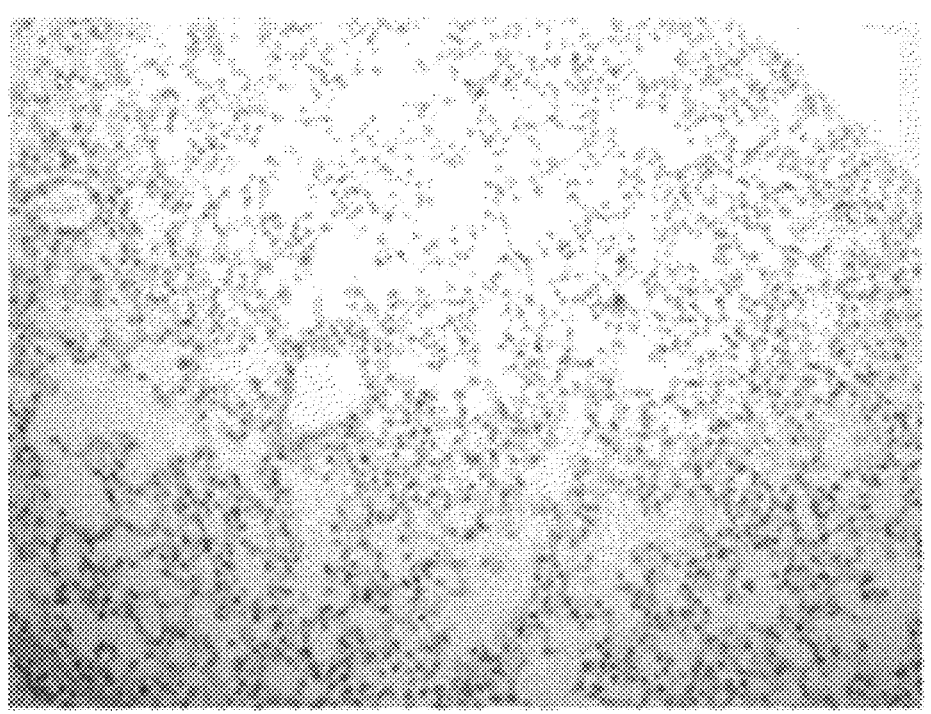
Figure 23D:
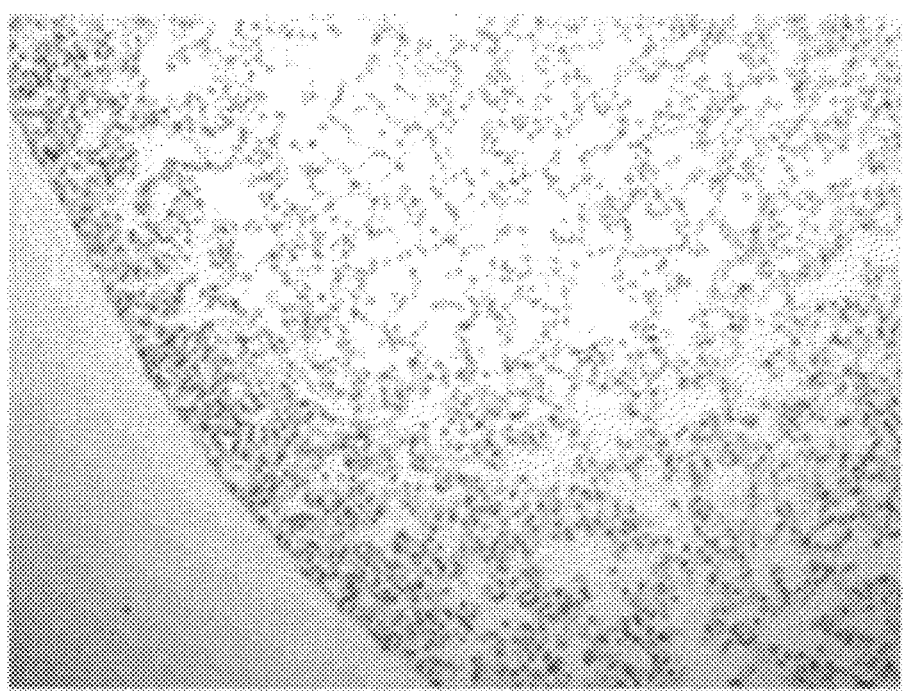

(4) Evaluation of Ability for *M. tuberculosis* Defense by BCG-Prime TBCM (with Adjuvant)-Boosting Immunization According to the schedule shown in FIG. 20, mice were immunized with BCG first which is used as a conventional vaccine for tuberculosis (BCG prime), and then immunized again by TBCM boosting (with TBCM+Alum or TBCM+Pol6). Then, the mice undergoing BCG prime-TBCM boosting immunization immunized through BCG prime-TBCM boosting were infected (by intravenous injection, IV) with a H37Ra strain. The mice were sacrificed after weeks of the infection, and the number of H37Ra bacteria (CFU) in organs and inflammatory response patterns in lung tissue were confirmed by H&E staining. The concentrations of TBCM protein and adjuvants used for the immunization and the number of BCG bacteria were as follows:

i) TBCM (10 µg/mouse);
  ii) Alum (100 µg/mouse);
  iii) Pol6 (5 µg/mouse); and
  iv) BCG ($1 \times 10^6$ CFU/mouse).

1) Confirmation of CFU in Organs

After the mice immunized through BCG prime-TBCM boosting were infected with H37Ra bacteria (FIG. 20), the mice were sacrificed, and each organ (liver, lung, and spleen) was homogenized and diluted in PBS at an appropriate dilution factor. A portion of each dilution was spread on a 7H10 solid medium (supplemented with OADC), and then cultured for about 4 weeks in a 5% $CO_2$ incubator at 37° C. Thereafter, the number of grown colonies was confirmed and CFU was calculated.

As a result, it was confirmed that the H37Ra CFU tended to decrease in each organ of all immunization groups (with BCG alone and with BCG prime-TBCM boosting), compared to the PBS group. Among the immunization groups, a statistically significant decrease in CFU was shown in the group boosted with a combination of TBCM+Pol6 showed compared to the group immunized with BCG alone, and likewise, a decrease in CFU was shown in the group immunized with a combination of TBCM+Pol6 compared to the group immunized with BCG only (FIG. 21).

The CPU (in lungs) in the group immunized with TBCM+Alum boosting was at a similar level (to that in liver and spleen) or relatively high in the group immunized with BCG only, but was significantly reduced compared to group immunized with TBCM+Alum alone (FIG. 21).

Recently, the most popular vaccination method in the vaccine research for tuberculosis is a heterologous prime-boosting method, which is known to be very effective in forming strong and sustainable humoral and cellular immunity. These results above suggest that TBCM can be effectively applied also in the BCG prime-boosting immunoassay.

2) Histopathological Evaluation of Lung Tissue

After mice immunized with BCG prime-TBCM boosting were infected with H37Ra bacteria (FIG. 20), the mice were sacrificed and a portion of lung tissue was fixed with formalin. The fixed samples were embedded in paraffin and subjected to H&E staining. The stained tissue was observed under a microscope to confirm the difference in inflammatory response.

As a result of confirming the H&E staining results, it was confirmed that inflammation tended to be alleviated (decreased number of cells in tissue, decreased thickness of alveolar walls, etc.) in the group immunized with BCG alone as well as in the group immunized with BCG prime-TBCM boosting (with Pol6 or Alum), compared to the group infected with H37Ra alone. In addition, the inflammation tended to be alleviated in the groups immunized with TBCM+Pol6 and TBCM+Alum, respectively (FIGS. 22 and 23).

The results above indicate the possibility that the BCG prime-TBCM boosting immunization method can induce effective protective immunity to defend against infected *M. tuberculosis*. In addition, it was confirmed that the immunization with TBCM only (with Pol6 or Alum) was able to effectively induce an immune response against *M. tuberculosis*.

---

The invention claimed is:

1. A method of preventing tuberculosis, the method comprising administering purified *Mycobacterium tuberculosis* chorismate mutase (TBCM) to a subject in need thereof.

2. The method of claim 1, wherein the TBCM is a protein expressed by a polynucleotide consisting of the base sequence of GenBank Gene ID: 885772.

3. The method of claim 1, further comprising administering an immune adjuvant to the subject.

4. The method of claim 3, wherein the immune adjuvant is at least one selected from AS01 which is a liposome mixed with monophosphoryl lipid A and saponin QS-21, IC31 consisting of an oligo nucleotide and a cationic peptide, CFA01 which is a cationic liposome, Alum consisting of aluminum salts, and a peptide of SEQ ID NO: 1.

5. The method of claim 1, wherein the method increases an expression level of at least one selected from IFN-γ, IL-12, IL-17, and TNF-α.

6. The method of claim 1, wherein the method enhances induction of Th1 cell-mediated immunity.

7. The method of claim 1, wherein an administration route of the chorismate mutase is at least one selected from subcutaneous injection and intranasal injection.

8. An immune-boosting method for preventing tuberculosis, the method comprising administering purified *Mycobacterium tuberculosis* chorismate mutase (TBCM) to a subject in need thereof.

9. The method of claim 8, wherein TBCM is a protein expressed by a polynucleotide consisting of the base sequence of GenBank Gene ID: 885772.

10. The method of claim 8, further comprising administering an immune adjuvant to the subject.

11. The method of claim 10, wherein the immune adjuvant is at least one selected from AS01 which is a liposome mixed with monophosphoryl lipid A and saponin QS-21, IC31 consisting of an oligo nucleotide and a cationic peptide, CFA01 which is a cationic liposome, Alum consisting of aluminum salts, and a peptide of SEQ ID NO: 1.

12. The method of claim 8, wherein the method increases an expression level of at least one selected from IFN-γ, IL-12, IL-17, and TNF-α.

13. The method of claim 8, wherein the method enhances induction of Th1 cell-mediated immunity.

14. The method of claim 8, wherein an administration route of the chorismate mutase is at least one selected from subcutaneous injection and intranasal injection.

15. The method of claim 8, the method is boosting with an attenuated virus that expresses a tuberculosis antigen or Bacillus Calmette-Guerin (BCG) prime.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: poly6 peptide

<400> SEQUENCE: 1

Gly Arg Leu Val Phe Gln
1               5

<210> SEQ ID NO 2
<211> LENGTH: 199
<212> TYPE: PRT
<213> ORGANISM: Artificial Sequence
<220> FEATURE:
<223> OTHER INFORMATION: Mycobacterium tuberculosis

<400> SEQUENCE: 2

Met Leu Thr Arg Pro Arg Glu Ile Tyr Leu Ala Thr Ala Val Ser Ile
1               5                   10                  15

Gly Ile Leu Leu Ser Leu Ile Ala Pro Leu Gly Pro Pro Leu Ala Arg
            20                  25                  30

Ala Asp Gly Thr Ser Gln Leu Ala Glu Leu Val Asp Ala Ala Ala Glu
        35                  40                  45

Arg Leu Glu Val Ala Asp Pro Val Ala Ala Phe Lys Trp Arg Ala Gln
    50                  55                  60

Leu Pro Ile Glu Asp Ser Gly Arg Val Glu Gln Gln Leu Ala Lys Leu
65                  70                  75                  80

Gly Glu Asp Ala Arg Ser Gln His Ile Asp Pro Asp Tyr Val Thr Arg
                85                  90                  95

Val Phe Asp Asp Gln Ile Arg Ala Thr Glu Ala Ile Glu Tyr Ser Arg
            100                 105                 110

Phe Ser Asp Trp Lys Leu Asn Pro Ala Ser Ala Pro Pro Glu Pro Pro
        115                 120                 125

Asp Leu Ser Ala Ser Arg Ser Ala Ile Asp Ser Leu Asn Asn Arg Met
    130                 135                 140

Leu Ser Gln Ile Trp Ser His Trp Ser Leu Leu Ser Ala Pro Ser Cys
145                 150                 155                 160

Ala Ala Gln Leu Asp Arg Ala Lys Arg Asp Ile Val Arg Ser Arg His
                165                 170                 175

Leu Asp Ser Leu Tyr Gln Arg Ala Leu Thr Thr Ala Thr Gln Ser Tyr
            180                 185                 190

Cys Gln Ala Leu Pro Pro Ala
            195

<210> SEQ ID NO 3
```

-continued

```
<211> LENGTH: 246
<212> TYPE: PRT
<213> ORGANISM: Artificial Sequence
<220> FEATURE:
<223> OTHER INFORMATION: TBCM expression vector(pET28a)

<400> SEQUENCE: 3

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Met Leu Thr Arg Pro Arg Glu Ile Tyr Leu Ala Thr Ala Val
        35                  40                  45

Ser Ile Gly Ile Leu Leu Ser Leu Ile Ala Pro Leu Gly Pro Pro Leu
    50                  55                  60

Ala Arg Ala Asp Gly Thr Ser Gln Leu Ala Glu Leu Val Asp Ala Ala
65                  70                  75                  80

Ala Glu Arg Leu Glu Val Ala Asp Pro Val Ala Ala Phe Lys Trp Arg
                85                  90                  95

Ala Gln Leu Pro Ile Glu Asp Ser Gly Arg Val Glu Gln Gln Leu Ala
            100                 105                 110

Lys Leu Gly Glu Asp Ala Arg Ser Gln His Ile Asp Pro Asp Tyr Val
        115                 120                 125

Thr Arg Val Phe Asp Asp Gln Ile Arg Ala Thr Glu Ala Ile Glu Tyr
    130                 135                 140

Ser Arg Phe Ser Asp Trp Lys Leu Asn Pro Ala Ser Ala Pro Pro Glu
145                 150                 155                 160

Pro Pro Asp Leu Ser Ala Ser Arg Ser Ala Ile Asp Ser Leu Asn Asn
            165                 170                 175

Arg Met Leu Ser Gln Ile Trp Ser His Trp Ser Leu Leu Ser Ala Pro
            180                 185                 190

Ser Cys Ala Ala Gln Leu Asp Arg Ala Lys Arg Asp Ile Val Arg Ser
        195                 200                 205

Arg His Leu Asp Ser Leu Tyr Gln Arg Ala Leu Thr Thr Ala Thr Gln
    210                 215                 220

Ser Tyr Cys Gln Ala Leu Pro Pro Ala Lys Leu Ala Ala Ala Leu Glu
225                 230                 235                 240

His His His His His His
            245
```